(12) United States Patent
Kuehne et al.

(10) Patent No.: US 12,722,207 B2
(45) **Date of Patent: *Sep. 1, 2026**

(54) OSCILLATING TOOL

(71) Applicant: Black & Decker Inc., New Britain, CT (US)

(72) Inventors: Brent A. Kuehne, Red Lion, PA (US); Oleksiy P. Sergyeyenko, Baldwin, MD (US); Kevin W. Covell, Parkton, MD (US)

(73) Assignee: Black & Decker Inc., New Britain, CT (US)

( * ) Notice: Subject to any disclaimer, the term of this patent is extended or adjusted under 35 U.S.C. 154(b) by 546 days.

This patent is subject to a terminal disclaimer.

(21) Appl. No.: 17/964,431

(22) Filed: Oct. 12, 2022

(65) Prior Publication Data

US 2023/0081102 A1 Mar. 16, 2023

Related U.S. Application Data

(63) Continuation of application No. 17/064,083, filed on Oct. 6, 2020, now Pat. No. 11,498,180, which is a (Continued)

(51) Int. Cl.

*B23B 31/10* (2006.01)
*B24B 23/04* (2006.01)

(Continued)

(52) U.S. Cl.

CPC .............. *B23B 31/10* (2013.01); *B24B 23/04* (2013.01); *B24B 45/006* (2013.01); *B25F 3/00* (2013.01);

(Continued)

(58) Field of Classification Search

CPC ......... B23B 31/10; B23B 31/19; B24B 23/04; B24B 45/006; B27B 5/32; B27B 19/006; Y10T 279/33

See application file for complete search history.

(56) References Cited

U.S. PATENT DOCUMENTS 5,489,285 A * 2/1996 Goris ..................... B23D 51/10 D24/146
6,503,253 B1 * 1/2003 Fletcher ................ B27B 19/006 606/82

(Continued)

*Primary Examiner* — Eric A. Gates
(74) *Attorney, Agent, or Firm* — Michael J. Aronoff

(57) ABSTRACT

A clamp arrangement for securing an accessory to an oscillating power tool can include a clamp assembly including a first clamp member that moves relative to the accessory between a closed position wherein the clamp assembly retains the accessory and an open position wherein the first clamp is offset from the accessory permitting removal of the first accessory from the clamp assembly. The clamp assembly can further comprise a second clamp member having a first portion that opposes the first clamp member and cooperates with the first clamp member to clamp the accessory between the first and second clamp members. An attachment plate can carry the clamp assembly. The attachment plate can have a first mating detail formed thereon that is configured to selectively and removably mate with a complementary second mating detail on the power tool in an assembled position.

7 Claims, 43 Drawing Sheets

Related U.S. Application Data continuation of application No. 16/141,425, filed on Sep. 25, 2018, now Pat. No. 11,045,919, which is a continuation of application No. 15/452,197, filed on Mar. 7, 2017, now Pat. No. 10,124,461, which is a continuation of application No. 15/351,513, filed on Nov. 15, 2016, now Pat. No. 10,207,385, which is a continuation of application No. 14/013,065, filed on Aug. 29, 2013, now Pat. No. 9,539,647, which is a continuation of application No. 13/826,374, filed on Mar. 14, 2013, now abandoned, which is a continuation-in-part of application No. 13/362,637, filed on Jan. 31, 2012, now Pat. No. 9,186,770, which is a continuation-in-part of application No. 12/942,098, filed on Nov. 9, 2010, now Pat. No. 8,925,931.

(60) Provisional application No. 61/664,454, filed on Jun. 26, 2012, provisional application No. 61/622,894, filed on Apr. 11, 2012, provisional application No. 61/329,480, filed on Apr. 29, 2010.

(51) Int. Cl.

| | |
|---|---|
| ***B24B 45/00*** | (2006.01) |
| ***B25F 3/00*** | (2006.01) |
| ***B27B 5/32*** | (2006.01) |
| ***B27B 19/00*** | (2006.01) |
| *A61B 17/14* | (2006.01) |
| *B23B 31/19* | (2006.01) |

(52) U.S. Cl.

CPC .............. *B27B 5/32* (2013.01); *B27B 19/006* (2013.01); *A61B 17/142* (2016.11); *B23B 31/19* (2013.01); *Y10T 279/18* (2015.01); *Y10T 279/33* (2015.01); *Y10T 279/3451* (2015.01)

(56) References Cited

U.S. PATENT DOCUMENTS

| | | | | |
|---|---|---|---|---|
| 7,189,239 | B2 * | 3/2007 | Fisher | B27B 19/006 606/176 |
| 7,527,628 | B2 * | 5/2009 | Fletcher | B27B 19/006 606/177 |
| 10,124,461 | B2 * | 11/2018 | Kuehne | B24B 45/006 |
| 11,045,919 | B2 * | 6/2021 | Kuehne | B24B 45/006 |
| 11,498,180 | B2 * | 11/2022 | Kuehne | B24B 45/006 |
| 2004/0098000 | A1 * | 5/2004 | Kleinwaechter | B23D 61/123 D24/146 |
| 2004/0204731 | A1 * | 10/2004 | Gant | B27B 5/32 606/170 |
| 2006/0282108 | A1 * | 12/2006 | Tanner | B23B 31/4073 606/176 |
| 2007/0060030 | A1 * | 3/2007 | Pollak | B27B 5/32 451/359 |
| 2007/0295156 | A1 * | 12/2007 | Ziegler | B24B 23/04 403/44 |
| 2008/0190259 | A1 * | 8/2008 | Bohne | B24B 23/04 83/666 |
| 2009/0312761 | A1 * | 12/2009 | Boykin | B27B 5/32 606/82 |
| 2010/0056029 | A1 * | 3/2010 | Grunikiewicz | B24B 45/006 451/442 |
| 2011/0291368 | A1 * | 12/2011 | Chen | B24B 45/00 279/143 |
| 2011/0309589 | A1 * | 12/2011 | Maras | B25F 3/00 279/143 |

* cited by examiner 140
24
142
10
130
26
134
134
132
132
126
120

122
94
92
86
96
30
36
91
98
84
90
87
118
116
116
112
48
44
110
40
46
42
108
102
32
104
100
104
102
152
150
148
74
72
76
14a
78
38
70
80
146

24
142
122
160
130
26
102
116
44
102
48
42
40
32
104
14a
36
38
82

24
142
116
44
160
130
26
102
102
42
40
48
32
104
36
76
14a
38

24
142
116
44
160
130
26
102
102
42
40
48
32
104
150
148
36
76
14a
38
152

140
24
142
116
44
160
130
26
102
102
48
42
40
36
104
82
38
150
148
30°
14a 140
24
142
116
44
130
26
160
102
102
48
42
40
36
104
82
38
14a 140
24
142
122
116
44
130
26
102
160
102
48
104
42
40
38
14a

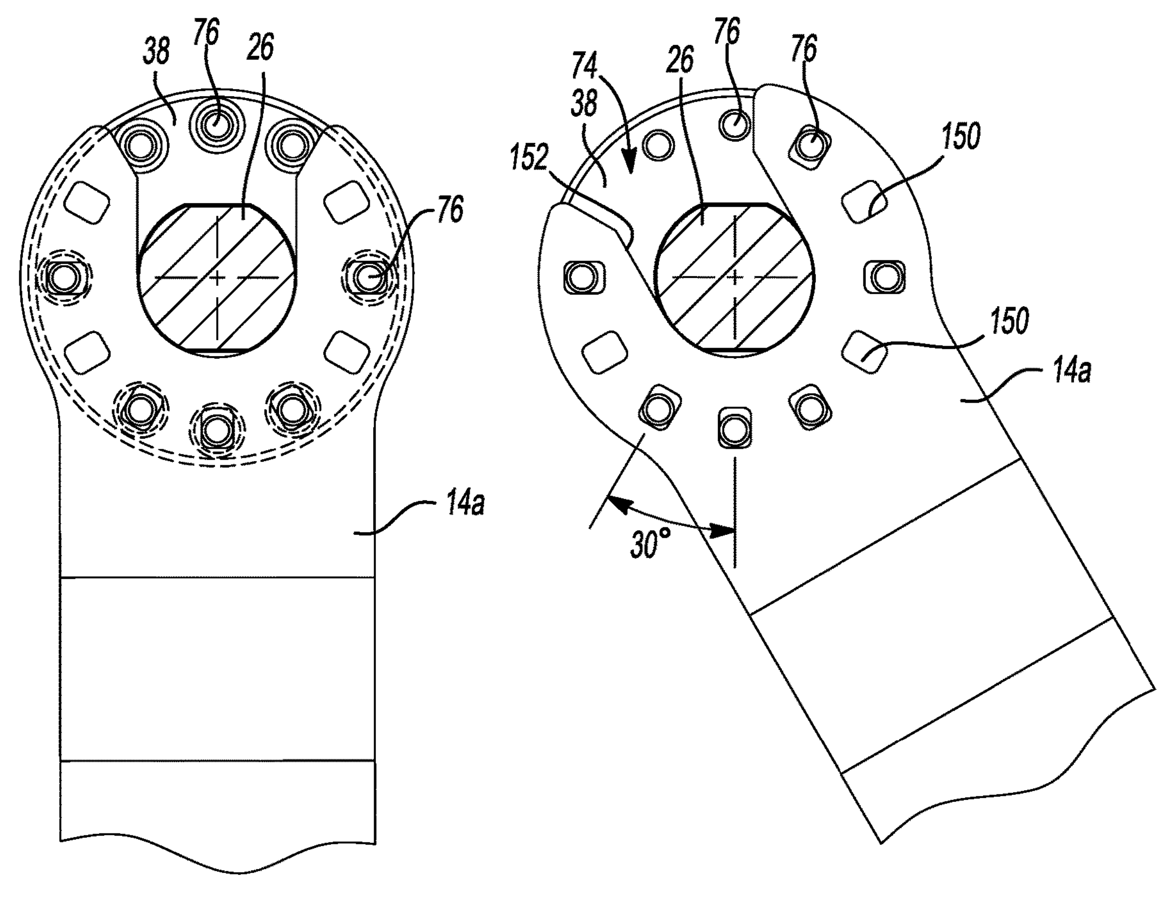
Fig-13
Fig-14
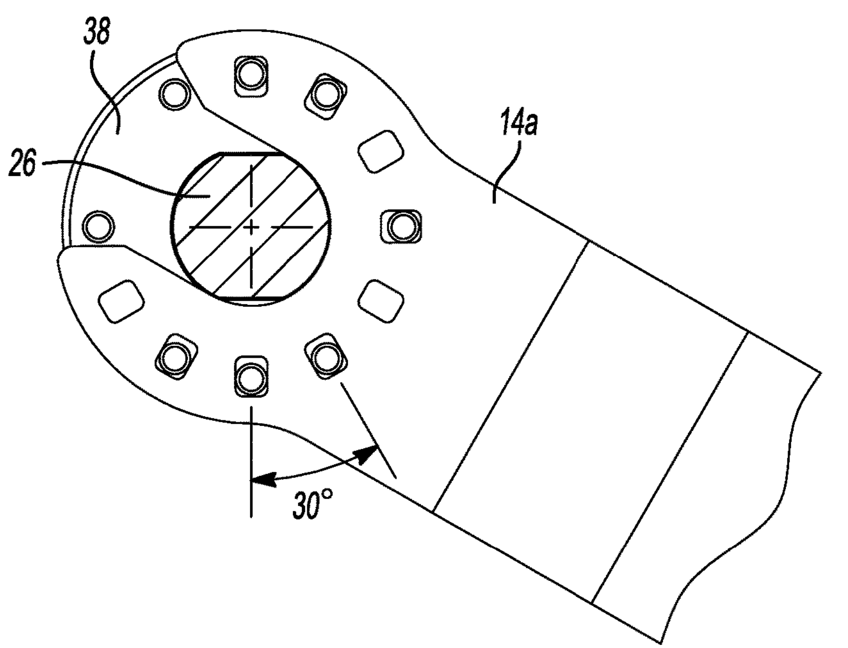
Fig-15

10
48
160
108
112
30
50
14b
52
56
54
130
140
96
86
90
98
36
87
70
74
26
126
120
88
76
38
82
122
110
91
32
42

140
130
10
48
26
160
110
126
120
96
86
108
112
30
32
90
91
98
88
74
36
54
56
76
87
14b
50
38
70
82
52

140
130
10
48
26
160
126
110
120
96
86
108
112
91
90
30
98
32
88
74
36
54
56
76
87
14b
50
38
70
82
52

26
134
196
134
74
76
192
190
194
38
198

14d
26
192
190
198
134
134
76
38

14d 26
190
134
76
192
198
134
38
198
14d 74
26
76
196
194
192
198
14d 76
74
204
76
26
38
200
14e 202
204
200
14e 348
14f
346
350
360
352
358

264
258
276
256
266
238
270
254
272
226
260
262
256
258
250

416a
504
510a
530
440
520
490
476
512
514
494
516
474
496
456
452
442
450
446
518
464
448
466
460
462
454
478
548
500

689
690
688
693
686
610
684
640
696
692
676
646
674
614
648

416a
510a
504
696
694
520
516
494
496
518
480
446
466
14g
460
548
464
462
500
490
476
492
478
448
680
678

722
740
710
720
728
732
730
736
734
726
712
742
750
744
748
746
770
14f
714
756
754
758
716
760
762

452
442
450
456
454
710
736
740
726
728
732
730
712
742
750
770
748
720
14f
714
756
754
758
716
760
762

716
710
726
728
732
712
720
714
14f
760
762
754
452
442
450
456
454

854
850
858
852
846
848
844
820
810
828
860
870
866
824
822
872
838
814

850
852
848
846
844
820
860
862
864
866
870
826
828
814
830
824
880
878
872
874
838
504
873
500

810
844
848
854
850
504
870
872
828
873
840
838
14g
878
880
500
864
830
416a
862
866
874
824
822
832
820

948
954
950
958
952
946
944
920
910
934
960
970
922
924
972
914
938
940

946
948
944
920
970
960
962
966
964
926
928
934
930
924
978
980
974
932
972
973
938
940
504'
500'

914
972
14g
944
948
954
950
960
970
928
973
940
938
500'
978
980
964
930
932
966
974
924
922
920
962
416a 1010
1146
1142
1148
1140
1024
1034
1050
1030

1066
1010'
1142'
1146'
1020
1022
1024'
1148'
1014

1032
1080
1074
1078
1078
1074
1080
1082
1080
1076
1074
1078
1076

1062
1054
1060
1070
1070
1056
1050
1070
1020

1052
1032
1080
1076
1074
1078

1010
1014
1022
1024
1030
1032
1034
1042
1050
1053
1054
1062
1068
1070
1080
1090
1092
1110
1112
1114

OSCILLATING TOOL

CROSS-REFERENCE TO RELATED APPLICATIONS

This application is a continuation of U.S. patent application Ser. No. 17/064,083 filed Oct. 6, 2020, which is a continuation of U.S. patent application Ser. No. 16/141,425 filed Sep. 25, 2018 (now U.S. Pat. No. 11,045,919 issued Jun. 29, 2021) which is a continuation of U.S. patent application Ser. No. 15/452,197 filed Mar. 7, 2017 (now U.S. Pat. No. 10,124,461 issued Nov. 13, 2018) which is a continuation of U.S. patent application Ser. No. 15/351,513 filed Nov. 15, 2016 (now U.S. Pat. No. 10,2074,385 issued Feb. 19, 2019) which is a continuation of U.S. patent application Ser. No. 14/013,065 filed Aug. 29, 2013 (now U.S. Pat. No. 9,539,647 issued Jan. 10, 2017), which is a continuation of U.S. patent application Ser. No. 13/826,374 filed Mar. 14, 2013, which is a continuation-in-part of U.S. application Ser. No. 13/362,637 filed on Jan. 31, 2012 (now U.S. Pat. No. 9,186,770 issued Nov. 17, 2015), which is a continuation-in-part of U.S. patent application Ser. No. 12/942,098 filed on Nov. 9, 2010 (now U.S. Pat. No. 8,925,931 issued Jan. 6, 2015), which claims the benefit and priority of U.S. Provisional Application No. 61/329,480, filed Apr. 29, 2010. This application also claims priority to US Provisional Application Nos. 61/622,894 filed on Apr. 11, 2012, and 61/664,454 filed on Jun. 26, 2012, via U.S. patent application Ser. No. 13/826,374, which claims priority to U.S. Provisional Application Nos. 61/622,894 and 61/664,454. The entire disclosures of the above applications are incorporated herein by reference.

FIELD

The present disclosure relates to power hand tools and more specifically to a clamp arrangement for releasably securing an accessory to an oscillating power hand tool.

BACKGROUND

This section provides background information related to the present disclosure which is not necessarily prior art.

Power hand tools are provided in many examples for performing a wide range of tasks. For example, some power hand tools can include an output member that is driven by a motor and that couples with an accessory to perform a working operation onto a work piece. For example, some hand tools can provide various configurations for attaching cutting accessories, grinding accessories, sanding accessories and the like. Some power hand tools are configured as oscillating tools that are operable to transmit an oscillating motion onto the accessory.

During the course of performing a working operation, a user may want to exchange one accessory for another accessory. For example, a user may want to exchange one grinding accessory with another grinding accessory or one sanding platen with another sanding platen. Alternatively, a user may wish to replace a cutting accessory with another cutting accessory. It is also contemplated that a user may want to replace a given accessory dedicated to one task (such as sanding) with another accessory dedicated toward another task (such as cutting for example). In any event, many power hand tools require the use of a secondary tool to swap out accessories. For example, many power hand tools require the use of a hand screw driver that can be used to retract a fastener that may lock the accessory to the output member of the power hand tool. In other examples, a wrench or other hand tool may be required to remove or unlock a given accessory from the power hand tool and subsequently lock another accessory back to the power hand tool.

SUMMARY

This section provides a general summary of the disclosure, and is not a comprehensive disclosure of its full scope or all of its features.

A clamp arrangement for securing an accessory to an oscillating power tool can include a clamp assembly including a first clamp member that moves relative to the accessory. The first clamp member can move between a closed position wherein the clamp assembly retains the accessory and an open position wherein the first clamp member is offset from the accessory permitting removal of the first accessory from the clamp assembly while the first clamp member remains coupled to the clamp assembly. The clamp assembly can further comprise a second clamp member having a first portion that opposes the first clamp member and cooperates with the first clamp member to clamp the accessory between the first and second clamp members. An attachment plate can carry the clamp assembly. The attachment plate can have a first mating detail formed thereon that is configured to selectively and removably mate with a complementary second mating detail on the power tool in an assembled position.

According to additional features, the clamp arrangement can further include a fastener that is configured to selectively and removably extend through a portion of the attachment plate and rotationally fix the attachment plate to the output member of the power tool. The fastener can comprise a threaded fastener that threadably mates with a complementary threaded bore defined in the output member. The clamp assembly and the attachment plate can be rotationally fixed with the output member in the assembled position.

The first mating detail can collectively comprise a first mating geometry and a second distinct mating geometry that are configured to selectively and alternatively mate with the complementary second mating detail. The second mating detail can comprise a first tool geometry on a first oscillating tool and a second tool geometry, distinct from the first tool geometry on a second oscillating tool. The first mating geometry can be configured to mate with the first tool geometry of the first oscillating tool in a first configuration. The second mating geometry can be configured to mate with the second tool geometry of the second oscillating tool in a second configuration. The first mating geometry can comprise a keyed recess formed into the attachment plate. The second mating geometry can comprise a plurality of recesses formed around the keyed recess. According to one configuration, the keyed recess comprises a twelve point star. The plurality of recesses can comprise a plurality of oval recesses arranged around the keyed recess.

According to one configuration, the clamp arrangement can comprise a lever having a user engagement portion and a pivot portion including a pivot axle. The lever can be pivotally coupled relative to the attachment plate about the pivot axle between a first position, wherein the clamp assembly is in the closed position and a second position wherein movement of the user engagement portion of the lever causes the clamp assembly to be moved to the open position. In other configurations, a first clamp member body can have a user engagement portion including a circumferential flange extending therefrom. The user engagement portion can be movably coupled relative to the tool body along an axis of the fastener between a first position, wherein the clamp assembly is in the closed position and a second position wherein movement of the user engagement portion causes the clamp assembly to be moved to the open position.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 13-15 are cross-sectional views of the clamp assembly taken through a spindle of the power hand tool and shown with the first accessory rotated at different positions around an axis of the spindle;

Corresponding reference numerals indicate corresponding parts throughout the several views of the drawings.

DETAILED DESCRIPTION

Example embodiments will now be described more fully with reference to the accompanying drawings.

Figure 1:
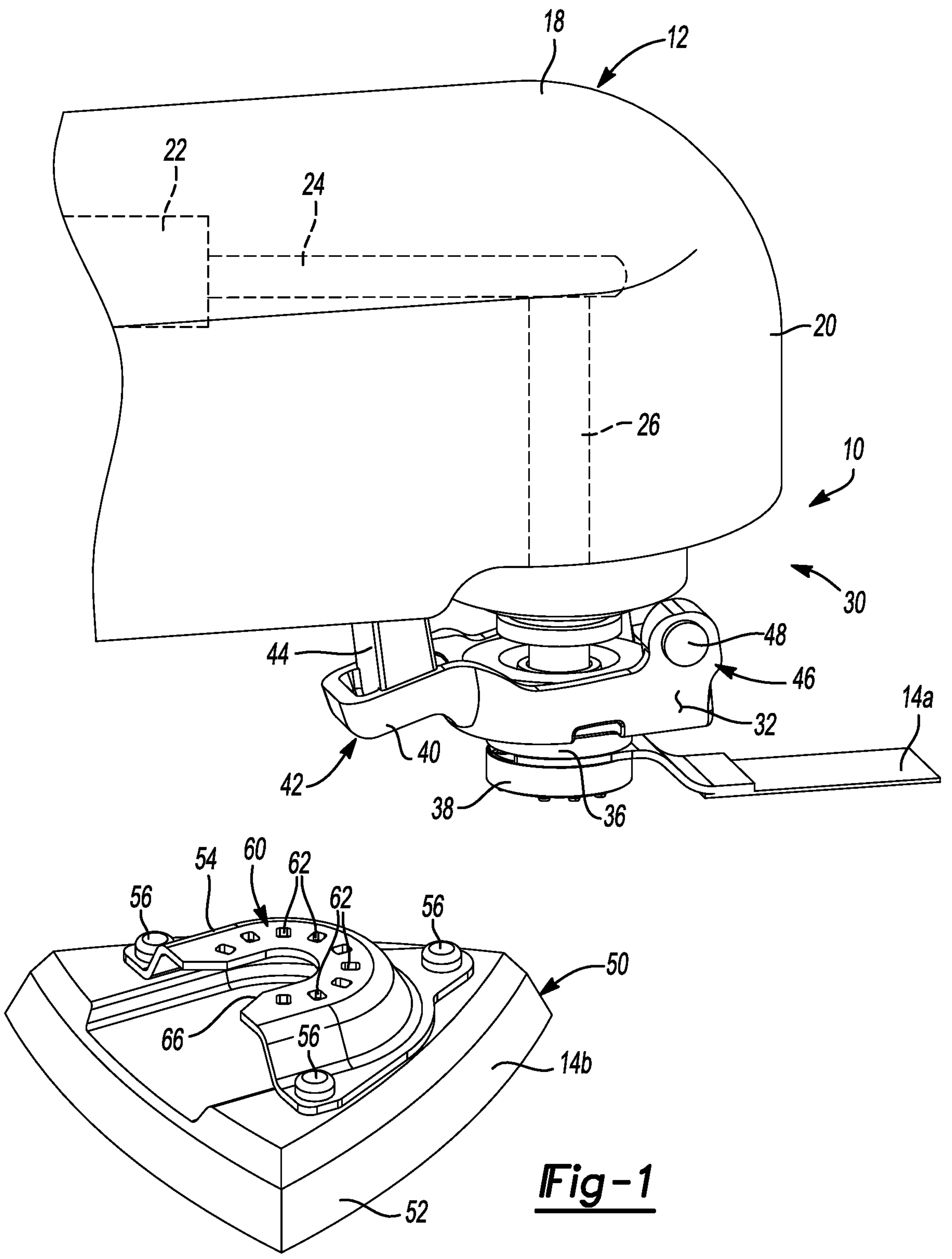
FIG. 1 is a perspective view of a clamp arrangement constructed in accordance to one example of the present teachings and shown operatively associated with an exemplary power hand tool for releasably securing a first or a second accessory.

With initial reference to FIG. 1, a clamp arrangement constructed in accordance to one example of the present disclosure is shown and generally identified at reference numeral 10. The clamp arrangement 10 is shown operatively associated with a power tool 12 for selectively and alternatively retaining various accessories, such as a first accessory **14*a* or a second accessory 14*b*. The exemplary power tool can generally include a tool body 18 including a housing 20 that generally contains a motor 22 that drives an output member 24. The output member 24 can be coupled to a spindle 26. The exemplary power tool 12 is configured for providing an oscillating motion onto the spindle 26. It will be appreciated that while the clamp arrangement 10 is disclosed herein as part of an oscillating power hand tool, the clamp arrangement 10** may be also configured for use with other power tools that releasably secure an accessory.

The clamp arrangement 10 can further include a clamp assembly 30 that operatively cooperates with an actuator such as a lever 32. The clamp assembly 30 can generally include a first clamp member 36 and a second clamp member 38. The lever 32 can include a lever arm 40 that includes a user engagement portion 42 and a block 44. The lever 32 can further include a pivot portion 46 having a pivot axle 48.

With continued reference to FIG. 1, the second accessory 14*b* will be briefly described. The second accessory 14*b* can generally include a sanding platen 50 having a platen body 52 and a mounting collar 54. In the example shown, the mounting collar 54 can be coupled to the body 52 by way of a series of fasteners 56. The body 52 can be configured to support an abrasive sheet, such as sand paper and the like as is known in the art. The mounting collar 54 can generally include an upper plate portion 60 having a plurality of mounting features 62. In the example shown, the mounting features 62 are generally in the form of passages formed through the mounting collar 54. The mounting collar 54 can generally include an open-ended aperture or throat 66 configured to accept the spindle 26 in an assembled position as will be described herein.

Figure 2:
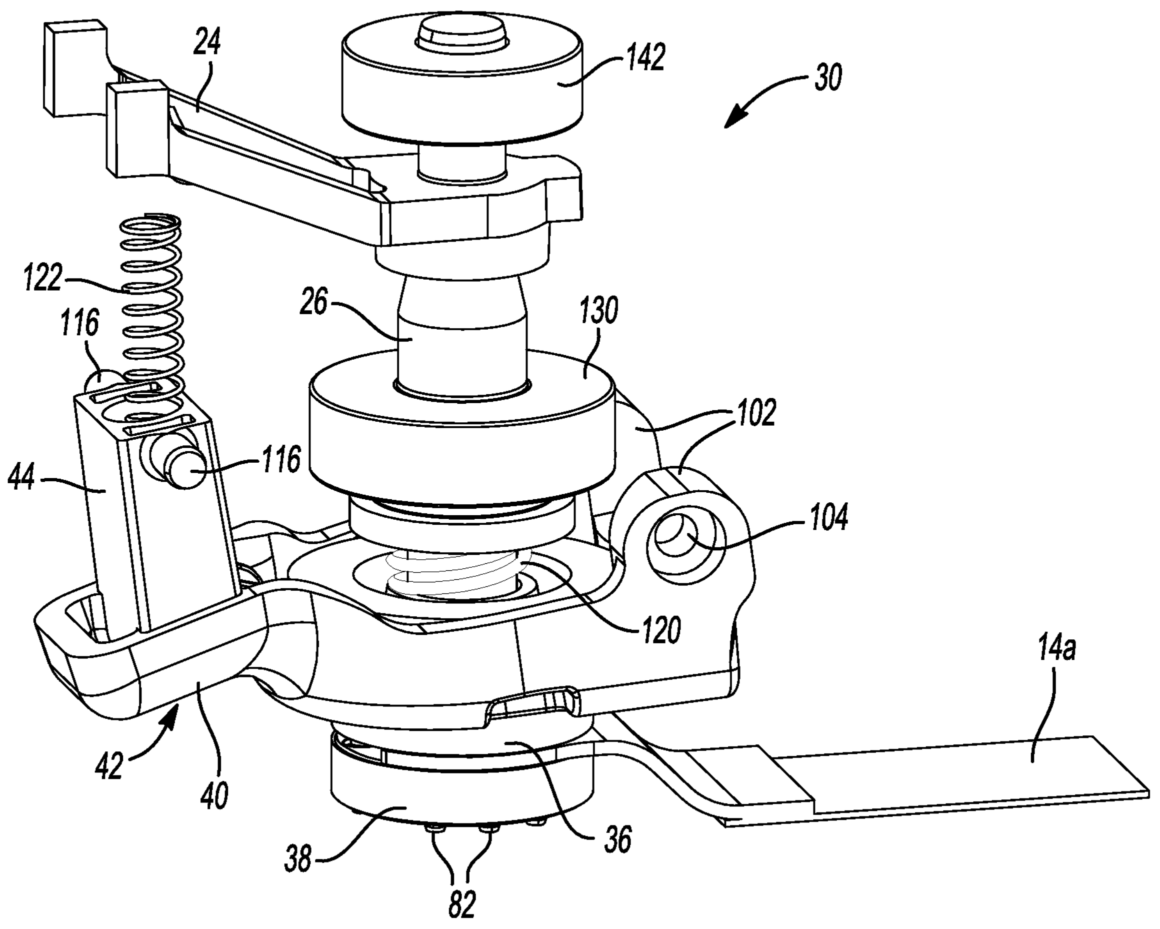
FIG. 2 is a perspective view of a clamp assembly of the clamp arrangement shown in FIG. 1 and shown with the clamp assembly in the closed position retaining the first accessory.

With additional reference now to FIGS. 2 and 3, the clamp assembly 30 will be described in greater detail. The second clamp member 38 can include a second clamp body 70 generally in the form of a ring having a central opening 72. The second clamp body 70 can generally comprise a second clamping surface 74 having a plurality of mounting features 76 formed thereon. In the example shown, the plurality of mounting features 76 are in the form of male protrusions 78. In the particular example shown, eight protrusions each having a tapered shape or form are provided. However, other configurations are contemplated. The second clamp body 70 can additionally include an auxiliary attachment surface 80 having a plurality of auxiliary mounting features 82 (FIG. 2). Again, the plurality of auxiliary mounting features 82 are shown in the form of male protrusions and may include a similar eight protrusion configuration as provided on the second clamping surface 74. The auxiliary mounting features 82 can each have a diameter of 2.4 mm. Other configurations are contemplated.

Figure 3:
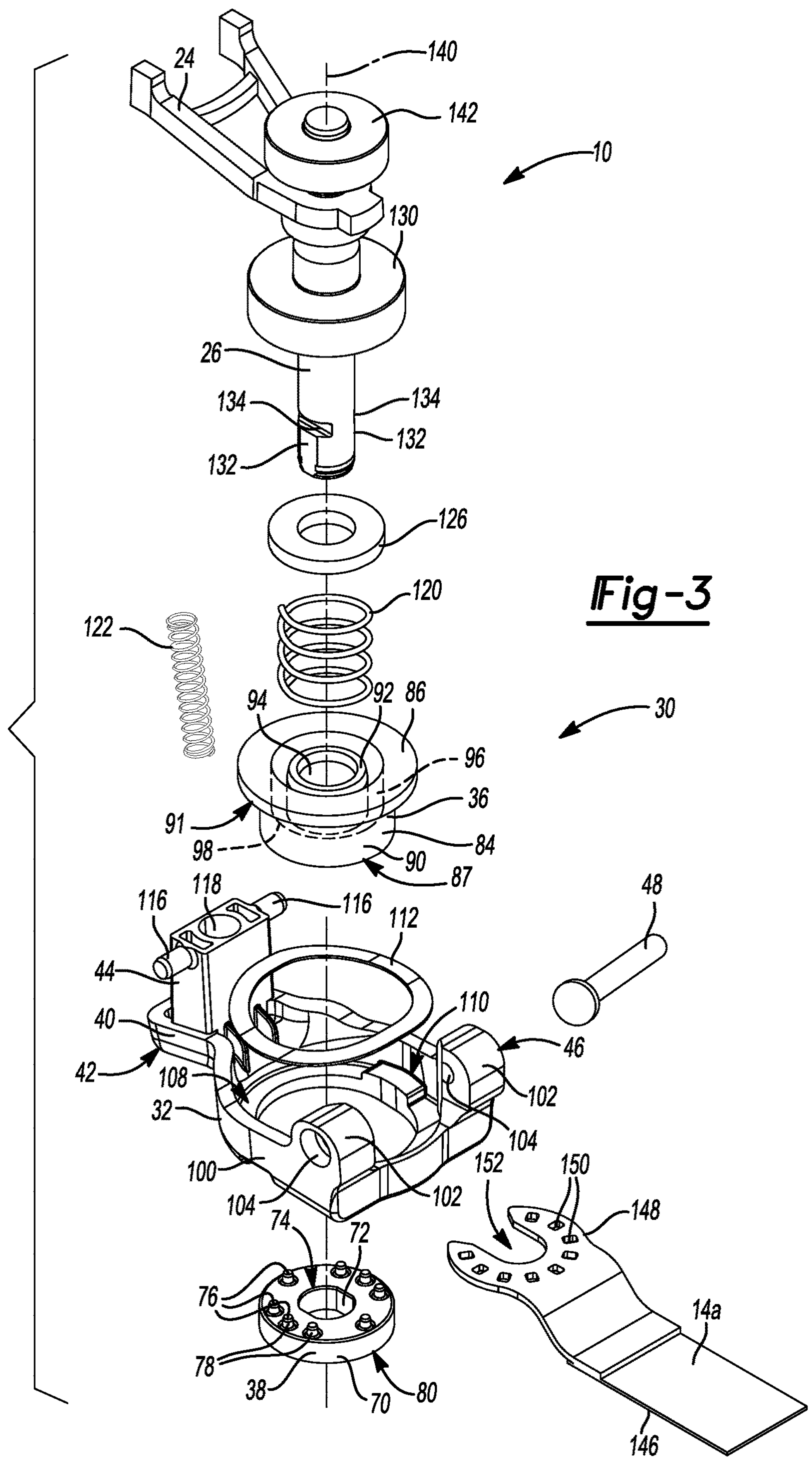
FIG. 3 is an exploded perspective view of the clamp assembly of FIG. 2.
Figure 4:
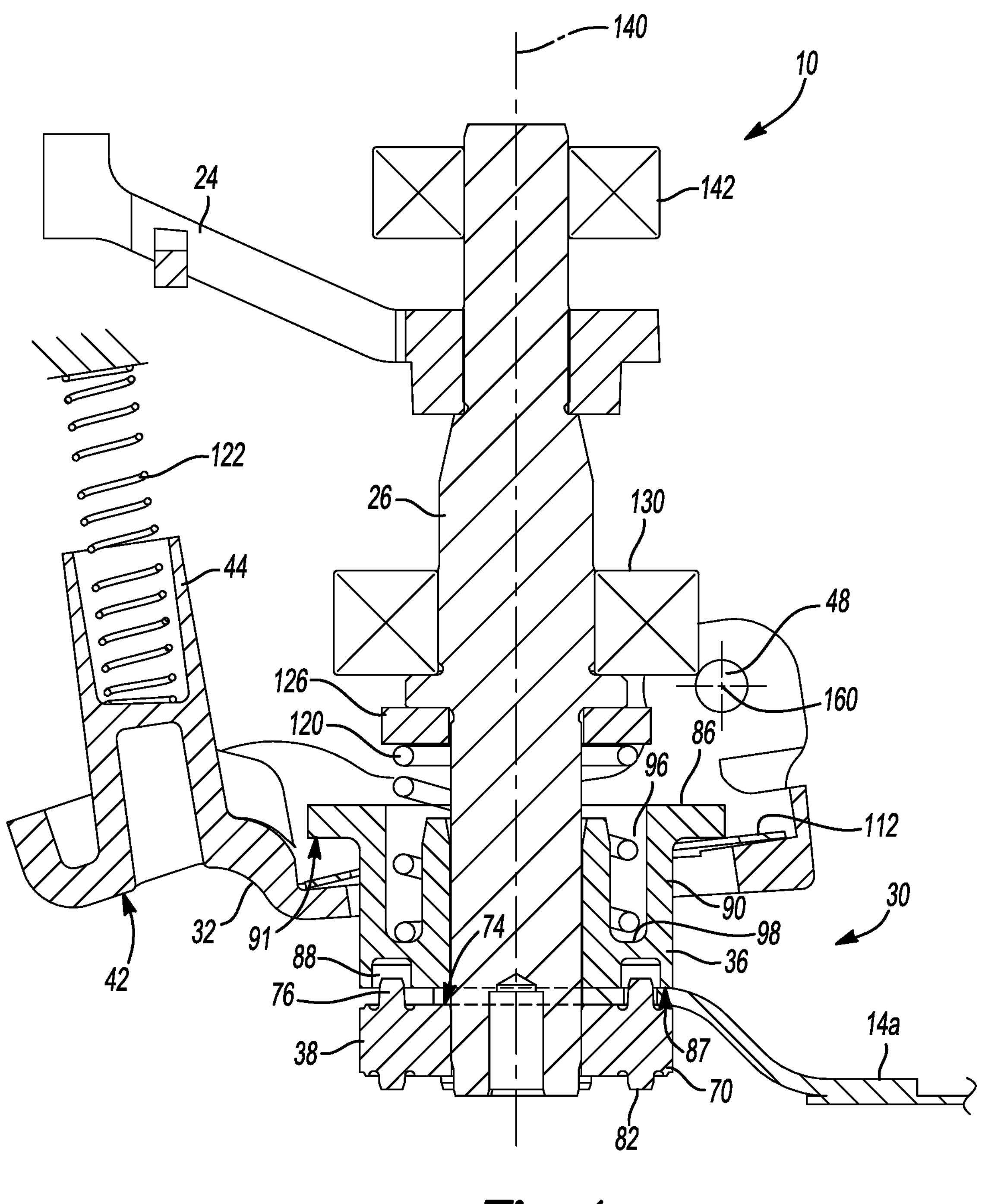
FIG. 4 is a sectional view of the clamp assembly of FIG. 2 and shown with the clamp assembly in the closed position and a lever of the clamp assembly in a first position.

With reference now to FIGS. 3 and 4, the first clamp member 36 can generally include a first clamp member body 84 having an annular flange 86. The first clamp member body 84 can include a first clamping surface 87 having a plurality of mounting features 88 (FIG. 4). In the example shown, the plurality of mounting features 88 are in the form of recesses that cooperatively receive the corresponding plurality of mounting features 76 of the second clamp member 38. The mounting features 88 can have any configuration, such as blind bores, or circular grooves being suitable to accept the male protrusions of the mounting features 76. The annular flange 86 can generally extend radially on an end of an outer hub 90 of the first clamp member body 84. The annular flange 86 can have a lever opposing surface 91. The first clamp member body 84 can further include an inner hub 92 that defines a first clamp member opening 94. The first clamp member opening 94 can be configured to receive the spindle 26. An annular channel 96 can be formed between the outer hub 90 and the inner hub 92. The annular channel 96 can have a terminal surface 98.

The lever 32 can generally include a lever body 100 having the user engagement portion 42 formed generally on a first end and the pivot portion 46 formed on an opposite end. According to one example, the pivot portion 46 can generally include a pair of lobes 102 that each define an axle passage 104. The lever body 100 can further include a pocket 108 having a flange opposing surface 110 for generally receiving two steel balls and the annular flange 86 of the first clamp member 36. The block 44 can generally include a pair of transverse posts 116 and a blind bore 118. The axle passages 104 provided in the lobes 102 can be configured to receive the pivot axle 48.

The clamp arrangement 10 can additionally include a first biasing member 120 and a second biasing member 122. The first biasing member 120 can be at least partially received by the annular channel 96 provided on the first clamp member body 84. The second biasing member 122 can be at least partially received into the blind bore 118 of the block 44. The first biasing member 120 can be generally supported on an upper end by a washer 126 that is correspondingly supported by a bearing 130 journalled around the spindle 26. The spindle 26 can additionally include a pair of flats 132 and channels 134 formed on a distal end. The flats 132 can generally correspond to the profile of the opening 72 formed in the second clamp member 38. The flats 132 can cooperate with the profile of the opening 72 to key the second clamp member 38 to the spindle 26 and inhibit rotation of the second clamp member 38 around a spindle axis 140. In the example provided, the output member 24 can be generally in the form of a drive fork that can impart rotational motion onto the spindle 26 around the spindle axis 140. Other configurations are contemplated. A support bearing 142 can be arranged on one end of the spindle 26 for cooperatively mounting within the housing 20.

Returning to FIG. 3, the first accessory 14*a* can be generally in the form of a cutting member having a working portion 146 and an attachment portion 148. The attachment portion 148 can include a plurality of mounting features 150 in the form of passages formed through the first accessory 14*a*. The attachment portion 148 can further include an open-ended aperture or throat 152 for selectively receiving a portion of the spindle 26 in an assembled position as will be described herein.

With specific reference now to FIGS. 4-6, an exemplary sequence of removing the first accessory 14*a* from the clamp assembly 30 will be described according to one example of the present teachings. With initial reference to FIG. 4, the clamp assembly 30 is shown in a closed position wherein the biasing member 120 is supported on a first end by the washer 126 and provides a downward biasing force onto the first clamp member 36 at the annular channel 96. It is important to recognize that in the particular example shown, the second clamp member 38 is fixed to the spindle 26. As shown, the male protrusions of the mounting features 76 selectively locate into the recesses of the mounting features 88 formed on the first clamp member 36. The first accessory 14*a* therefore is clamped between the second clamping surface 74 and the first clamping surface 87 while the male protrusions of the mounting features 76 locate through passages of the mounting features 150 formed on the first accessory 14*a*. Those skilled in the art will recognize that while some of the mounting features are described and shown as male protrusions and some of the mounting features are described and shown as recesses, the locations may be swapped. Moreover, other interlocking geometries may be used. As viewed in FIG. 4, the lever 32 is shown and generally described herein as the first position.

Figure 5:
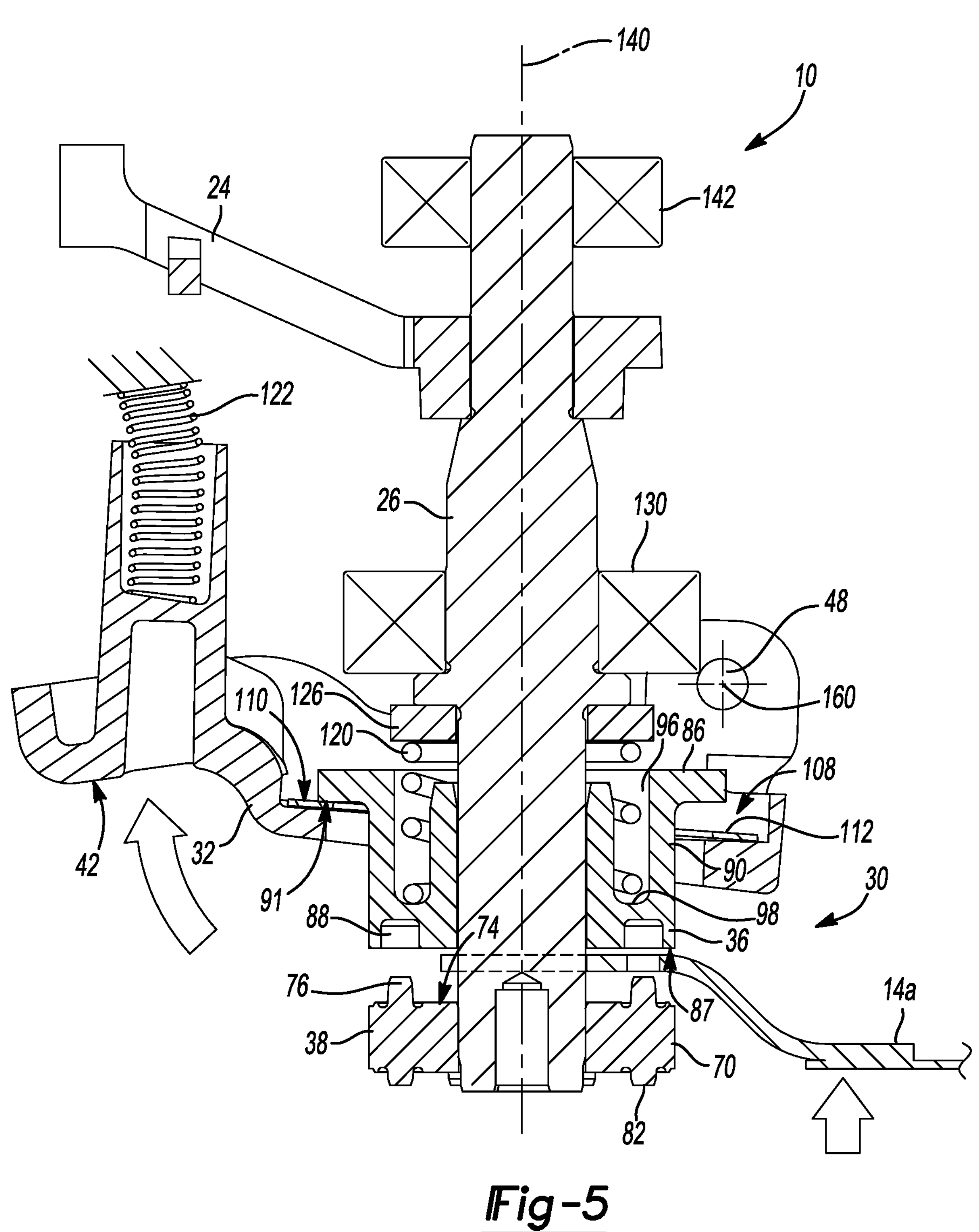
FIG. 5 is a cross-sectional view of the clamp assembly of FIG. 4 and shown with the clamp assembly in the open position resulting from the lever being rotated about a pivot axle into a second position wherein the first accessory is subsequently lifted out of engagement with the first clamp member.
Figure 6:
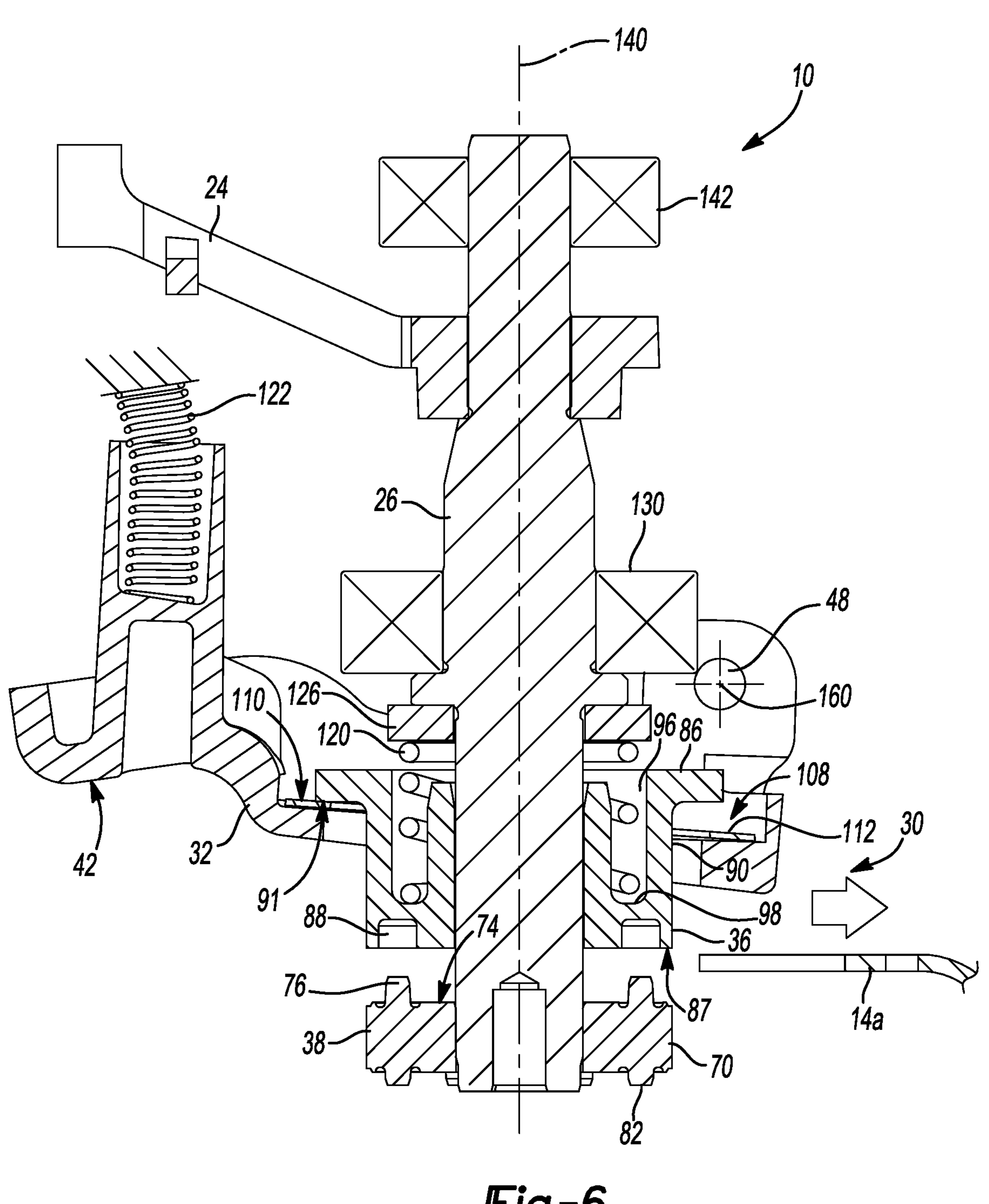
FIG. 6 is a cross-sectional view of the clamp assembly of FIG. 5 shown with the clamp assembly in the open position and the lever in the second position and illustrating the first accessory being removed from the clamp assembly.

With specific reference now to FIG. 5, the lever 32 is shown rotated around a pivot axle axis 160 of the pivot axle 48 to a second position. In the second position, the clamp assembly 30 is generally in the open position where the first clamp member 36 is displaced or offset relative to the second clamp member 38. In order to move the lever 32 from the first position (FIG. 4) to the second position (FIG. 5), a user can urge the user engagement portion 42 (such as by pulling the user engagement portion 42 with an index finger) in a direction generally upwardly as viewed in FIG. 5 and toward the housing 20. In order to rotate the lever 32 around the pivot axle 48, a user must overcome the biasing forces of the respective first and second biasing members 120 and 122. During rotation of the lever 32 around the pivot axle 48, the flange opposing surface 110 in the pocket 108 of the lever body 100 (FIG. 3) generally transmits an upward force (in a direction against the biasing force of the first biasing member 120) onto the lever opposing surface 91. In this regard, the lever 32 can generally lift the first clamp member 36 at the annular flange 86 to move the first clamping surface 87 away from the second clamping surface 74. It will be appreciated that other mechanical configurations other than a lever that pivots about a pivot axle may be used. For example, a camming configuration or slidable actuation member may be additionally or alternatively employed.

With the clamp assembly 30 in the open position, the first and second clamp members 36 and 38, respectively, provide enough clearance, such that a user can remove the first accessory 14*a* away from the clamp assembly 30. In one example, it may be necessary to initially lift the first accessory 14*a* away from the male protrusions of the mounting features 76 before pulling the first accessory 14*a* away from the clamp assembly 30 (FIG. 6).

The clamp arrangement 10 of the present disclosure can provide a significant mechanical advantage that can provide a particularly robust clamping action onto an accessory in a tight package requiring relatively small space. In this regard, by mounting the pivot axle 48 on an opposite end of the user engagement portion 42 a user is offered a significant moment arm that can act against the respective biasing forces of the first and second biasing members 120 and 122 while still offering a significant clamping force. According to other advantages, the location of the user engagement portion 42 provides an ergonomically pleasing configuration adjacent to the housing 20 where a user's palm would be generally positioned. In this regard, an index finger can easily negotiate onto the user engagement portion 42 without having to significantly reposition a user's palm. Moreover, the user engagement portion 42 can be generally located between the housing 20 and the first accessory 14*a*, such that a user can easily pull up on the user engagement portion 42 in a direction toward the housing with one hand while removing/installing any given accessory with the other hand.

Figures 7, 8, 9:
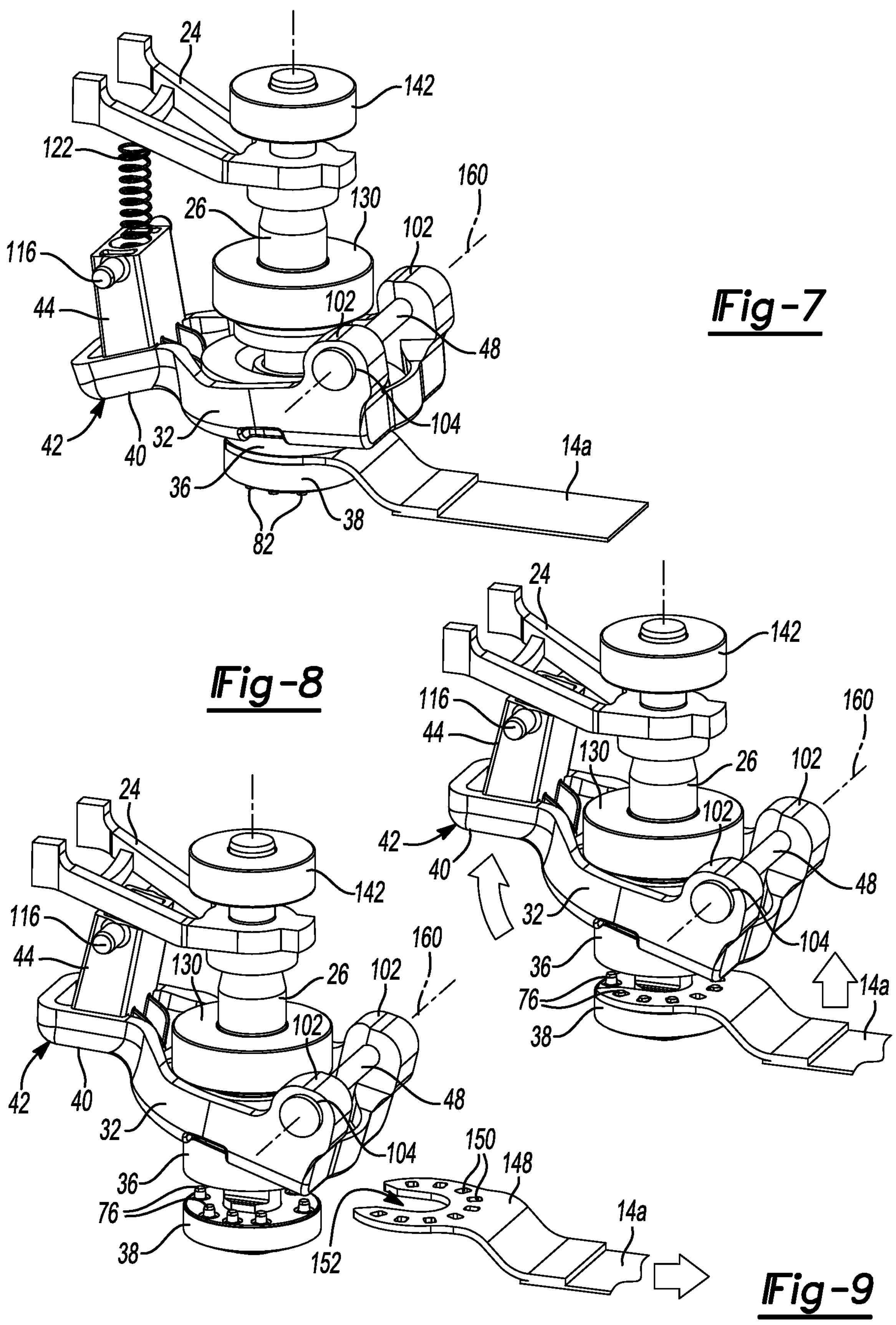
FIGS. 7-9 are perspective views of the clamp assembly that generally correspond to the sequence illustrated in FIGS. 4-6 for removing the first accessory from the clamp assembly.

With specific reference now to FIGS. 7-9, perspective views of the clamp assembly 30 are shown wherein FIG. 7 generally corresponds to the sectional view of FIG. 4 of the clamp assembly 30 in the closed position and the lever 32 in the first position. FIG. 8 generally corresponds to the sectional view of FIG. 5 where the clamp assembly 30 is in the open position and the lever 32 is in the second position. FIG. 9 generally corresponds to the sectional view of FIG. 6 where the clamp assembly 30 is in the open position and the lever 32 is in the second position while the first accessory 14*a* is removed from the clamp assembly 30.

Figures 10, 11, 12:
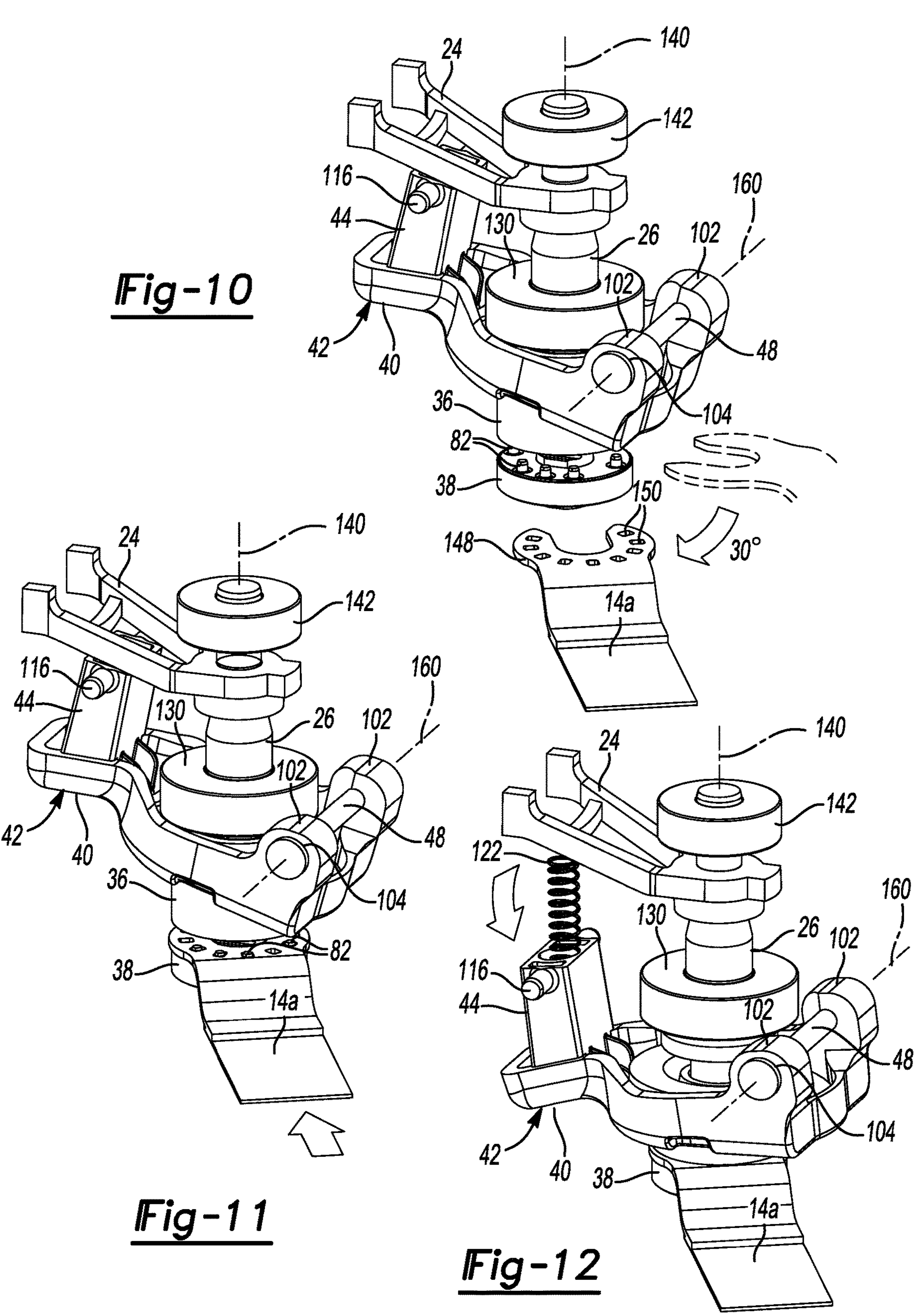
FIGS. 10-12 are perspective views of the clamp assembly that illustrate an exemplary sequence of orienting the first accessory in a different rotational position relative to the clamp assembly.
Figure 16:
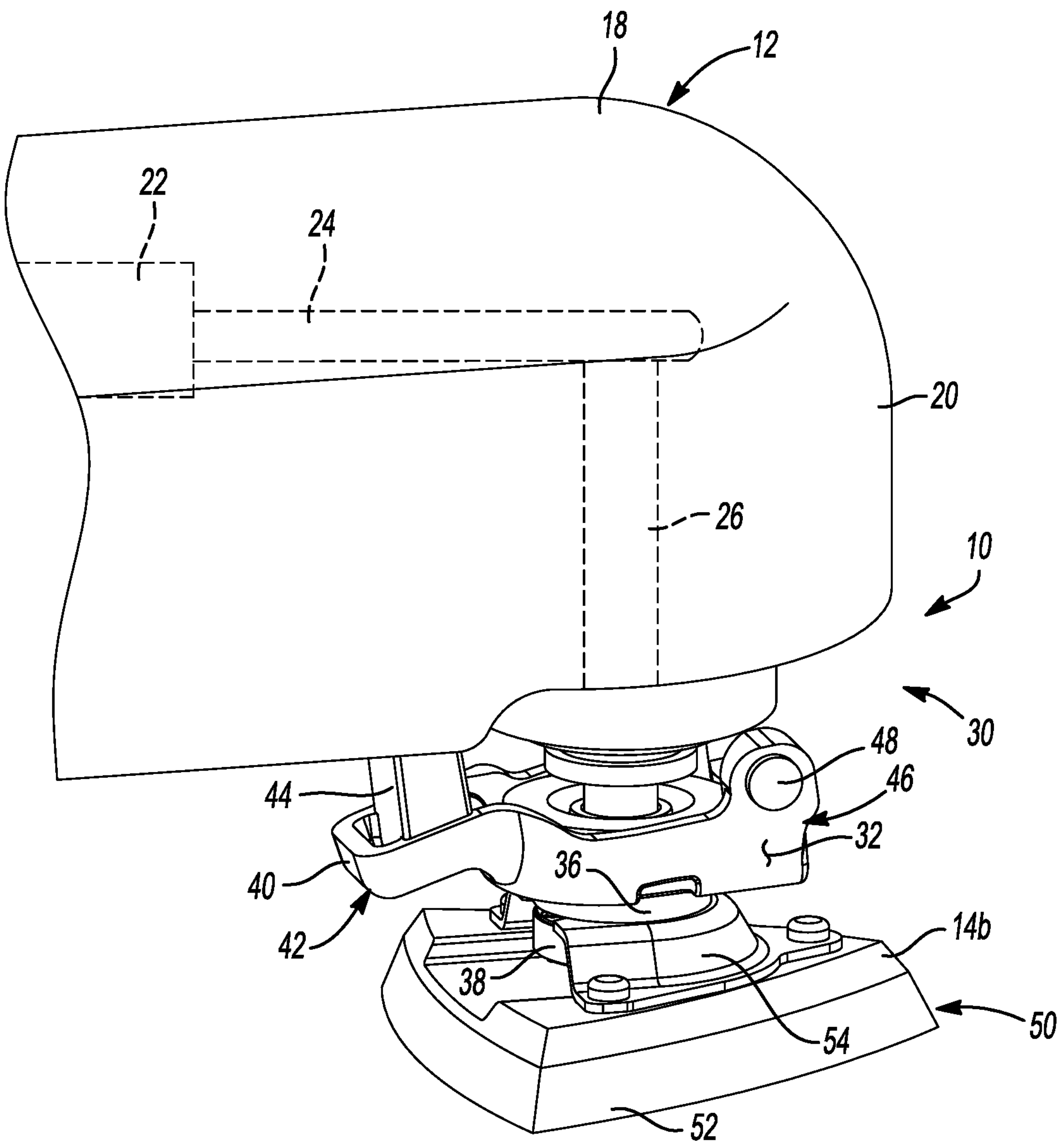
FIG. 16 is a perspective view of the clamp arrangement of the present teachings and shown with the clamp assembly secured to the second accessory.
Figure 17:
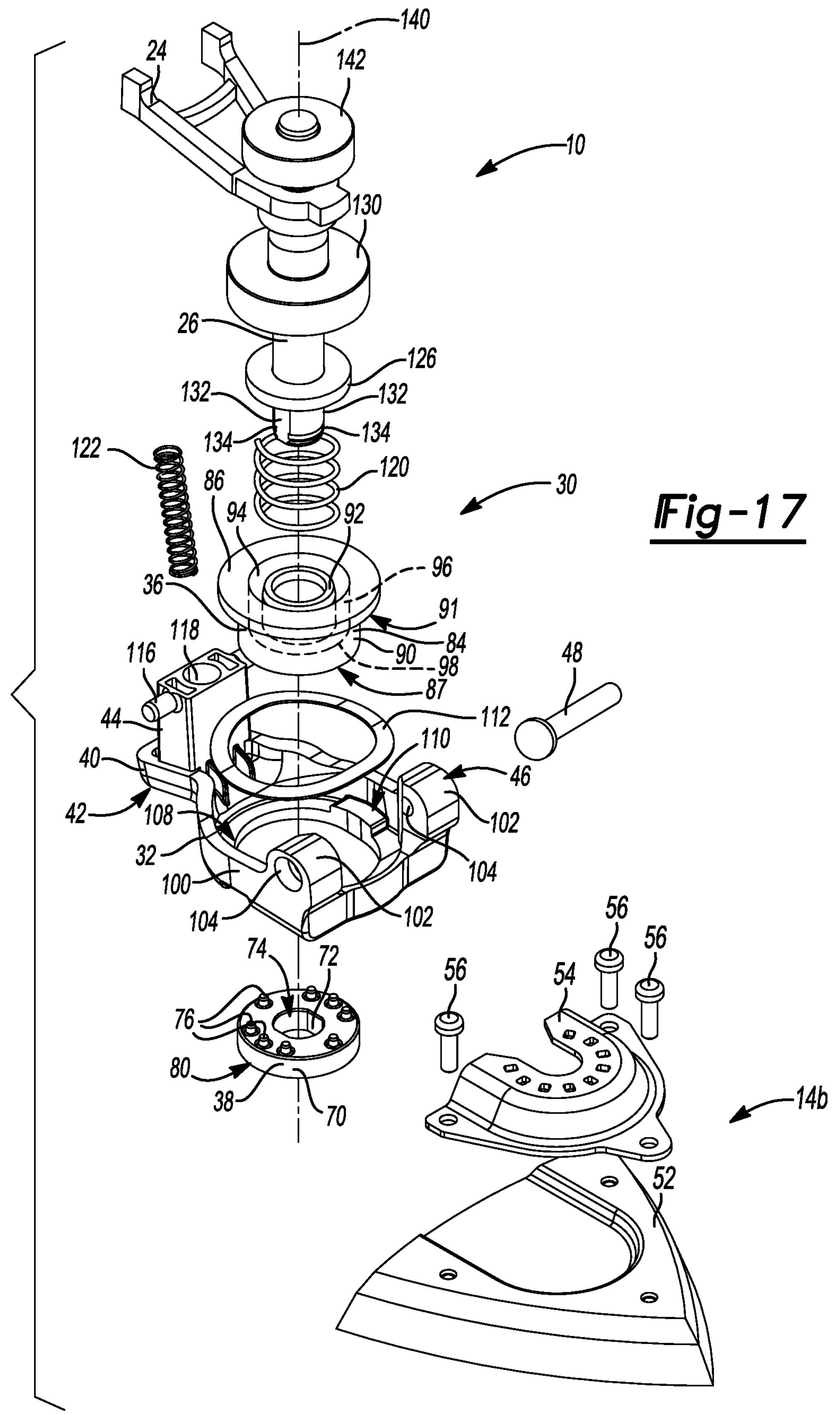
FIG. 17 is an exploded perspective view of the clamp assembly and second accessory illustrated in FIG. 16.

With reference now to FIGS. 10-12, the clamp assembly 30 can be used to selectively clamp a given accessory, such as the first accessory 14*a* through a variety of rotational orientations around the spindle axis 140. As identified above, the second clamp member 38 includes eight mounting features 76 however other configurations may be incorporated. The first accessory 14*a* includes nine mounting features or passages 150. The first accessory 14*a* can be arranged in a plurality of different rotational orientations, such that the male protrusions 78 can be aligned for passing through the passages 150 by rotating the first accessory 14*a* into the orientation desired. As can be appreciated, it may be advantageous to orient the first accessory 14*a* differently for a particular task. Once the passages 150 are aligned for receipt of the male protrusions 78 on the second clamp member 38 the attachment portion 148 of first accessory is dropped onto the second clamping surface 74.

In the exemplary sequence shown in FIGS. 10-12, a user can initially pull up the lever 32 at the user engagement portion 42 causing the annular flange 86 of the first clamp member 36 to be lifted as previously described. With the first clamp member 36 displaced from the second clamp member 38, the first accessory 14*a* can be oriented into the desired radial position and aligned with the corresponding male protrusions 78. The user can then release the user engagement portion 42 allowing the first biasing member 120 (and the second biasing member 122) to urge the first clamp member 36 in a direction toward the second clamp member 38 until the respective first and second clamping surfaces 87 and 74, respectively, engage and clamp the attachment portion 148 of the first accessory 14*a* (FIG. 12).

Turning now to FIGS. 13-15, various examples are shown with the first accessory 14*a* mounted around the second clamp member 38. In the examples shown, the male protrusions of the mounting features 76 can be arranged to allow the first accessory 14*a* to be indexed at about thirty degree increments around the second clamping surface 74. When describing the male protrusions of the mounting features 76 in the context of a clock, mounting features are absent at the two, four, eight and ten o'clock positions. Other examples are contemplated.

Figure 18:
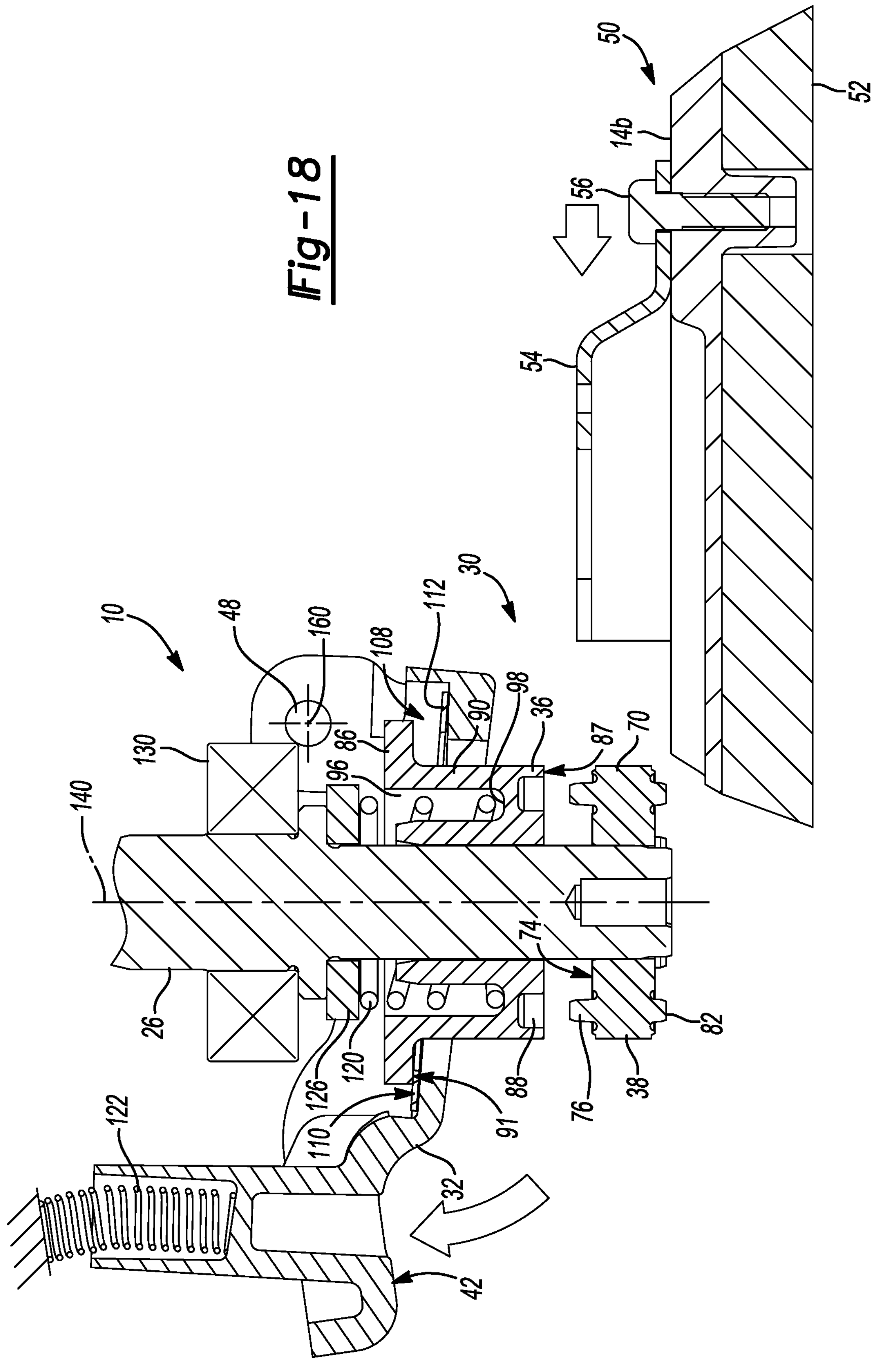
FIG. 18 is a sectional view of the clamp assembly of FIG. 16 and shown with the clamp assembly in the open position resulting from movement of the lever around the pivot axle to the second position for receipt of a mounting collar of the second accessory.

With reference now to FIGS. 16-20, the clamp assembly 30 will be described clamping the second accessory 14*b* according to one example of the present teachings. As described above, the clamp assembly 30 is normally biased into the closed position. As illustrated in FIG. 18, the lever 32 is shown rotated around the pivot axle axis 160 of the pivot axle 48 to the second position. In the second position, the clamp assembly 30 is generally in the open position where the first clamp member 36 is displaced relative to the second clamp member 38. With the clamp assembly 30 in the open position, the first and second clamp members 36 and 38 respectively provide enough clearance to accept the mounting collar 54 of the second accessory 14*b*.

Figures 19, 20:
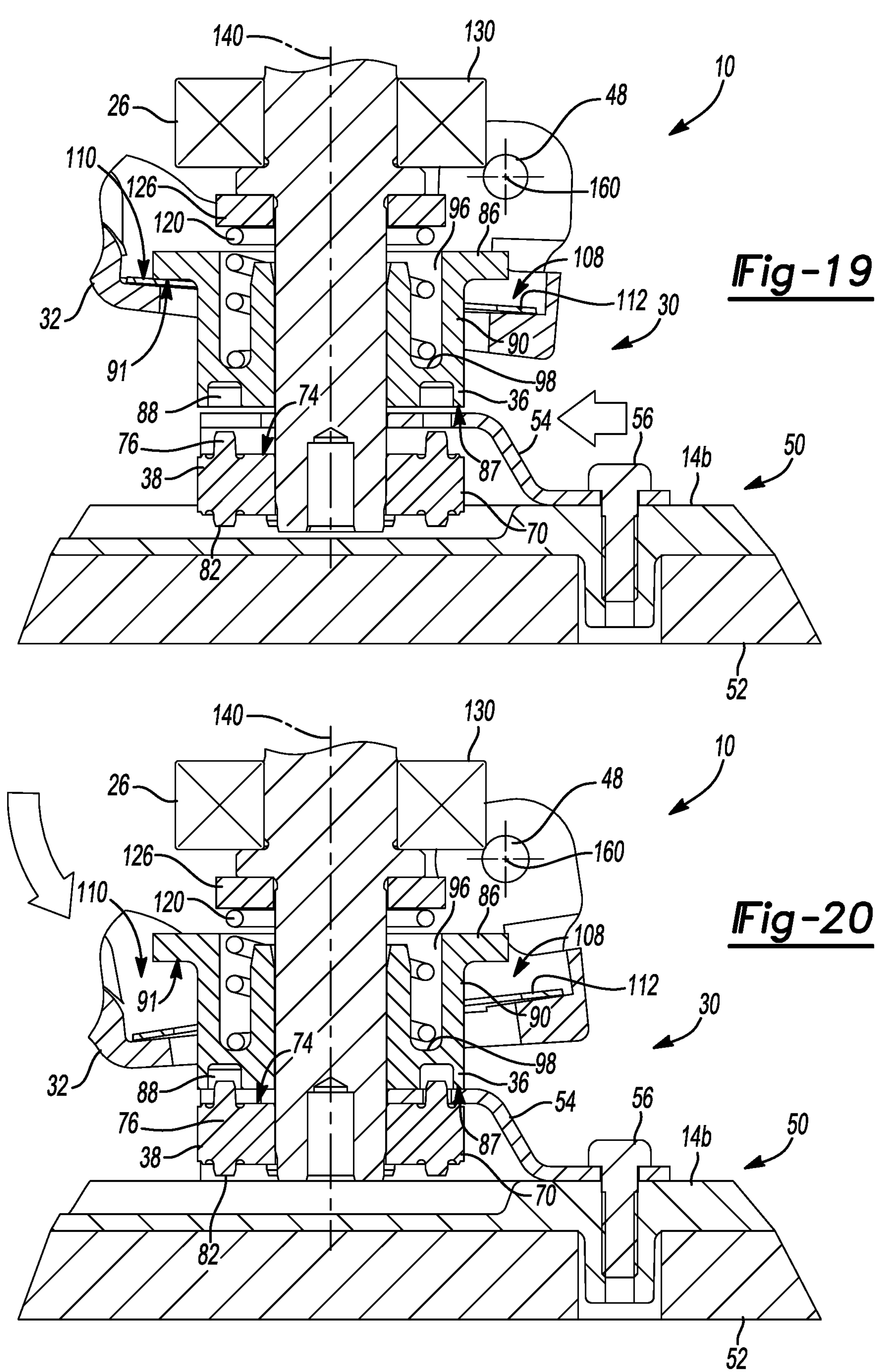
FIG. 19 is a cross-sectional view of the clamp assembly of FIG. 18 and shown with the mounting collar of the second accessory positioned generally between first and second clamp members of the clamp assembly while the lever is maintained in the second position.
FIG. 20 is a cross-sectional view of the clamp assembly of FIG. 19 and illustrating the clamp assembly in the closed position as a result of the lever being released and returned to the first position causing the first and second clamp members to clamp the mounting collar.

While a user maintains an upward force on the user engagement portion 42 of the lever 32, the second accessory 14*b* is directed toward the clamp assembly 30, such that the spindle 26 is generally located through the throat 66 (FIG. 19). Once the desired mounting features 62 of the mounting collar 54 are aligned with the desired mounting features 76 of the second clamp member 38, the user can release the user engagement portion 42 of the lever 32 allowing the respective first and second biasing members 120 and 122 to return the lever 32 to the first position (FIG. 20). In the first position, the clamp assembly 30 is in the closed position, such that the first clamping surface 87 of the first clamp member 36 as well as the second clamping surface 74 of the second clamp member 38 cooperatively clamp the mounting collar 54 of the second accessory 14*b*.

Figure 21:
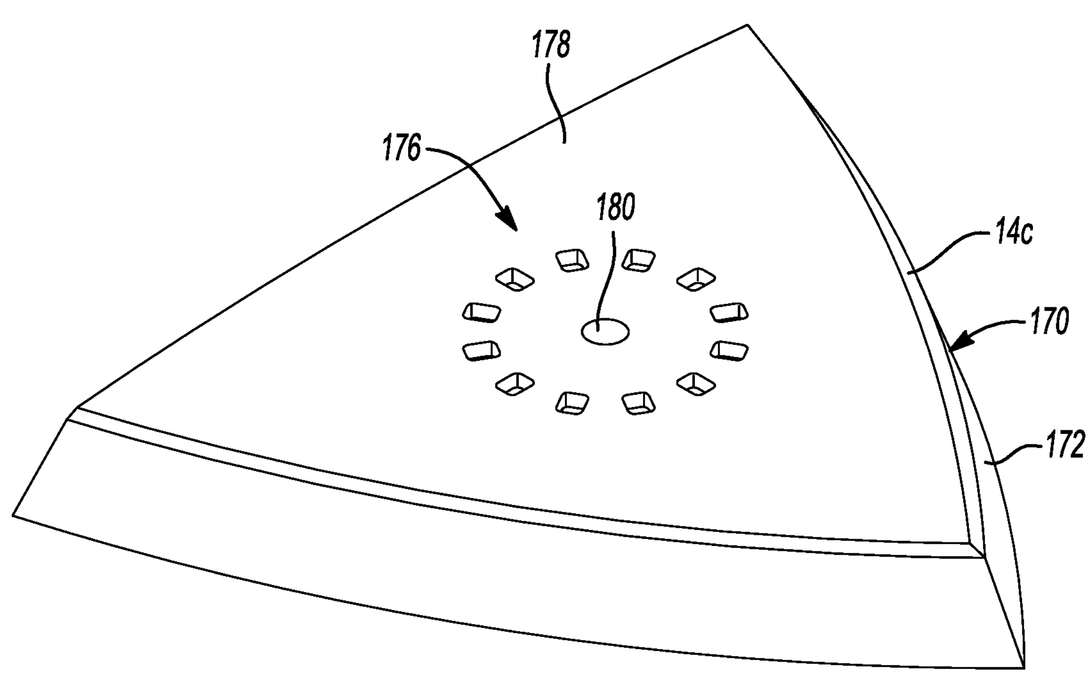
FIG. 21 is a perspective view of an exemplary third accessory.
Figure 22:
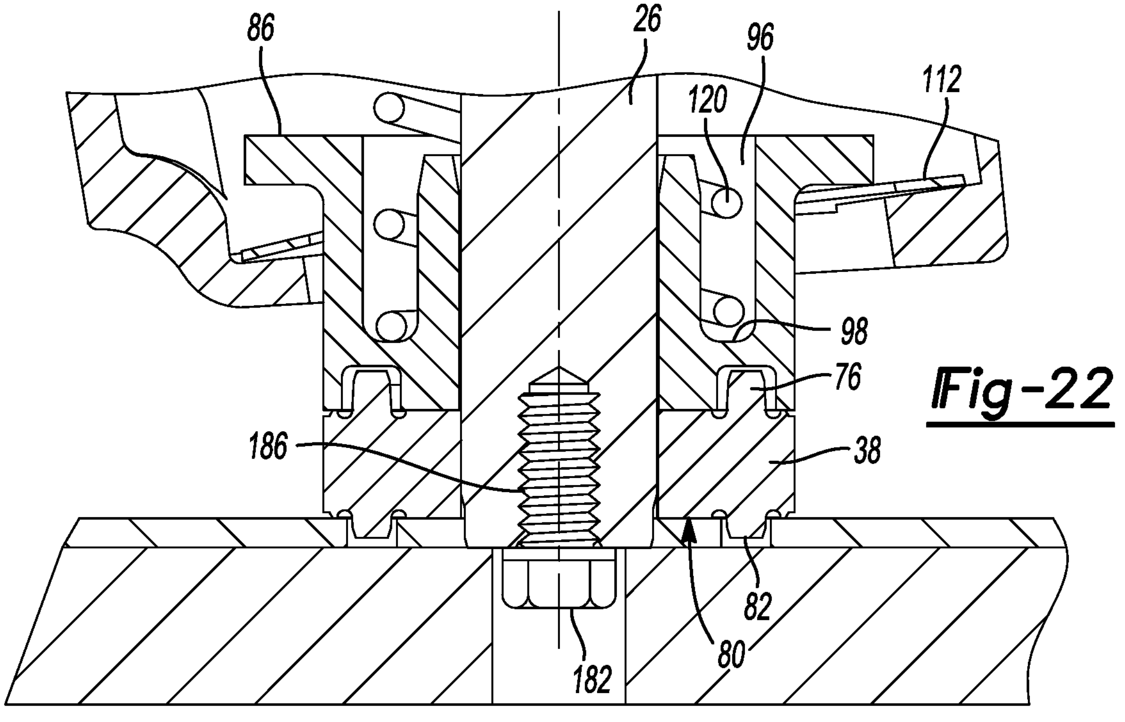
FIG. 22 is a partial cross-section of the clamp assembly and shown with the third accessory secured to an auxiliary mounting surface of the second clamp member.
Figures 23, 24:
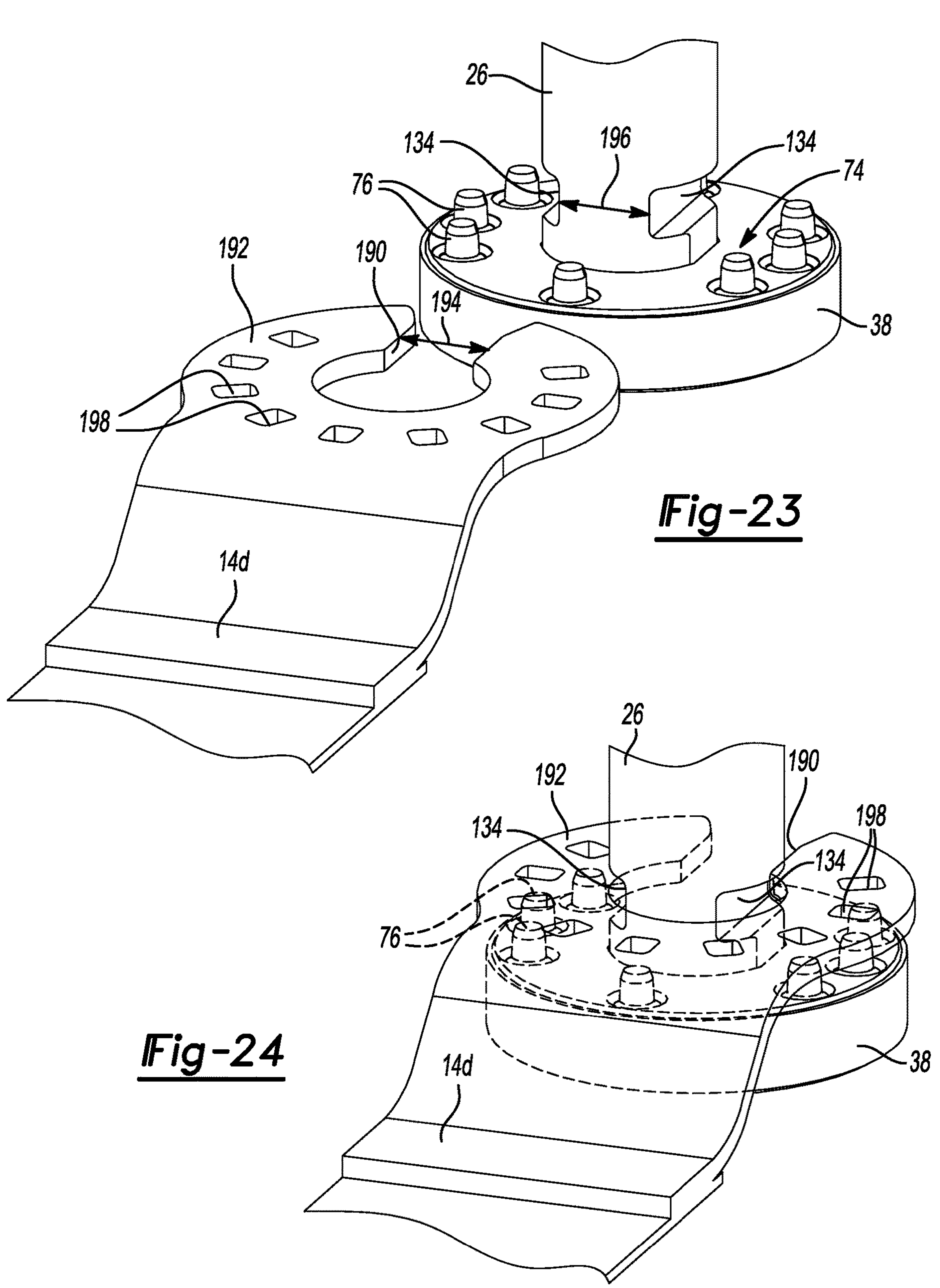
FIGS. 23-25 illustrate an exemplary assembly sequence of a fourth accessory having a throat that defines a relatively narrower opening as compared to the first accessory wherein the throat is slidably directed through channels provided on the spindle.

Turning now to FIGS. 21 and 22, a third accessory 14*c* and a method of attaching the third accessory 14*c* to the auxiliary attachment surface 80 of the second clamp member 38 will be described. The third accessory 14*c* can generally include an iron-shaped member 170. A plurality of mounting features 176 can be formed around an upper surface 178 of a body 172 of the third accessory 14*c*. In the example shown, the plurality of mounting features 176 can be in the form of recesses having a profile that generally mates with the plurality of mounting features 82 extending from the auxiliary attachment surface 80. A mounting aperture 180 can be formed through the body 172 of the third accessory 14*c* for accepting a fastener 182 (FIG. 22). The fastener 182 can threadably mate with a threaded bore 186 defined at a distal end of the spindle 26. Those skilled in the art will readily appreciate that movement of the lever 32 will not affect the attachment of the third accessory 14*c* as the third accessory 14*c* only interfaces with the second clamp member 38 that is rigidly fixed to the spindle 26.

Turning now to FIGS. 23-26, a fourth accessory 14*d* will be described cooperating with the spindle 26 and the second clamp member 38. The channels 134 formed in the spindle 26 can provide clearance for accepting other accessories, such as accessories that may define a throat 152 having a smaller entrance. In this regard, the reduced geometry throat of an accessory may be initially negotiated through the channel 134 prior to rotating the accessory into the desired orientation relative to the spindle 26 and subsequently clamping the accessory to the clamp assembly 30.

Figures 25, 26:
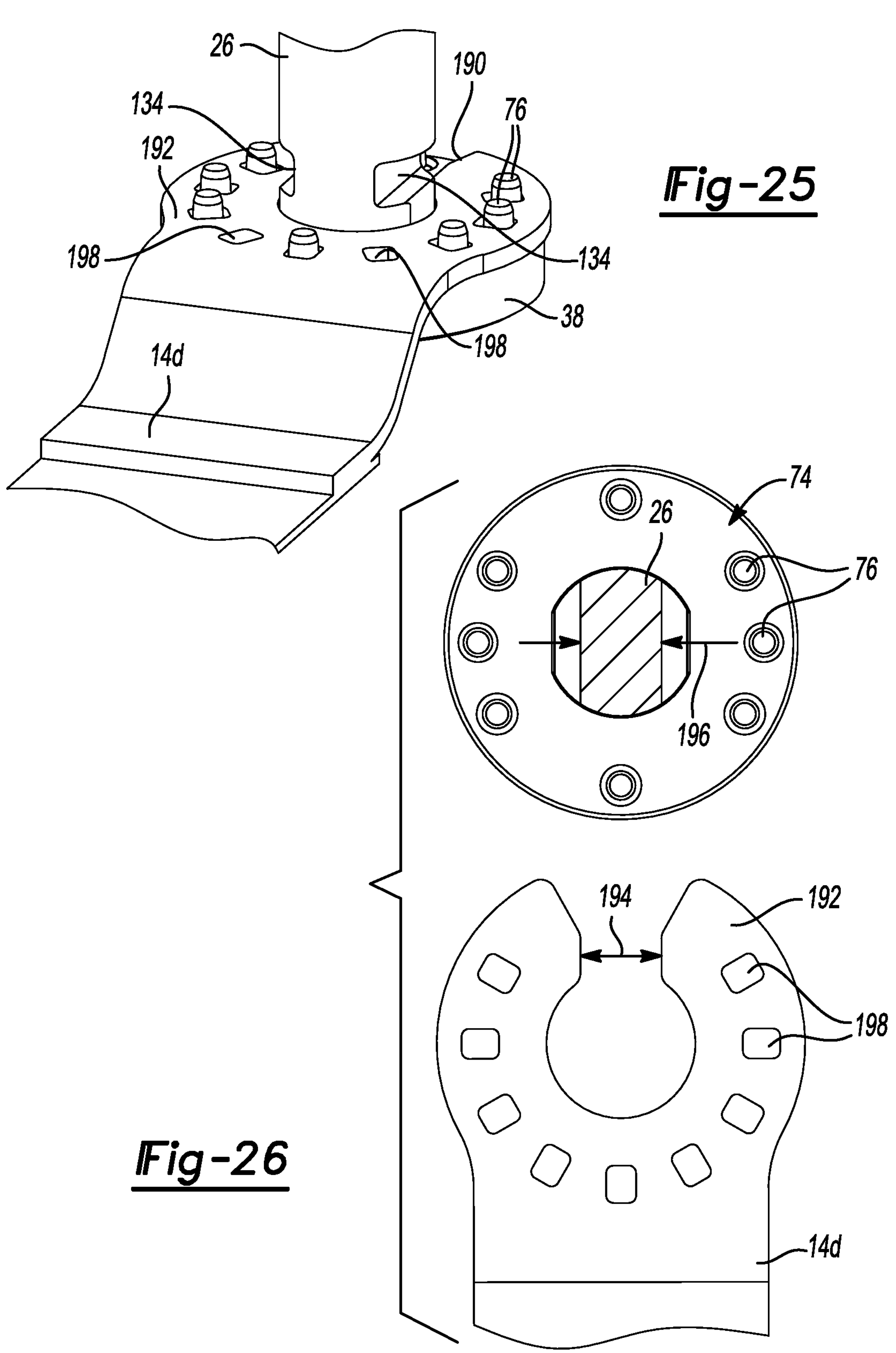
FIG. 26 is an exploded partial plan view of the fourth accessory and shown adjacent to the second clamp member and illustrated with the spindle in cross-section taken through the channels.

The fourth accessory 14*d* can have an open-ended aperture or throat 190 formed on an attachment portion 192. The throat 190 can generally span a distance 194. As compared to the throat 152 on the first accessory 14*a*, the throat 190 provides a reduced distance 194. The channels 134 provided on the spindle 26 are offset a distance 196 that is generally less than the distance 194, such that the throat 190 can be advanced through the channels 134 until clearing the channels 134 at an opposite end of the spindle 26 (see FIG. 24). Once the throat 190 has cleared the channels 134, a user can rotate the fourth accessory 14*d* to a desired orientation around the second clamping surface 74 of the second clamp member 38. Once the desired orientation has been attained, the attachment portion 192 of the fourth accessory 14*d* can be dropped onto the second clamping surface 74 while the male protrusions of the mounting features 76 locate through respective passages 198 formed through the attachment portion 192 on the fourth accessory 14*d* (FIG. 25). FIG. 26 illustrates a plan view that represents the relative distances 194 of the throat 190 and 196 of the channels 134.

Figure 28:
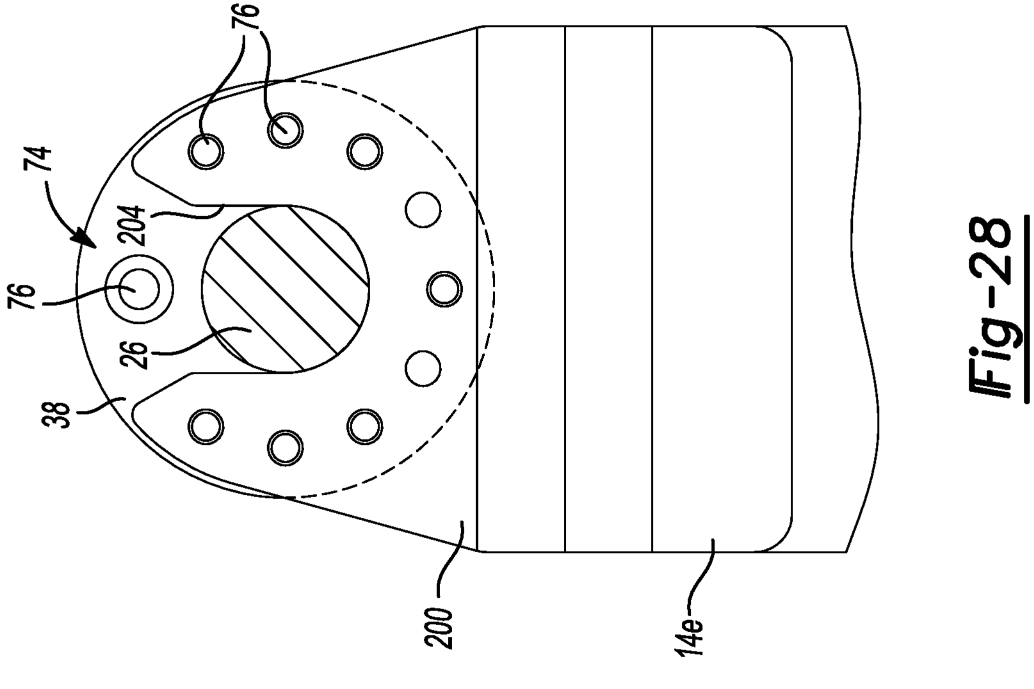
FIG. 28 is a partial plan view of the fifth accessory shown in FIG. 27 and illustrated interfacing with the second clamp member.
Figure 27:
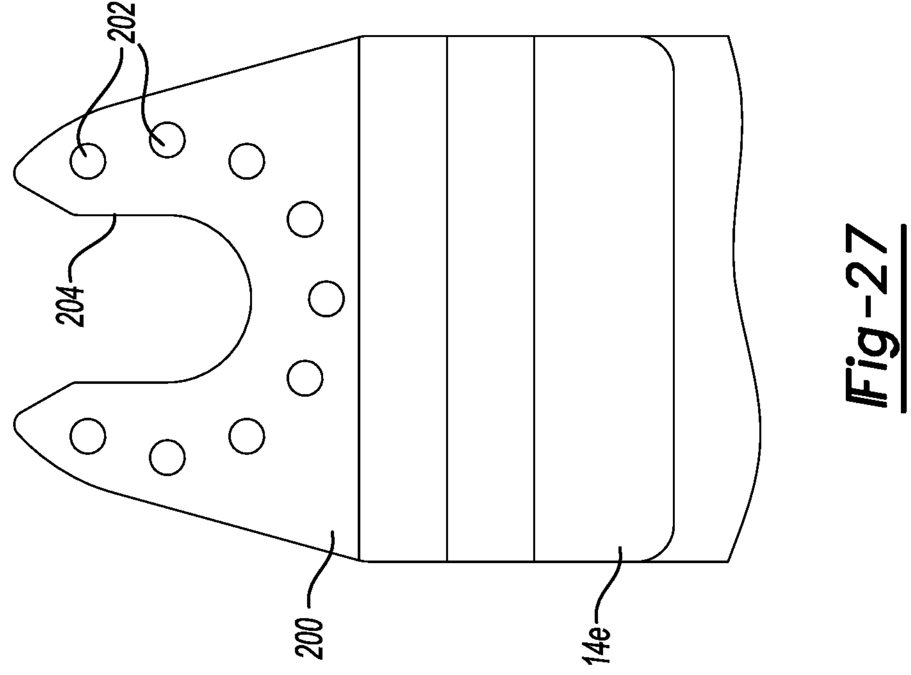
FIG. 27 is a partial plan view of a fifth accessory having circular mounting passages according to additional features.
Figure 29:
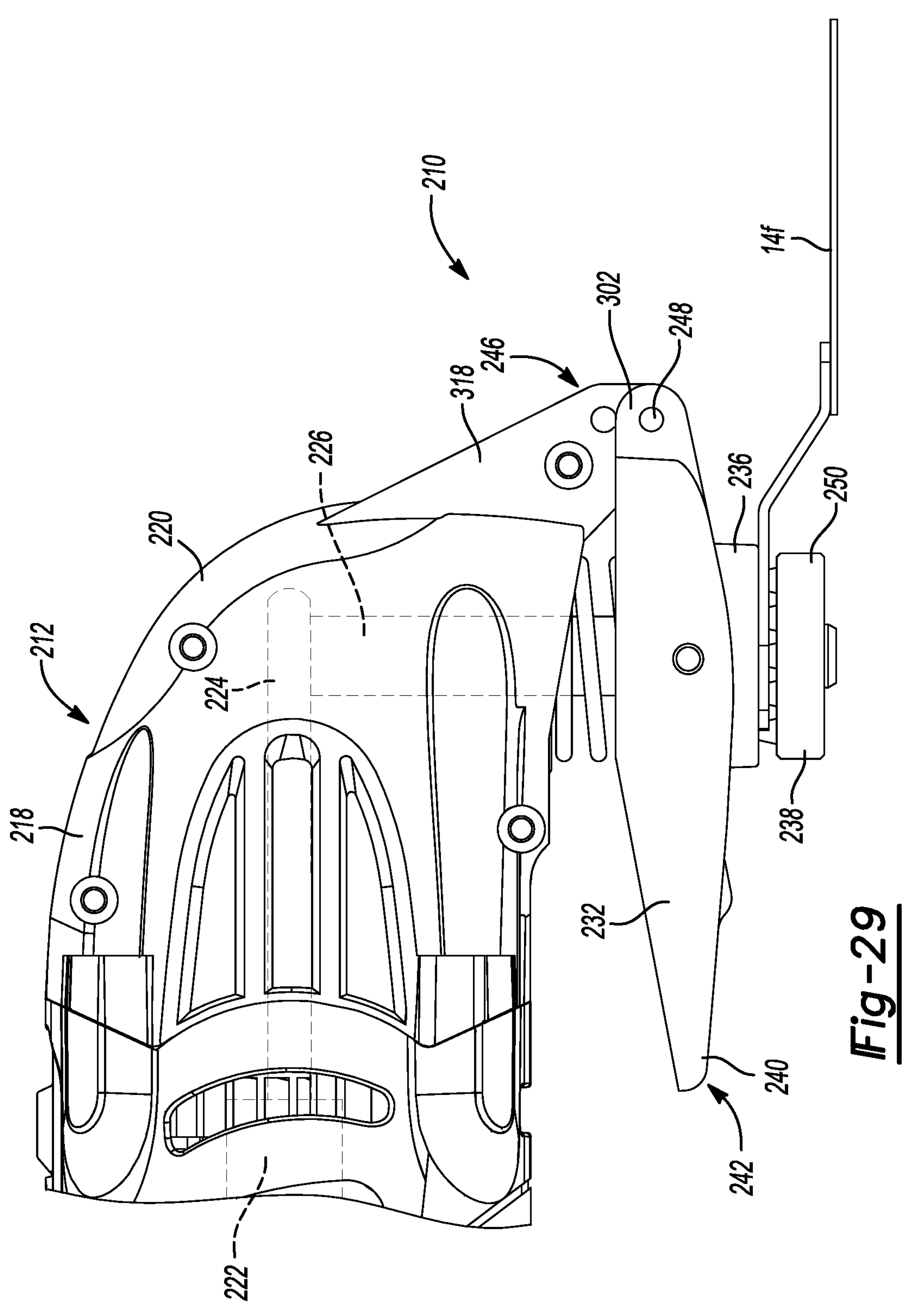
FIG. 29 is a side view of a clamp arrangement constructed in accordance to another example of the present teachings and shown operatively associated with an exemplary hand tool.

With reference now to FIGS. 27 and 28, a fifth accessory 14*e* is shown that has an attachment portion 200 having a plurality of mounting formations 202 formed therethrough. The mounting formations 202 can be generally in the form of circular apertures. The circular apertures can have a tapered shape. Other dimensions are contemplated that may still have a diameter (or opening in general) that is large enough to accept the diameter of the respective mounting features 76 on the second clamp member 38.

With reference now to FIGS. 29-34, a clamp arrangement constructed in accordance to another example of the present disclosure is shown and generally identified at reference numeral 210. The clamp arrangement 210 is shown operatively associated with a power tool 212 for selectively and alternatively retaining various accessories such as a sixth accessory 14*f*. The exemplary power tool 212 can generally include a tool body 218 including a housing 220 that generally contains a motor 222 that drives an output member 224. The output member 224 can be coupled to a spindle 226. The exemplary power tool 212 is configured for providing an oscillating motion onto the spindle 226. As with the clamp arrangement 10 described above, the clamp arrangement 210, while described herein as part of an oscillating hand tool, can also be used with other power tools that releasably secure an accessory.

The clamp arrangement 210 can further include a clamp assembly 230 (FIG. 30) that operatively cooperates with a lever 232. The clamp assembly 230 can generally include a first clamp member 236 and a second clamp member 238. The lever 232 can include a lever arm 240 that includes a user engagement portion 242. The lever 232 can further include a pivot portion 246 having a pivot axle 248.

Figure 30:
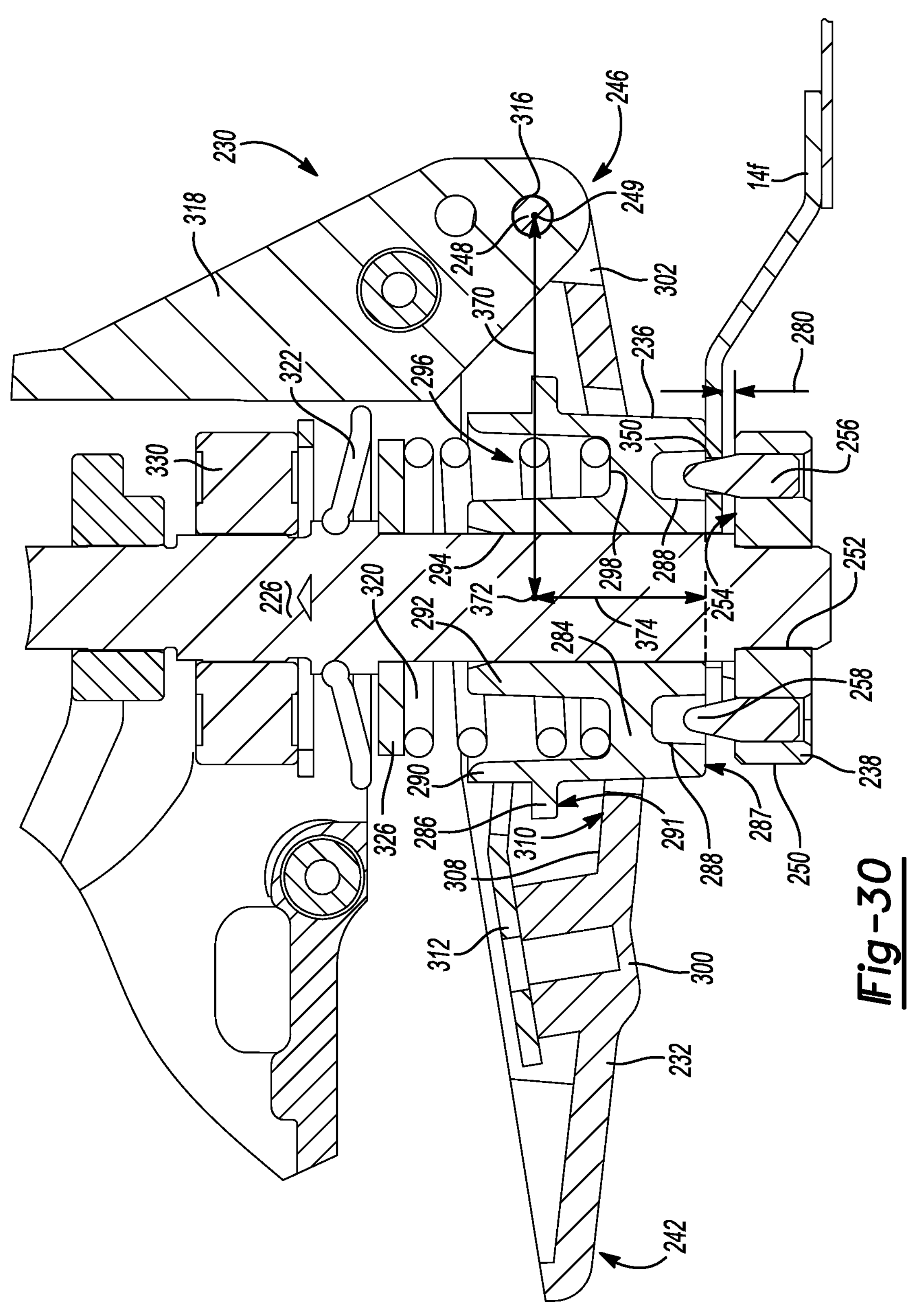
FIG. 30 is a sectional view of the clamp assembly of FIG. 29 and shown with the clamp assembly in a closed position and a lever of the clamp assembly in a first position.
Figures 31, 32:
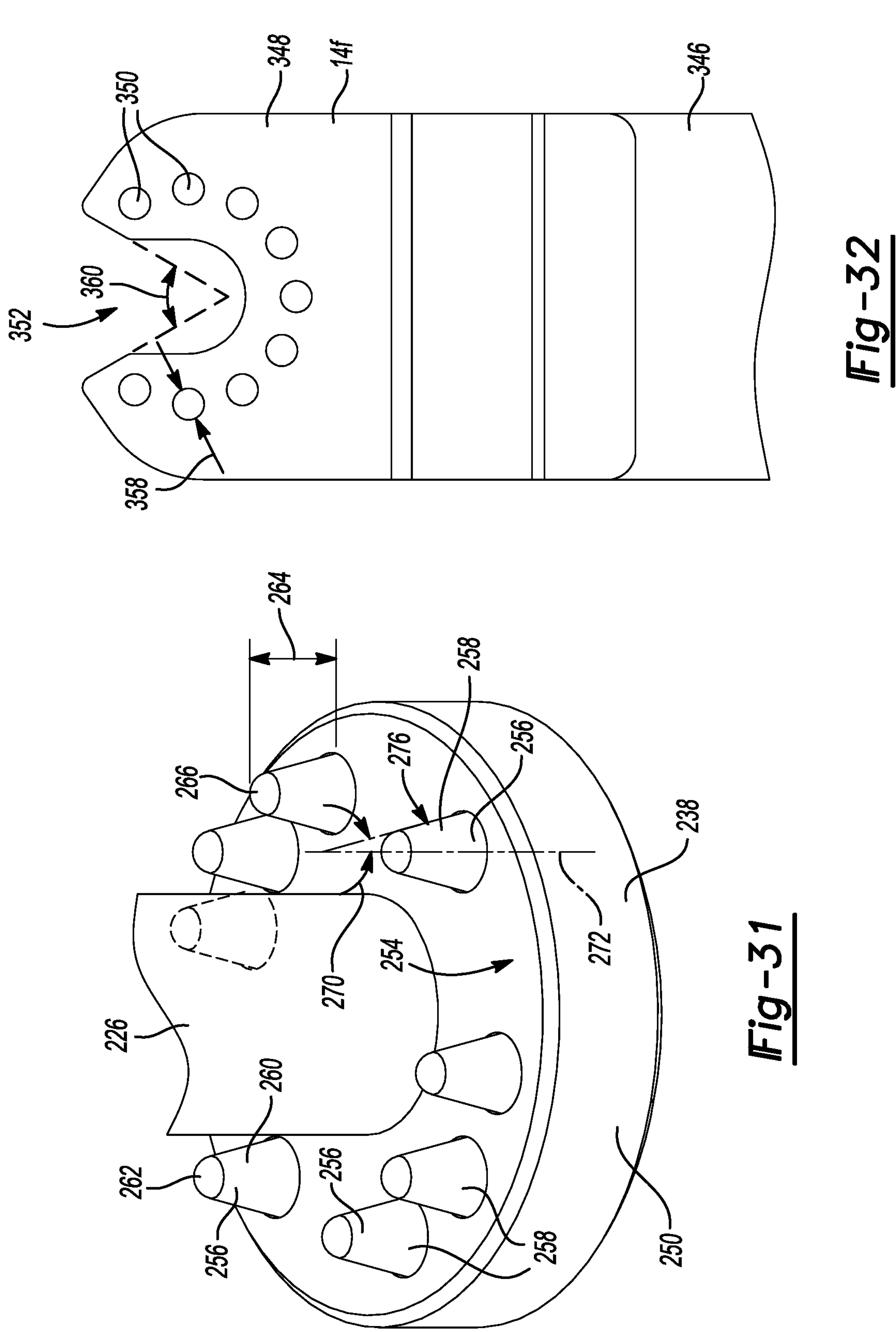
FIG. 31 is a perspective view of the second clamp member of the clamp assembly of FIG. 30.
FIG. 32 is a plan view of an accessory constructed in accordance to one example of the present teachings.
Figure 33:
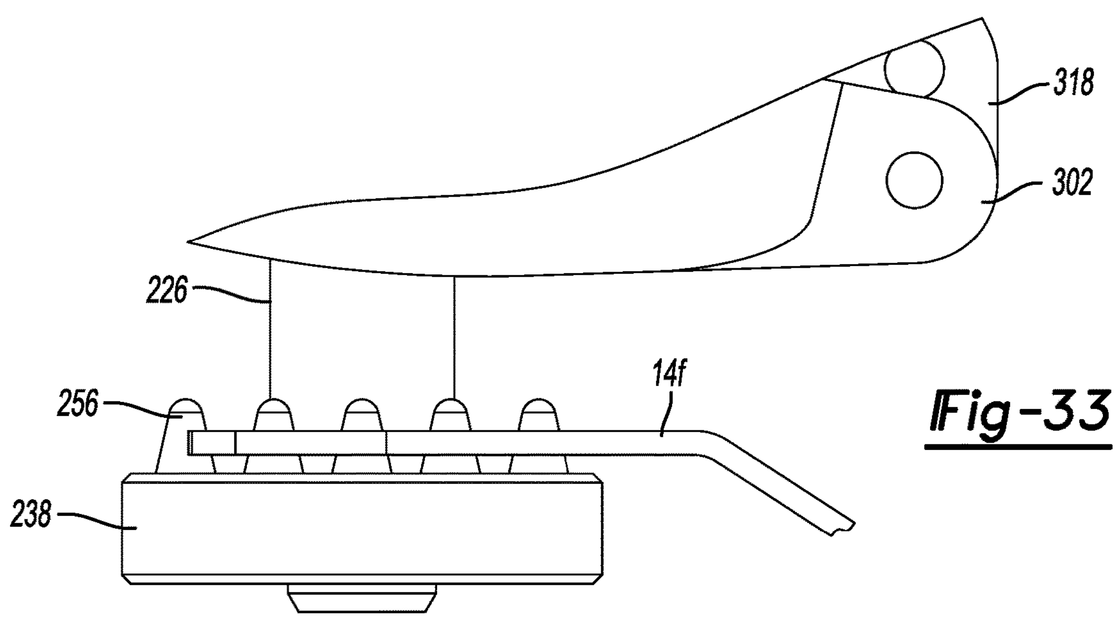
FIG. 33 is a side view of the accessory of FIG. 32 shown placed on the second clamp member and shown with the first clamp member removed for illustrative purposes.

With specific reference now to FIGS. 30 and 31, the second clamp member 238 will be further described. The second clamp member 238 can include a second clamp body 250 generally in the form of a ring having a central opening 252. The second clamp body 250 can generally comprise a second clamping surface 254 having a plurality of mounting features 256 formed thereon. In one example, the second clamp body 250 and the plurality of mounting features 256 can be formed as a unitary, monolithic part, such as by precision cast steel.

As will become appreciated by the following discussion, the second clamp member 238 is configured such that the second clamping surface 254 does not actually engage the sixth accessory 14*f*. In the example shown, the plurality of mounting features 256 are in the form of male conical protrusions 258. In the particular example shown, eight protrusions or male conical protrusions 258 are configured to each have a tapered body portion 260 that generally tapers from the second clamping surface 254 toward a tip 262. The tip 262 can generally comprise a spherical geometry. The male conical protrusions 258 each have a height 264 measured from the second clamping surface 254 to a terminal end 266 of the tip 262. The male conical protrusions 258 can further define an angle 270 measured from a longitudinal axis 272 to an outer surface 276 of the tapered body portion 260.

The male conical protrusions 258 can be configured to engage apertures of the sixth accessory 14*f* at a position intermediate the terminal end 266 of the tip 262 and the second clamping surface 254. Explained differently, the sixth accessory 14*f* can be clamped with the lever 232 in a first position and the clamp assembly 230 closed (FIG. 30), such that the sixth accessory 14*f* is offset a distance 280 from the second clamping surface 254. According to one example, the height 264 can be substantially about 4 mm and the angle 270 can be substantially about between 20° and 30° and more specifically 25°. A diameter of the male conical protrusions 258 measured at the second clamping surface 254 can be substantially about 3 mm. The surface finish of the male conical protrusions 258 can be sufficiently hard so as not to deform from interaction with the sixth accessory 14*f*. In one example, the male conical protrusions are at least 10 points (Rockwell hardness testing) harder than the sixth accessory 14*f*. Other heights and angles are contemplated.

With specific reference now to FIG. 30, the first clamp member 236 can generally include a first clamp member body 284 having an annular flange 286. The first clamp member body 284 can include a clamping surface 287 that has a plurality of mounting features 288 that are in the form of recesses that cooperatively receive the corresponding plurality of mounting features 256 of the second clamp member 238. The mounting features 288 can have any configuration, such as blind bores having diameters suitable to accept at least portions of the male conical protrusions 258 of the mounting features 256. The annular flange 286 can generally extend radially from an outer hub 290 of the first clamp member body 284. The annular flange 286 can have a lever opposing surface 291. The first clamp member body 284 can further include an inner hub 292 that defines a first clamp member opening 294. The first clamp member opening 294 can be configured to receive the spindle 226. An annular channel 296 can be formed between the outer hub 290 and the inner hub 292. The annular channel 296 can have a terminal surface 298.

The lever 232 can generally include a lever body 300 having the user engagement portion 242 formed generally on a first end and the pivot portion 246 formed on an opposite end. According to one example, the pivot portion 246 can generally include a pair of lobes 302 that each define an axle passage similar to the axle passage 104 described above with respect to FIG. 3. The lever body 300 can further include a pocket 308 having a flange opposing surface 310. A retainer plate 312 can be formed on the lever body 100. The retainer plate 312 can be configured to rest on the annular flange 286 when the lever 232 is released. The pivot axle 248 can be configured to pass through the respective axle passages of the lobes 302 and a corresponding axle passage 316 formed through an arm 318 extending from the housing 220.

The clamp arrangement 210 can additionally include a biasing member 320 and a washer 326. The biasing member 320 can be at least partially received by the annular channel 296 provided on the first clamp member body 284. The biasing member 320 can be generally supported on an upper end by a washer 326 that is correspondingly supported by a flange on the spindle 226. A distal end of the spindle 226 can be configured to attain a press fit relationship (through the central opening 252) with the second clamp body 250.

With particular reference now to FIG. 32, the sixth accessory 14*f* will be described. The sixth accessory 14*f* can generally be in the form of a cutting member having a working portion 346 and an attachment portion 348. The attachment portion 348 can include a plurality of mounting features 350 in the form of passages formed through the sixth accessory 14*f*. The attachment portion 348 can further include an open-ended aperture or throat 352 for selectively receiving a portion of the spindle 226 in an assembled position as will be described herein. According to one example of the present teachings, the plurality of mounting features 350 can be circular and have a diameter 358 of substantially about 2.8 mm. The throat 352 can define an angle 360 of about 60°. Other dimensions are contemplated. It will be appreciated however that the diameter 358 is selected to have a geometry such that it will engage the tapered body portion 260 of the male conical protrusions 258 at a location intermediate the terminal end 266 of the tip 262 and the second clamping surface 254. More particularly, the diameter 358 has a geometry that will ensure the attachment portion 348 does not bottom out or rest on top of the second clamping surface 254. In other words, the distance 280 (FIG. 30) must be greater than zero.

The mounting features 256 can be arranged to allow the sixth accessory 14*f* to be indexed at about 30° increments around the second clamping surface 254. Like the mounting features 76 described above, the mounting features 256 are absent at the two, four, eight and ten o'clock positions. It is further appreciated that the clamp assembly 230 can be used to clamp other accessories, such as described herein. Other configurations are contemplated.

With specific reference now to FIGS. 30 and 34, an exemplary sequence of removing the sixth accessory 14*f* from the clamp assembly 230 will be described according to one example of the present teachings. With initial reference to FIG. 30, the clamp assembly 230 is shown in a closed position wherein the biasing member 320 is supported on a first end by the washer 326 and provides a downward biasing force onto the first clamp member 236 at the annular channel 296. It is important to recognize that in the particular example shown, the second clamp member 238 is fixed relative to the spindle 226. As shown, the male conical protrusions 258 selectively locate into the recesses of the mounting features 288 formed on the first clamp member 236. The sixth accessory 14*f* therefore is clamped between the clamping surface 287 and the outer surfaces 276 of the respective male conical protrusions 258. Again, the sixth accessory 14*f* is clamped at a location offset from the second clamping surface 254 of the second clamp member 238. As viewed in FIG. 30, the lever 232 is shown and generally described herein as the first position. Because the sixth accessory 14*f* is specifically engaged at the mounting features 350, the sixth accessory 14*f* can be securely fixed against the clamping surface 287 with minimal or no relative movement between the sixth accessory 14*f* and the clamp assembly 230.

Figure 34:
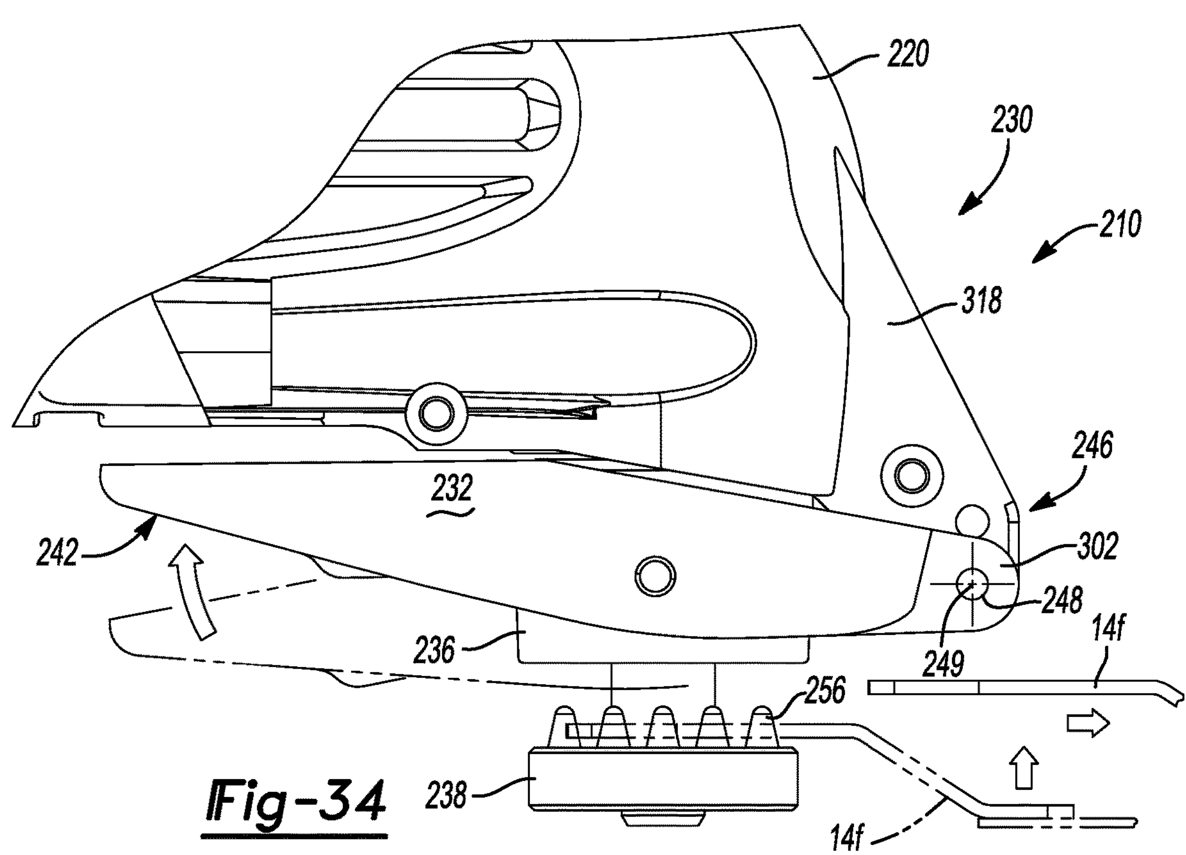
FIG. 34 is a side view of the clamp assembly shown during removal of the accessory where the lever is moved from the first position (phantom) to a second position (solid line) and the first clamp member is raised away from engagement with the accessory.

Turning now specifically to reference FIG. 34, the lever 232 is shown rotated from the first position (phantom line) around the pivot axle axis 249 to a second position (solid line). In the second position, the clamp assembly 230 is generally in the open position where the first clamp member 236 is displaced or offset relative to the second clamp member 238. In order to move the lever 232 from the first position (phantom line, FIG. 34) to the second position (solid line, FIG. 34), a user can urge the user engagement portion 242 (such as by pulling the user engagement portion 242 with an index finger) in a direction generally upwardly as viewed in FIG. 34 and toward the housing 220. In order to rotate the lever 232 around the pivot axle 248, a user must overcome the biasing force of the biasing member 320 (FIG. 30). During rotation of the lever 232 around the pivot axle 248, the flange opposing surface 310 and the pocket 308 of the lever body 300 generally transmits an upward force (in a direction against the biasing force of the biasing member 320) onto the lever opposing surface 291. In this regard, the lever 232 can generally lift the first clamp member 236 at the annular flange 286 to move the clamping surface 287 away from the second clamp member 238.

With the clamp assembly 230 in the open position, the first and second clamp members 236 and 238, respectively, provide enough clearance, such that a user can remove the sixth accessory 14*f* away from the clamp assembly 230. In one example, it may be necessary to initially lift the sixth accessory 14*f* away from the male conical protrusions 258 before pulling the sixth accessory 14*f* away from the clamp assembly 230.

The pivot axle 248 can be located a distance 370 measured perpendicularly from a point 372 on a longitudinal centerline of the spindle 226. In one example, the distance 370 can be long enough to give the user a mechanical advantage to comfortably overcome the bias of the biasing member 320 when moving the lever 232 to the second position (clamp assembly 230 open). A distance 374 measured between the point 372 and a plane defined by the clamping surface 287 can be less than the distance 370.

Figure 35:
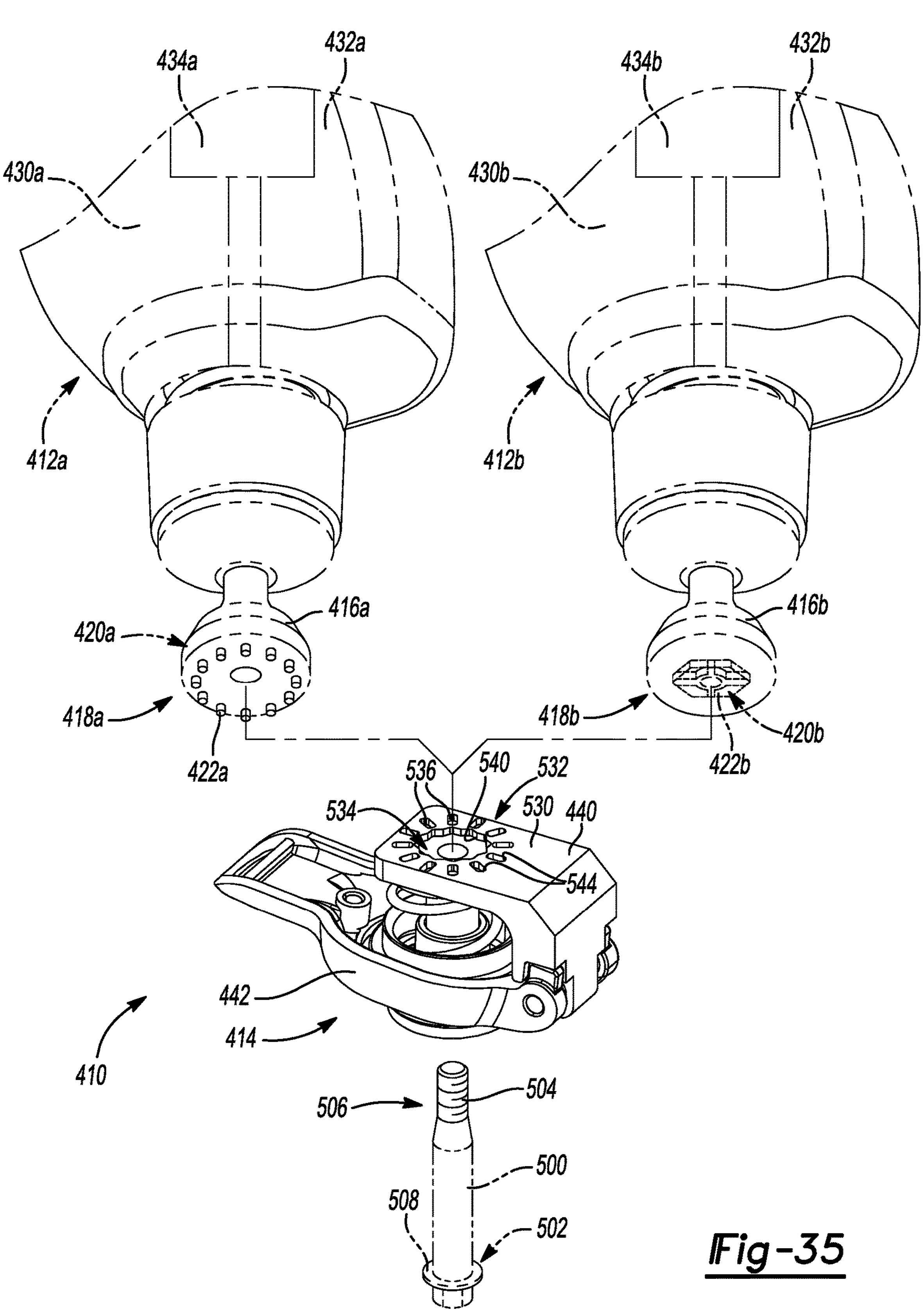
FIG. 35 is an exploded perspective view of a clamp assembly constructed in accordance to another example of the present teachings and shown with a fastener for selectively and alternatively coupling the clamp assembly to one of a first power tool or a second power tool.
Figures 36, 37:
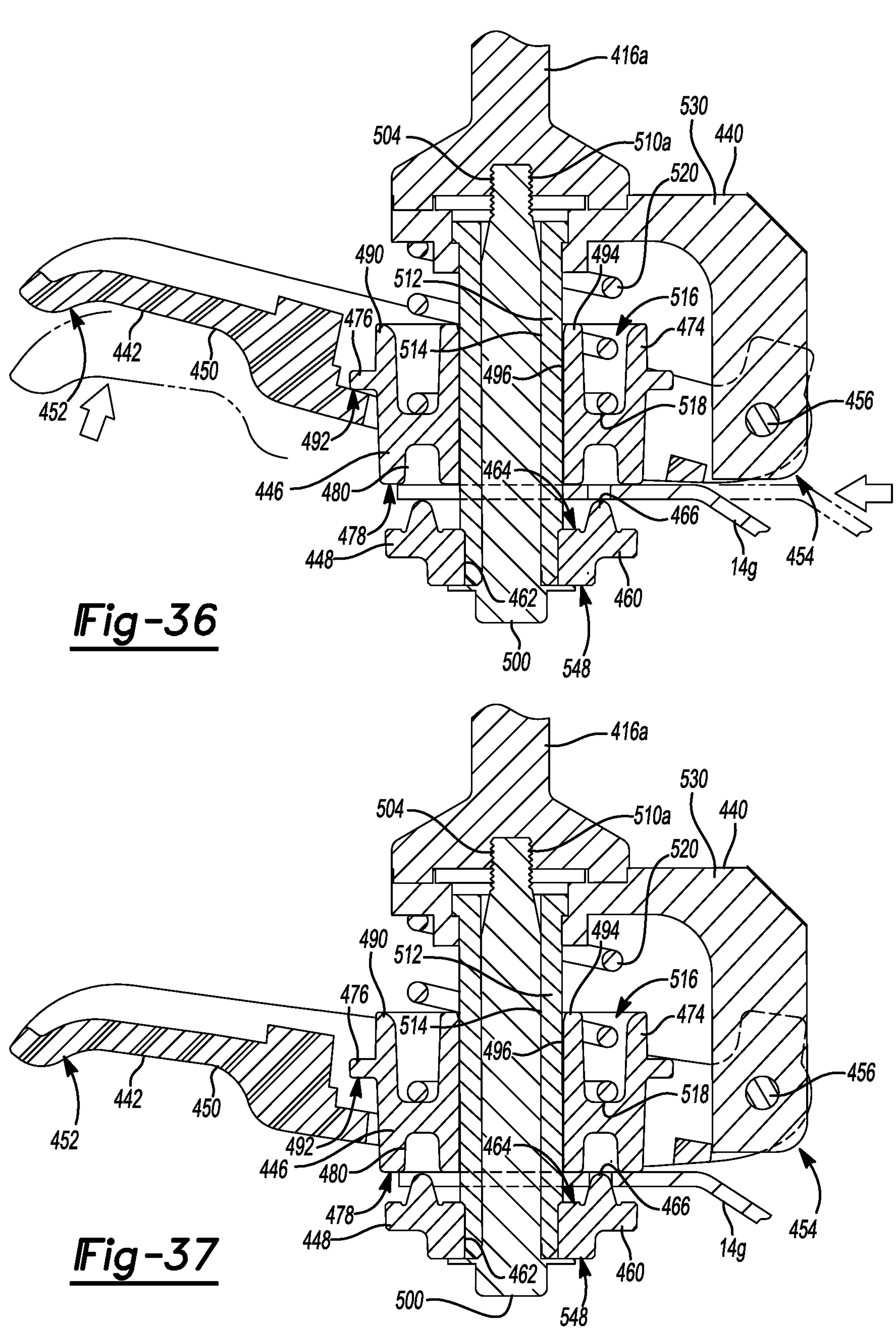
FIG. 36 is a sectional view of the clamp assembly of FIG. 35 shown coupled to a first tool mating detail of the first power tool.
FIG. 37 is a cross-sectional view of the clamp assembly of FIG. 36 and shown with the clamp assembly in the open position resulting from the lever being rotated about a pivot axle into a second position wherein an accessory may be inserted for clamping.

With reference now to FIGS. 35-38, a clamp arrangement constructed in accordance to another example of the present disclosure is shown and generally identified at reference numeral 410. The clamp arrangement 410 is shown operatively associated with a first power tool 412*a* and a second power tool 412*b*. As will be described in detail herein, the clamp arrangement 410 includes a clamp assembly 414 that is configured to be selectively and alternatively coupled to either of the first power tool 412*a* or the second power tool 412*b*. The clamp assembly 414 is configured to selectively and alternatively retain various accessories such as a seventh accessory 14*g* (FIG. 37). As will become appreciated from the following discussion, the clamp assembly 414 is configured to suitably couple with an output member 416*a* provided on the first power tool 412*a* or an output member

416*b* provided on the second power tool 412*b*. In this regard, the output member 416*a* may include a first tool mating detail 418*a* having a first mating geometry 420*a*. The output member 416*b* may incorporate a second tool mating detail 418*b* having a second mating geometry 420*b*. In the example shown, the first mating geometry 420*a* provided on the output member 416*a* includes twelve circular shaped protrusions 422*a*. The second mating geometry 420*b* provided on the output member 416*b* includes a male protrusion 422*b*. The male protrusion 422*b* may alternatively comprise either of a four point star or a hexagonal protrusion. As will become appreciated herein, the clamp assembly 414 includes complementary geometry suitable to selectively and alternatively mate with an output member 416*a* having a male protrusion 422*b* in the form of a four point star or a hexagon.

The first power tool 412*a* generally includes a tool body 430*a* having a housing 432*a* that generally contains a motor 434*a* that drives the output member 416*a*. Similarly, the second power tool 412*b* includes a tool body 430*b* having a housing 432*b* that contains a motor 434*b* that drives the output member 416*b*. The output members 416*a* and 416*b* of the respective first and second power tools 412*a* and 412*b* can be configured to provide an oscillating motion.

The clamp assembly 414 generally includes an attachment plate 440 having a lever 442 pivotally coupled thereto. The clamp assembly 414 can generally include a first clamp member 446 and a second clamp member 448 (FIG. 36). The lever 442 can include a lever arm 450 that includes a user engagement portion 452. The lever 442 can further include a pivot portion 454 having a pivot axle 456.

The second clamp member 448 can include a second clamp body 460 generally in the form of a ring having a central opening 462. The second clamp body 460 can generally comprise a second clamping surface 464 having a plurality of mounting features 466 formed thereon. In one example, the second clamp body 460 and the plurality of mounting features 466 can be formed as a unitary, monolithic part, such as by precision cast steel. In other examples, the plurality of mounting features 466 may be separately formed and coupled to the clamp body 460. The second clamp member 448 may be configured similarly to the second clamp member 238 described above. In this regard, the second clamp member 448 may comprise eight protrusions or male conical portions that are configured to each have a tapered body portion that generally tapers from the second clamping surface 464 toward a tip.

The first clamp member 446 can generally include a first clamp member body 474 having an annular flange 476. The first clamp member body 474 can include a clamping surface 478 that has a mounting feature 480 that is in the form of an annular recess that cooperatively receive the corresponding plurality of mounting features 466 of the second clamp member 448. The mounting feature 480 can have any configuration that may cooperatively accept at least portions of the mounting features 466. The annular flange 476 can generally extend radially from an outer hub 490 of the first clamp member body 474. The annular flange 476 can have a lever opposing surface 492. The first clamp member body 474 can further include an inner hub 494 that defines a first clamp member opening 496. The first clamp member opening 496 can be configured to receive a fastener 500. The fastener 500 can generally include a fastener head 502 and threads 504 formed on a distal end 506. The head 502 may incorporate an optional flange 508. The threads 504 can be configured to threadably mate with a threaded bore 510*a* defined in the output member 416*a* (or a threaded bore 510*b* formed in the output member 416*b*). In some examples, a cannulated sleeve 512 having a cannulation 514 may be positioned between the fastener 500 and the first clamp member opening 496 of the inner hub 494. The cannulated sleeve 512 can be fixed between the attachment plate 440 and the second clamp body 460. An annular channel 516 can be formed between the outer hub 490 and the inner hub 494. The annular channel 516 can have a terminal surface 518. A biasing member 520 can be partially received by the annular channel 516. The operation of the biasing member 520 is similar to that described above with respect to the biasing member 120 (FIGS. 4-6).

In general, the lever 442, first clamp member 446, and second clamp member 448 may function similar to the configurations described above. However, with the clamp assembly 414 as described with respect to FIGS. 35-38, the attachment plate 440 can be selectively secured to various power tools including the first power tool 412*a* and the second power tool 412*b*. The attachment plate 440 can generally include an attachment plate body 530 that provides an attachment plate mating detail 532. The attachment plate mating detail 532 can generally comprise a central recess 534 and a plurality of receiving portions 536 formed thereon. In the example provided, the central recess 534 can be generally defined by a keyed sidewall 540 defined into the body 530. Similarly, the plurality of receiving portions 536 can be generally defined into the body 530 as oval recesses 544. The keyed sidewall 540 can generally be in the form of a twelve point star. As can be appreciated, the oval recesses 544 can be configured to selectively receive the protrusions 422*a* provided on the first mating geometry 420*a* of the first power tool 412*a*. Notably, the oval recesses 544 are configured to suitably receive circular shaped protrusions 422*a* of multiple tools having various diameters. Similarly, the central recess 534 can be configured to cooperatively receive the male protrusion 422*b* (either the four point star in one configuration, or the hexagon in another configuration) provided by the second mating geometry 420*b*. In this regard, the attachment plate 440 may offer a user a variety of distinct mounting configurations for suitably coupling the clamp assembly 414 to a wide range of power tools including the first and second power tools 412*a* and 412*b* shown in FIG. 35. It will be further appreciated that the interlocking geometries of the mating detail 532 of the attachment plate 440 and the first and second tool mating details 418*a* and 418*b* of the first and second power tools 412*a* and 412*b*, respectively may take other shapes.

Figures 38, 39:
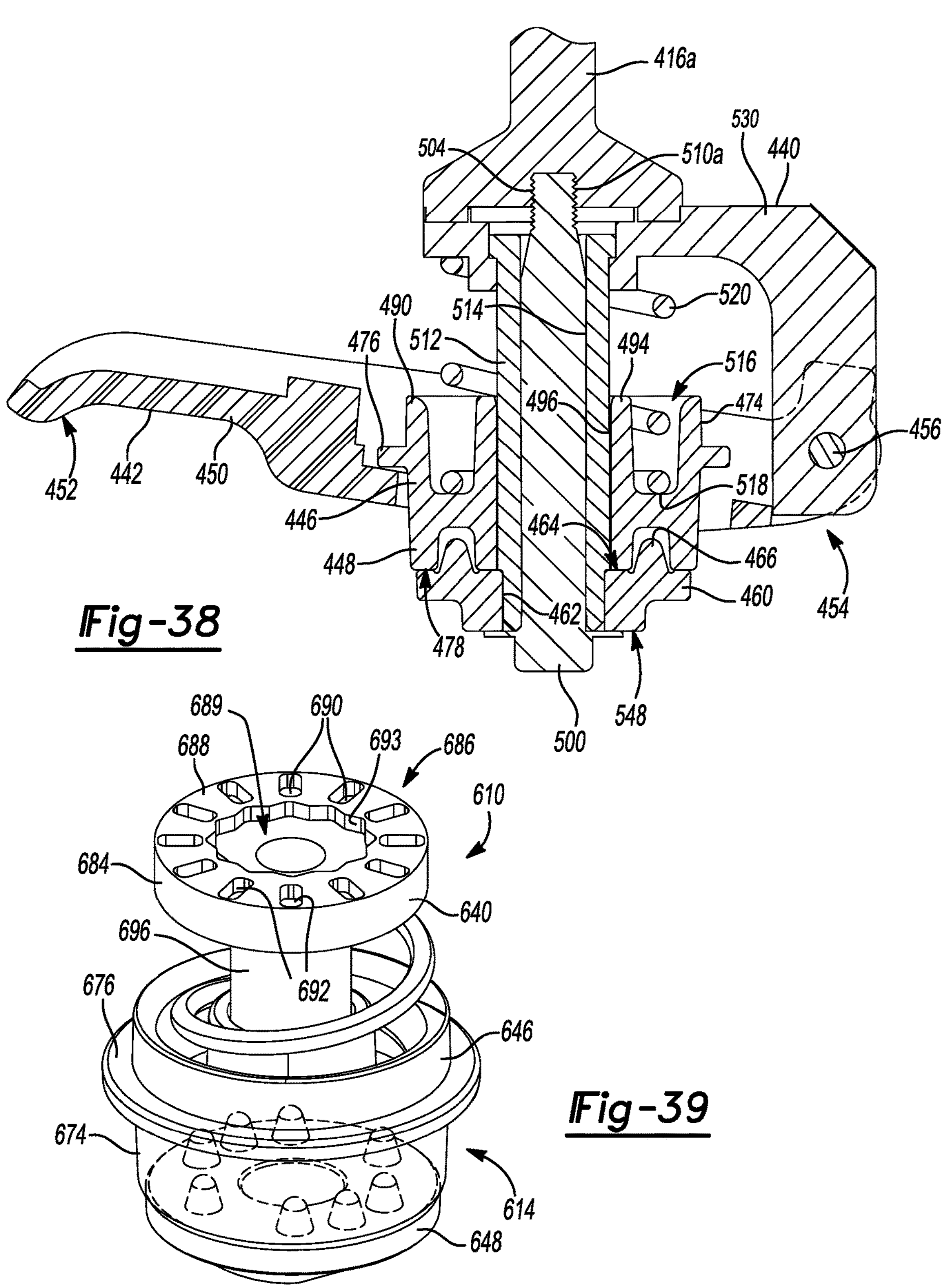
FIG. 38 is a cross-sectional view of the clamp assembly of FIG. 37 and shown with the clamp assembly in a closed position wherein the accessory is clamped between the first and second clamp members.
FIG. 39 is a front perspective view of a clamp assembly constructed in accordance to another example of the present teachings.

In one example of coupling the clamp assembly 414 to the first power tool 412*a*, a user may initially align the attachment plate mating detail 532 with the first tool mating detail 418*a*. In the example provided, the user may align the oval recesses 544 defined in the body 530 of the attachment plate 440 for receipt of the complementary circular protrusions 422*a* extending from the first mating geometry 420*a* of the output member 416*a*. As can be appreciated, once the protrusions 422*a* are selectively received by the oval recesses 544 in the attachment plate 440, the clamp assembly 414 is rotationally fixed with the output member 416*a*. Next, a user may advance the fastener 500 through the cannulation 514 of the cannulated sleeve 512 and threadably advance the threads 504 into the threaded bore 510*a* defined in the output member 416*a*. In the example provided, the head 502 can engage an outer surface 548 of the second clamp member 448. As can be appreciated, in the assembled position (FIGS. 36-38), the clamp assembly 414 will be fixed for oscillating motion with the output member 416*a* of the first power tool 412*a*. As shown in FIGS. 37-38, the clamp assembly 414 may selectively accept the accessory 14*g* similar to the clamp assembly 230 (FIG. 30) described above. Therefore, the sequence will not be repeated here.

Figures 40, 41:
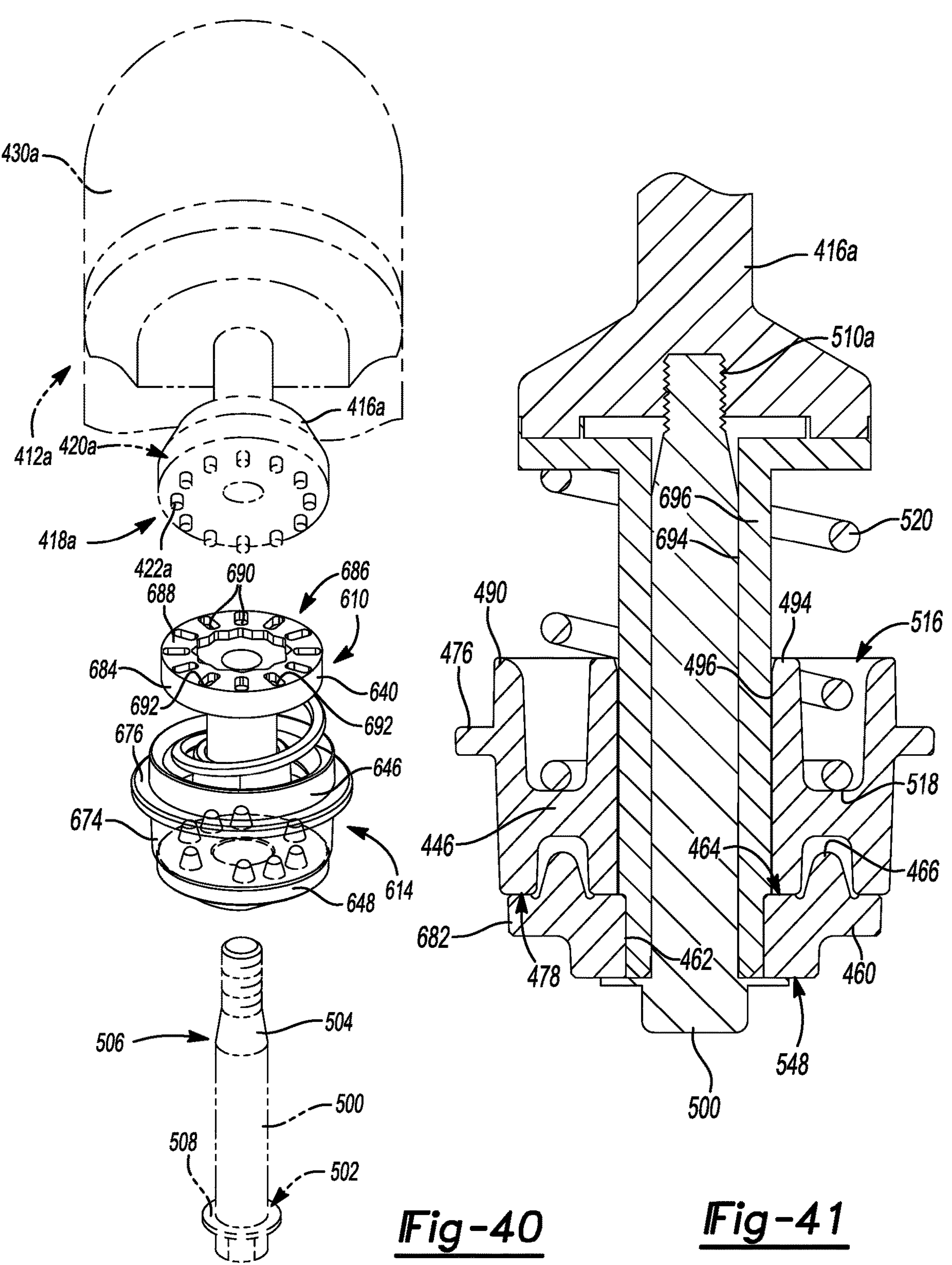
FIG. 40 is an exploded perspective view of the clamp assembly of FIG. 39 and shown operatively associated with the first power tool and a fastener.
FIG. 41 is a cross-sectional view of the clamp assembly of FIG. 40 shown in an installed position wherein the fastener threadably mates with an output member of the first power tool.
Figures 42, 43:
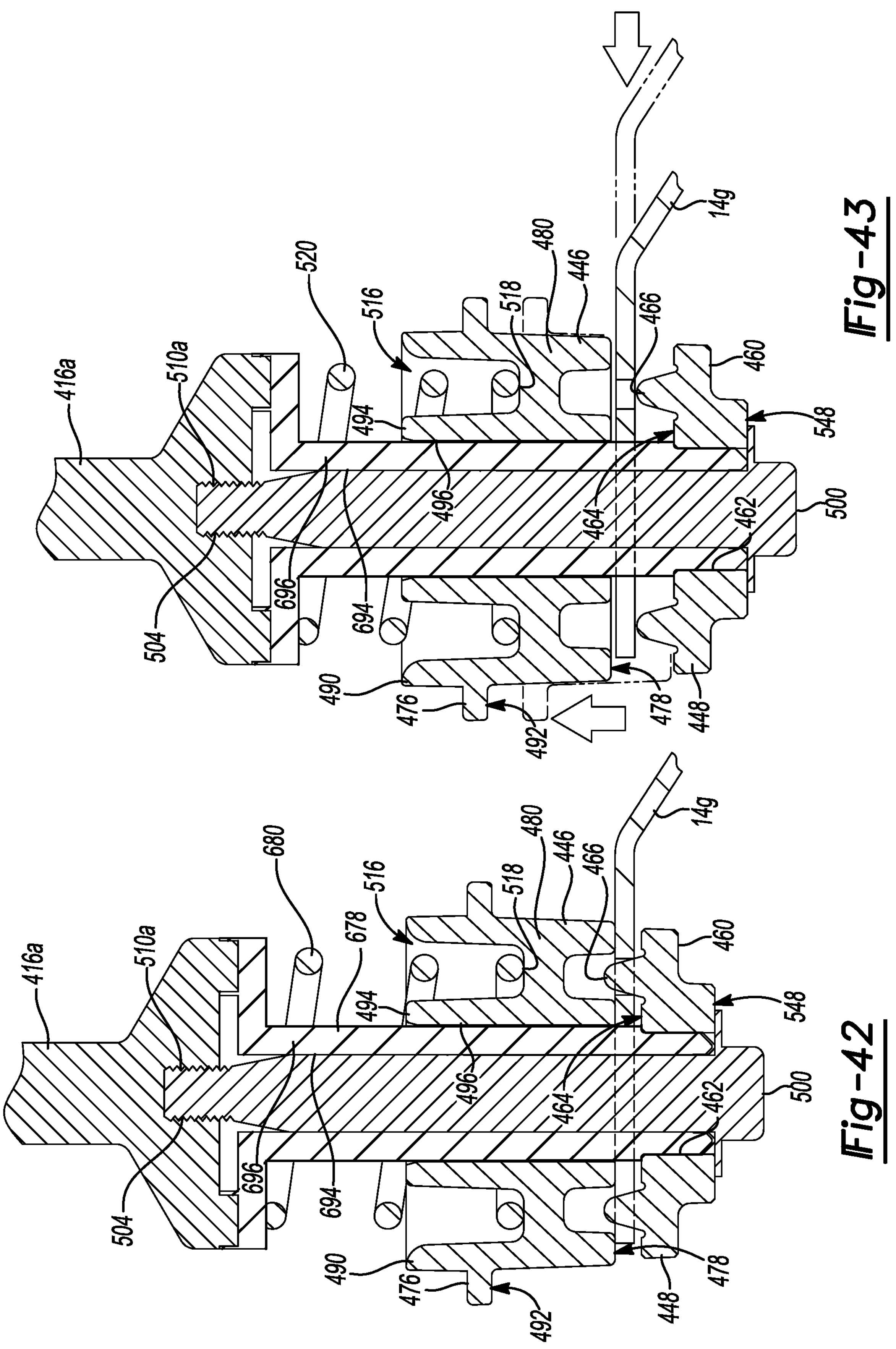
FIG. 42 is a cross-sectional view of the clamp assembly of FIG. 41 and shown with the clamp assembly in the open position for receipt of an accessory.
FIG. 43 is a cross-sectional view of the clamp assembly of FIG. 42 and shown with the clamp assembly in the closed position and clamping the accessory between a first and second clamp member.

With reference now to FIGS. 39-43, a clamp arrangement constructed in accordance to another example of the present disclosure is shown and generally identified at reference numeral 610. The clamp arrangement 610 is shown generally associated with the first power tool 412*a* (FIG. 40). As will be described in detail herein, the clamp arrangement 610 includes a clamp assembly 614 that is configured to be selectively coupled to the first or second power tools 412*a* and 412*b*. Again, it will be appreciated that the clamp assembly 614 may incorporate additional or alternative geometry for mating with other power tools such as those described herein. The clamp assembly 614 is configured to selectively and alternatively retain various accessories such as the seventh accessory 14*g* (FIG. 43). The clamp assembly 614 is configured to suitably couple with either of the output member 416*a* provided on the first power tool 412*a* or the output member 416*b* provided on the second power tool 412*b*.

The clamp assembly 614 generally includes an attachment plate 640 having a first clamp member 646 and a second clamp member 648. The first clamp member 646 is configured to translate relative to the second clamp member 648. The first clamp member 646 can generally include a first clamp member body 674 having an annular flange 676. The clamp assembly 614 is configured to operate similar to the clamp assembly 414 described above but without the incorporation of a lever. In this regard, a user may engage the annular flange 676 and translate the first clamp member body 674 toward the attachment plate 640 against the bias of a biasing member 680 to move the first clamp member 646 from a clamped position (FIG. 43) to an unclamped position (FIG. 44).

The second clamp member 648 can include a second clamp body 682. The second clamp body 682 can be generally formed similar to the second clamp body 460 described above and will not be repeated here. The attachment plate 640 can generally include an attachment plate body 684 that provides an attachment plate mating detail 686. The attachment plate mating detail 686 can generally comprise a raised annular rim 688 having a central recess 689 and a plurality of receiving portions 690 formed thereon. In the example provided, the raised rim 688 incorporates twelve receiving portions 690 in the form of oval recesses 692. As can be appreciated, the oval recesses 692 can be configured to selectively receive the protrusions 422*a* provided on the first mating geometry 420*a* of the first power tool 412*a*. The central recess 689 can be a keyed sidewall 693 defined into the attachment plate body 684. The keyed sidewall 693 can generally be in the form of a twelve point star.

In one example of coupling the clamp assembly 614 to the first power tool 612*a*, a user may initially align the attachment plate mating detail 686 defined in the body 684 of the attachment plate 640 for receipt of the complementary circular protrusions 422*a* extending from the first mating geometry 420*a* of the output member 416*a*. Once the protrusions 422*a* are selectively received by the oval recesses 692 in the attachment plate 640, the clamp assembly 614 is rotationally fixed with the output member 616*a*. Next, a user may advance the fastener 500 through a cannulation 694 of a cannulated sleeve 696 and threadably advance the threads 504 into the threaded bore 510*a* defined in the output member 416*a*.

Figure 44:
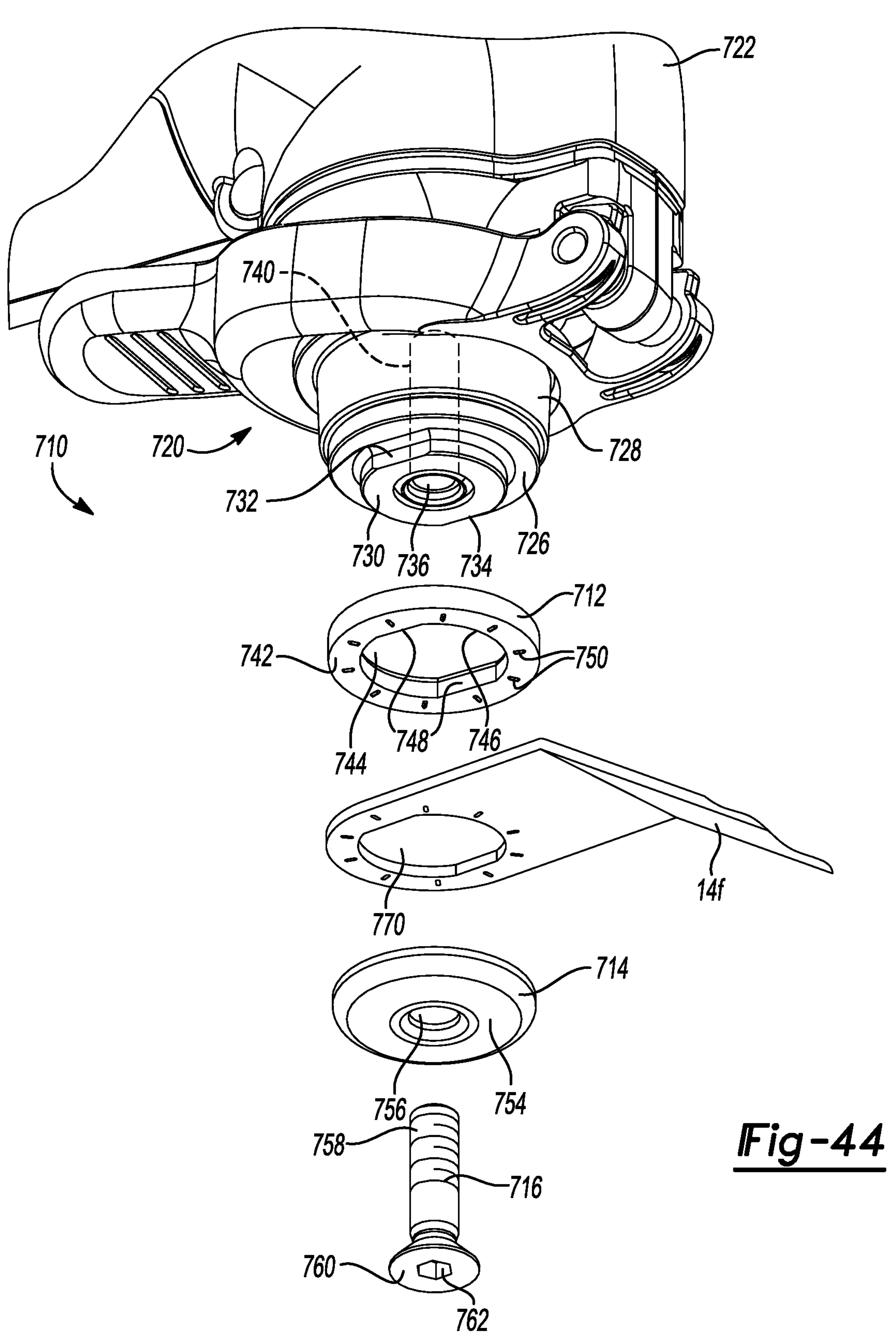
FIG. 44 is an exploded perspective view of a clamp assembly constructed in accordance to another example of the present teachings.
Figures 45, 46:
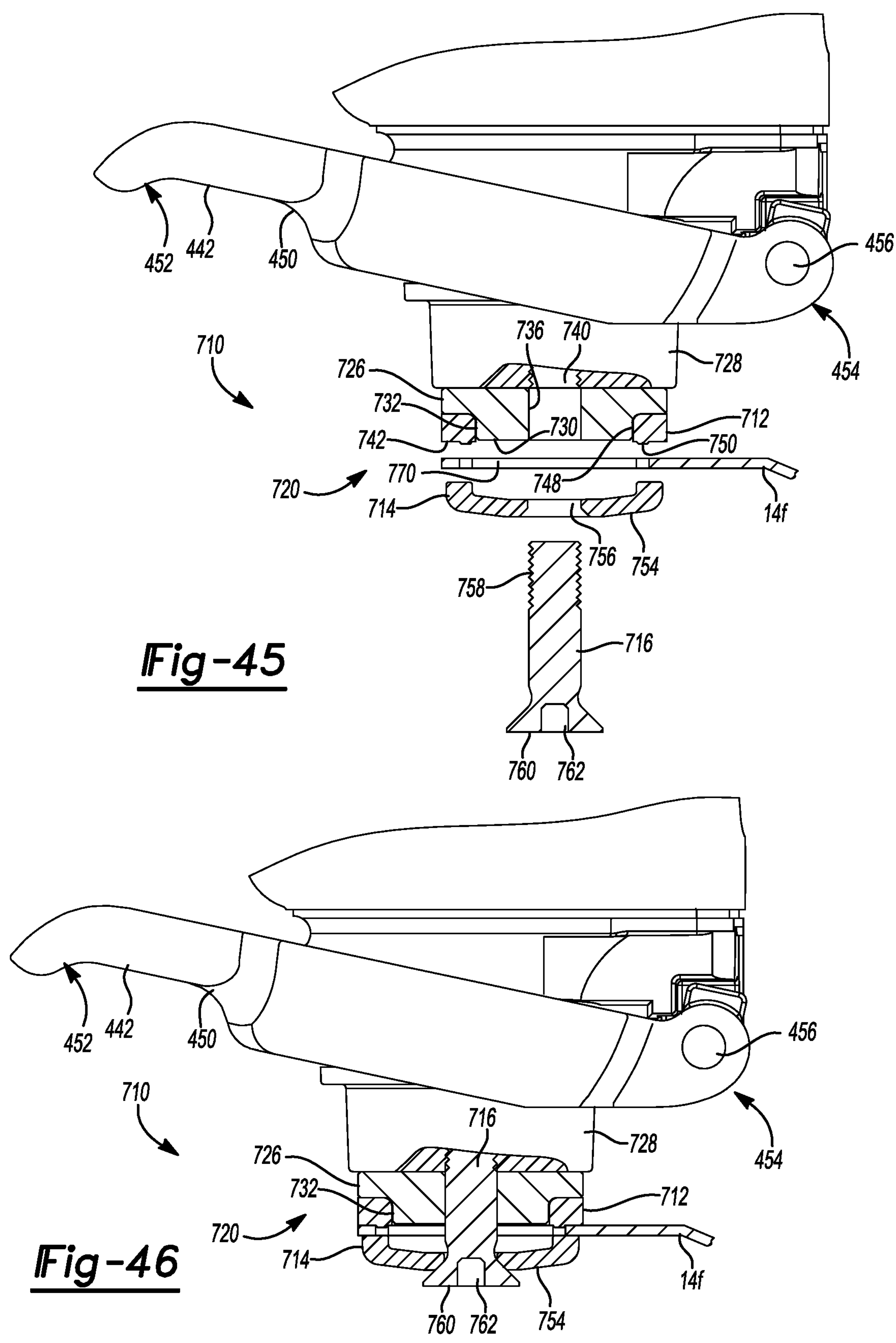
FIG. 45 is an exploded cross-sectional view of the clamp assembly of FIG. 44.
FIG. 46 is a cross-sectional view of the clamp assembly of FIG. 45 and shown with an accessory coupled to an outboard face of a clamp member with an adapter plate, a clamp plate, and a fastener.

With reference now to FIGS. 44-46, an attachment assembly constructed in accordance to additional features of the present disclosure is shown and generally identified at reference numeral 710. In general, the attachment assembly 710 generally includes an adapter plate 712, a clamp plate 714, and a fastener 716. As will become appreciated from the following discussion, the attachment assembly 710 may be configured to cooperate with any of the clamping arrangements discussed above for coupling an accessory, such as an accessory 14*f* to the clamp assembly 720 provided on a power tool 722. Specifically, the attachment assembly 710 may be configured to suitably connect to a second clamp member 726 of the clamp assembly 720 that may additionally include a first clamp member 728.

The second clamp member 726 can generally include a raised central boss 730 that can define flats 732 and 734 thereon. An opening 736 can also be formed through the second clamp member 726. The first clamp member 728 may define a threaded aperture 740 therein. The adapter plate 712 can generally define an adapter plate body 742 having a central opening 744. The central opening 744 may be defined in part by a radial sidewall 746 having diametrically opposed flats 748. The body 742 can additionally include a plurality of outwardly extending protrusions 750 thereon. The clamp plate 714 can generally include a clamp plate body 754 that defines a central opening 756 therein. The fastener 716 may generally include a threaded shank 758 and a proximal head 760. The head 760 can define a gripping detail 762. The exemplary gripping detail 762 is in the form of a hex recess, however other details may be incorporated.

Figures 47, 48:
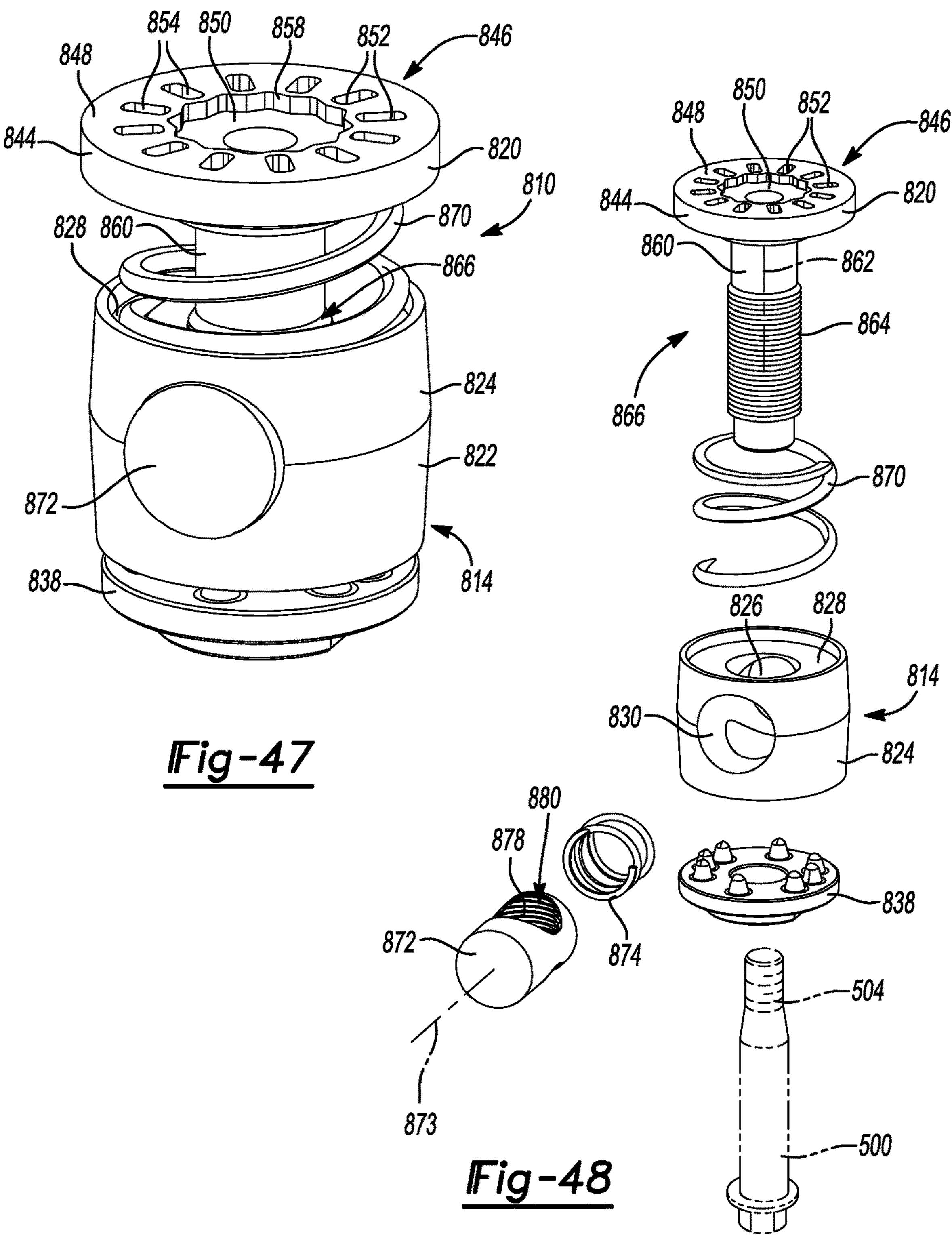
FIG. 47 is a front perspective view of a clamp assembly constructed in accordance to another example of the present teachings.
FIG. 48 is an exploded perspective view of the clamp assembly of FIG. 47.

In one example of coupling the attachment assembly 710 to the power tool 722, the adapter plate 712 may be located onto the second clamp member 726. In this regard, the opposing flats 748 of the adapter plate 712 can be rotationally aligned with the corresponding flats 732 and 734 provided on the raised central boss 730 of the second clamp member 726. The fastener 716 may then be inserted through the opening 756 of the clamp plate 714 and through an opening 770 in the accessory 14*f*. The threaded shank 758 can then be threadably advanced into the threaded aperture 740 defined in the first clamp member 728 until the clamp plate 714 clamps the accessory 14*f* against the adapter plate 712 (FIG. 48). As can be appreciated, the protrusions 750 extending from the adapter plate body 742 can provide additional gripping onto the accessory 14*f*.

Figures 49, 50:
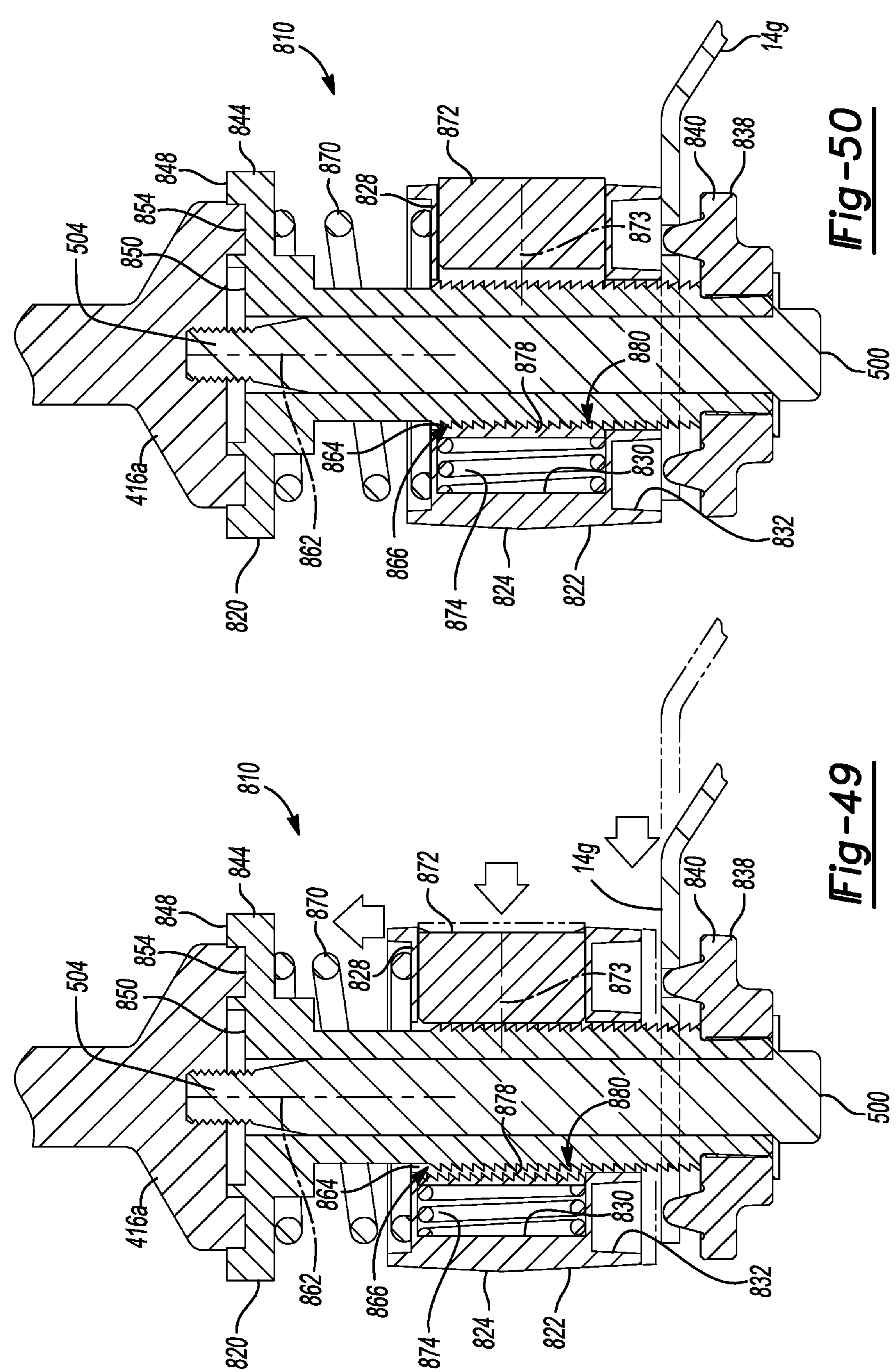
FIG. 49 is a cross-sectional view of the clamp assembly of FIG. 47 and shown with the clamp assembly in the open position for receipt of an accessory.
FIG. 50 is a cross-sectional view of the clamp assembly of FIG. 49 and shown with the clamp assembly in the closed position and clamping the accessory between the first and second clamp member.

With reference now to FIGS. 47-50, a clamp arrangement constructed in accordance to another example of the present disclosure is shown and generally identified at reference numeral 810. The clamp arrangement 810 is shown generally associated with a first output member 416*a* (FIG. 49) of the first power tool 412*a* (FIG. 40). As will be described in detail herein, the clamp arrangement 810 includes a clamp assembly 814 that is configured to be selectively coupled to the first or second power tools 412*a* and 412*b*. Again, it will be appreciated that the clamp assembly 814 may incorporate additional or alternative geometry for mating with other power tools such as those described herein. The clamp assembly 814 is configured to selectively and alternatively retain various accessories such as the seventh accessory 14*g* (FIGS. 49-50). In this regard, the clamp assembly 814 is configured to suitably couple with either of the output member 416*a* provided on the first power tool 412*a* or the output member 416*b* provided on the second power tool 412*b*.

The clamp assembly 814 generally includes an attachment plate 820 having a first clamp member 822 movably coupled thereto. The first clamp member 822 can generally include a first clamp member body 824 that defines a through bore 826 (FIG. 48), an inset 828, a blind bore 830, and a radial channel 832 (FIG. 49). A fastener 500 can include threads 504 that threadably mate with corresponding threads defined in the output member 416*a*. The fastener 500 can therefore capture the clamp assembly 814 to the identified power tool.

The first clamp member 822 is configured to translate relative to a second clamp member 838 as will become appreciated from the following discussion. The second clamp member 838 can include a second clamp body 840. The second clamp body 840 can be generally formed similar to the second clamp body 460 described above and will not be repeated here. The attachment plate 820 can generally include an attachment plate body 844 that provides an attachment plate mating detail 846. The attachment plate mating detail 846 can generally comprise a raised annular rim 848 having a central recess 850 and a plurality of receiving portions 852 formed thereon. In the example provided, the raised rim 848 incorporates twelve receiving portions 852 in the form of oval recesses 854. The oval recesses 854 can be configured to selectively receive the protrusions 422*a* provided on the first mating geometry 420*a* of the first power tool 412*a*. Again, the oval recesses 854 can cooperatively mate with protrusions 422*a* having various diameters.

The central recess 850 can be a keyed sidewall 858 defined into the attachment plate body 844. The keyed sidewall 858 can generally be in the form of a twelve point star. In the example provided, the attachment plate 820 further comprises a stem 860 extending therefrom. The stem 860 can be integrally formed or coupled to the attachment plate 820 and to the second clamp member 838. The stem 860 defines a longitudinal axis 862. A first series of ridges 864 can be formed around the stem 860. The first series of ridges 864 can collectively define a first gripping detail 866. The first gripping detail 866 can therefore be associated with, or fixed relative to, the second clamp member 838.

With particular reference now to FIGS. 48 and 49, additional features of the clamp assembly 814 will be described. A first biasing member 870 can be located generally around the stem 860 and configured for engaging the clamp member body 824 at the inset 828 on one end and the attachment plate 820 on an opposite end. In this regard, the first biasing member 870 can provide a biasing force onto the clamp member body 824 in the direction of the second clamp member 838 or downwardly along the longitudinal axis 862. A button 872 defines a button axis 873 and can be at least partially received into the blind bore 830 of the clamp member body 824 against a bias of a second biasing member 874. The button 872 includes a second series of ridges 878 that collectively define a second gripping detail 880. In the example provided, the first and second series of ridges 864, 878 comprise discontinuous, stepped radial ridges.

With reference now to FIGS. 49 and 50, operation of the clamp assembly 814 according to one example of the present teachings will be described. At the outset, it will be appreciated that the first series of ridges 864 can cooperate with the second series of ridges 878 for locating the button 872 at a desired location along the stem 860. Explained in greater detail, the second biasing member 874 can provide a bias against the button 872 forcing the button 872 in a direction rightward as viewed in FIG. 49 along the button axis 873. In this regard, the second gripping detail 880 of the second series of ridges 878 on the button 872 are caused to mate and therefore cooperatively lock with the first gripping detail 866 of the first series of ridges 864 on the stem 860. When an operator wishes to change the location of the clamp member body 824, the button 872 can be depressed or translated in a direction leftward along the button axis 873 against the bias of the second biasing member 874. In this regard, the first series of ridges 864 and the second series of ridges 878 are caused to disengage whereby the operator can subsequently translate the clamp member body 824 in a direction along the axis 862 of the stem 860.

Once the desired elevation has been achieved, the operator can release the button 872 causing the respective first and second ridges 864 and 878 to lock. At this time, the user can place the desired accessory between the first and second clamp members 822 and 838. Next, the user can again depress the button 872 allowing the first biasing member 870 to direct the clamp member body 824 in a direction toward the accessory 14*g* until the accessory 14*g* is suitably clamped between the first and second clamp members 822 and 838. It will be appreciated that the operator is not required to release the button 872 to lock the clamp member body 824 at a displaced position from the second clamp member 838 while inserting the accessory 14*g*.

Figures 53, 54:
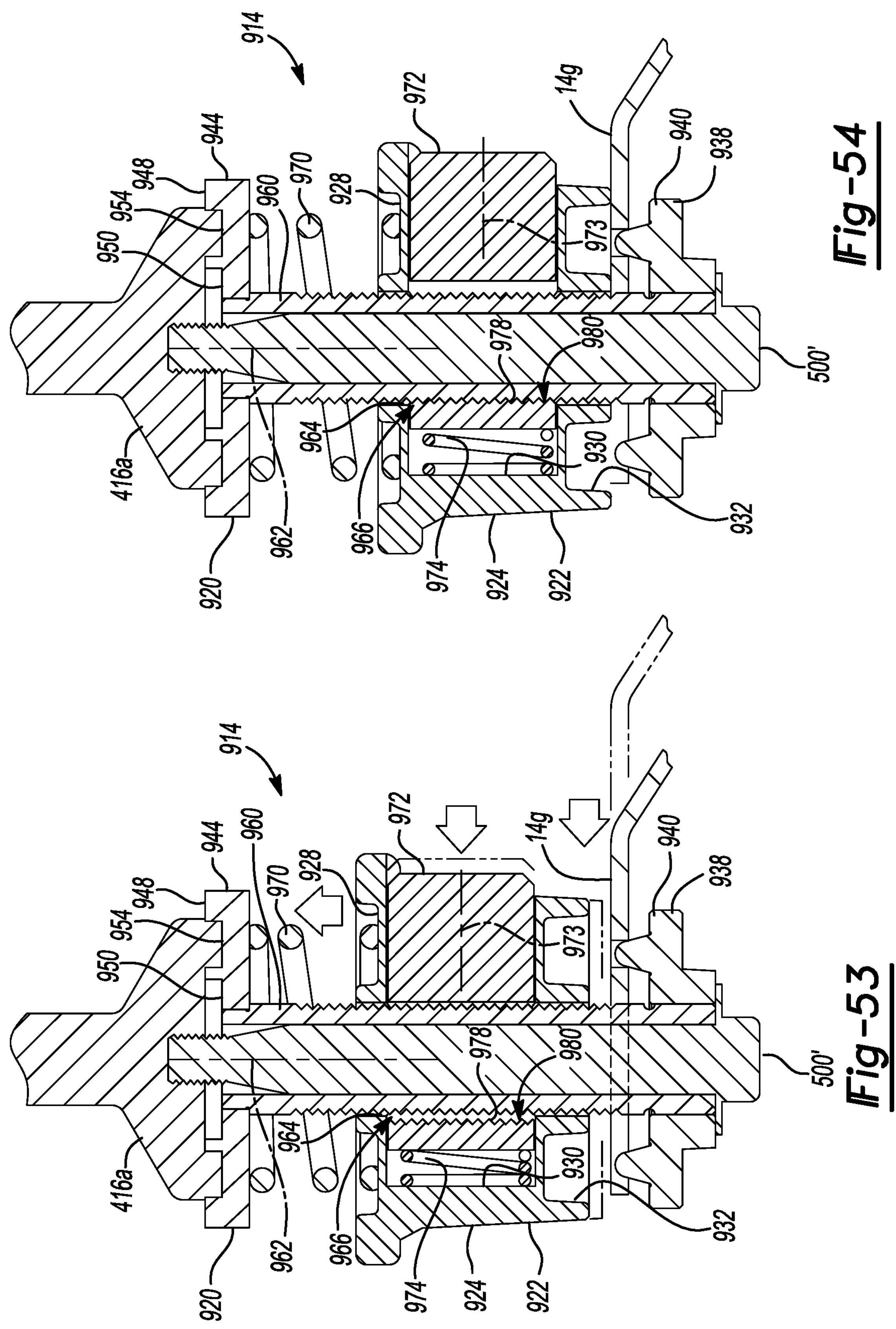
FIG. 53 is a cross-sectional view of the clamp assembly of FIG. 51 and shown with the clamp assembly in the open position for receipt of an accessory.
FIG. 54 is a cross-sectional view of the clamp assembly of FIG. 53 and shown with the clamp assembly in the closed position for clamping the accessory between the first and second clamp member.

With reference now to FIGS. 51-54, a clamp arrangement constructed in accordance to another example of the present disclosure is shown and generally identified at reference numeral 910. The clamp arrangement 910 is shown generally associated with a first output member 416*a* (FIG. 53) of the first power tool 412*a* (FIG. 40). As will become understood from the following discussion, the clamp assembly 910 includes a clamp assembly 914 that is configured to be selectively coupled to the first or second power tools 412*a* and 412*b*. Again, it will be appreciated that the clamp assembly 914 may incorporate additional or alternative geometry for mating with other power tools such as those described herein. The clamp assembly 914 is configured to selectively and alternatively retain various accessories such as the seventh accessory 14*g* (FIGS. 53-54). In this regard, the clamp assembly 914 is configured to be suitably coupled with either of the output member 416*a* provided on the first power tool 412*a* or the output member 416*b* provided on the second power tool 412*b*.

The clamp assembly 914 generally includes an attachment plate 920 having a first clamp member 922 movably coupled thereto. The first clamp member 922 can generally include a first clamp member body 924 that defines a through bore 926 (FIG. 52), an inset 928, a blind bore 930, and a radial channel 932. The first clamp member body 924 includes an annular flange 934. As will be described herein, the annular flange 934 can facilitate a gripping of the user onto the clamp member body 924. A fastener 500' can include threads 504' that threadably mate with corresponding threads defined in the output member 416*a*. The fastener 500' can therefore capture the clamp assembly 914 to the identified power tool.

The first clamp member 922 is configured to translate relative to a second clamp member 938 as will become appreciated from the following discussion. The second clamp member 938 can include a second clamp member body 940. The second clamp body 940 can be generally formed similar to the second clamp body 460 described above and will not be repeated. The attachment plate 920 can generally include an attachment plate body 944 that provides an attachment plate mating detail 946. The attachment plate mating detail 946 can generally comprise a raised annular rim 948 having a central recess 950 and a plurality of receiving portions 952 formed thereon. In the example shown, the raised rim 948 incorporates twelve receiving portions 952 in the form of oval recesses 954. The oval recesses 954 can be configured to selectively receive the protrusions 422*a* provided on the first mating geometry 420*a* of the first power tool 412*a*. Again, the oval recesses 954 can cooperatively mate with protrusions 422*a* having various diameters.

The central recess 950 can be a keyed sidewall 958 defined into the attachment plate body 944. The keyed sidewall 958 can generally be in the form of a twelve point star. In the example provided, the attachment plate 920 further comprises a stem 960 extending therefrom. The stem 960 is shown separately formed from the attachment plate 920 and to the second clamp member 938. However, it is contemplated that the stem 960 can be integrally formed with the attachment plate 920. The stem 960 defines a longitudinal axis 962. A first series of threads 964 can be formed around the stem 960. The first series of threads 964 can collectively define a first gripping detail 966. The first gripping detail 966 can therefore be associated with, or fixed relative to, the second clamp member 938.

Figures 51, 52:
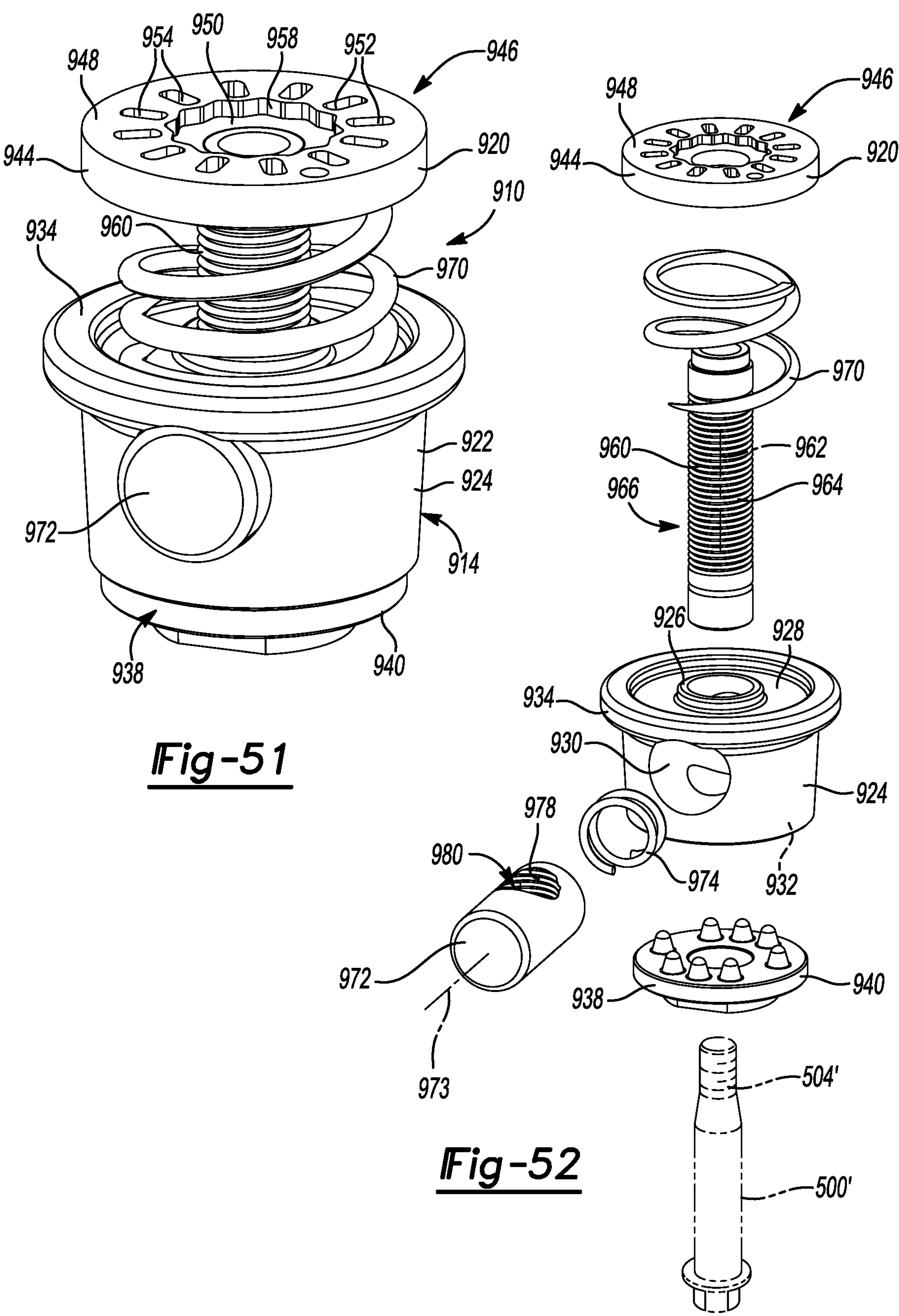
FIG. 51 is a front perspective view of a clamp assembly constructed in accordance to yet another example of the present teachings.
FIG. 52 is an exploded perspective view of the clamp assembly of FIG. 51.

With particular reference now to FIG. 52, additional features of the clamp assembly 914 will be described. A first biasing member 970 can be located generally around the stem 960 and configured for engaging the clamp member body 924 at the inset 928 on one end and the attachment plate 920 on an opposite end. In this regard, the first biasing member 970 can provide a biasing force onto the clamp member body 924 and the direction of the second clamp member 938 or downwardly along the longitudinal axis 962. A button 972 defines a button axis 973 and can be at least partially received into the blind bore 930 of the clamp member body 924 against a bias of a second biasing member 974. The button 972 includes a second series of threads 978 that collectively define a second gripping detail 980.

With particular reference now to FIGS. 53 and 54, operation of the clamp assembly 914 according to one example of the present teachings will be described. At the outset, it will be appreciated that the first series of threads 964 can threadably mate with the second series of threads 978 for locating the button 972 at the desired location along the stem 960. Explained in greater detail, the second biasing member 974 can provide a bias against the button 972 forcing the button 972 in a direction rightward as viewed in FIG. 53 along the button axis 973. In this regard, the second gripping detail 980 of the second series of threads 978 are caused to mate and therefore cooperatively lock with the first gripping detail 966 of the first series of threads 964 on the stem 960. When an operator wishes to change the location of the clamp member body 924, the button 972 can be translated in a direction leftward (as viewed in FIG. 52) along the button axis 973 against the bias of the second biasing member 974. In this regard, the first series of threads 964 and the second series of threads 978 are caused to disengage whereby the operator can subsequently translate the clamp member body 924 in a direction along the axis 962 of the stem 960. Once the desired elevation has been achieved, the operator can release the button 972 causing the respective first and second series of threads 964 and 978 to lock. Alternatively, an operator may rotate the first clamp member body 924 in a direction generally around the longitudinal axis 962 causing the first clamp member 922 to threadably advance along the first series of threads 964 to a desired position.

At this time, the user can place the desired accessory between the first and second clamp members 922 and 938. Next, the user can again depress the button 972 allowing the first biasing member 970 to direct the clamp member body 924 in a direction toward the accessory 14*g* until the accessory 14*g* is suitably clamped between the first and second clamp members 822 and 838. Again, a user may alternatively rotate the first clamp member body 924 to move the first clamp member 922 into a position that suitably clamps the accessory 14*g* between the first and second clamp members 922 and 938, respectively. Notably, in the configuration of the clamp assembly 914, a user can optionally further rotate the clamp member body 924 in a direction around the axis 962 causing the first and second series of thread portions 964 and 978 to engage whereby the user can further translate the first clamp member body 924 toward the second clamp member 938. Such a configuration may be particularly advantageous for aggressive applications where it may be desired to provide an increased clamping force onto an accessory.

Figure 55:
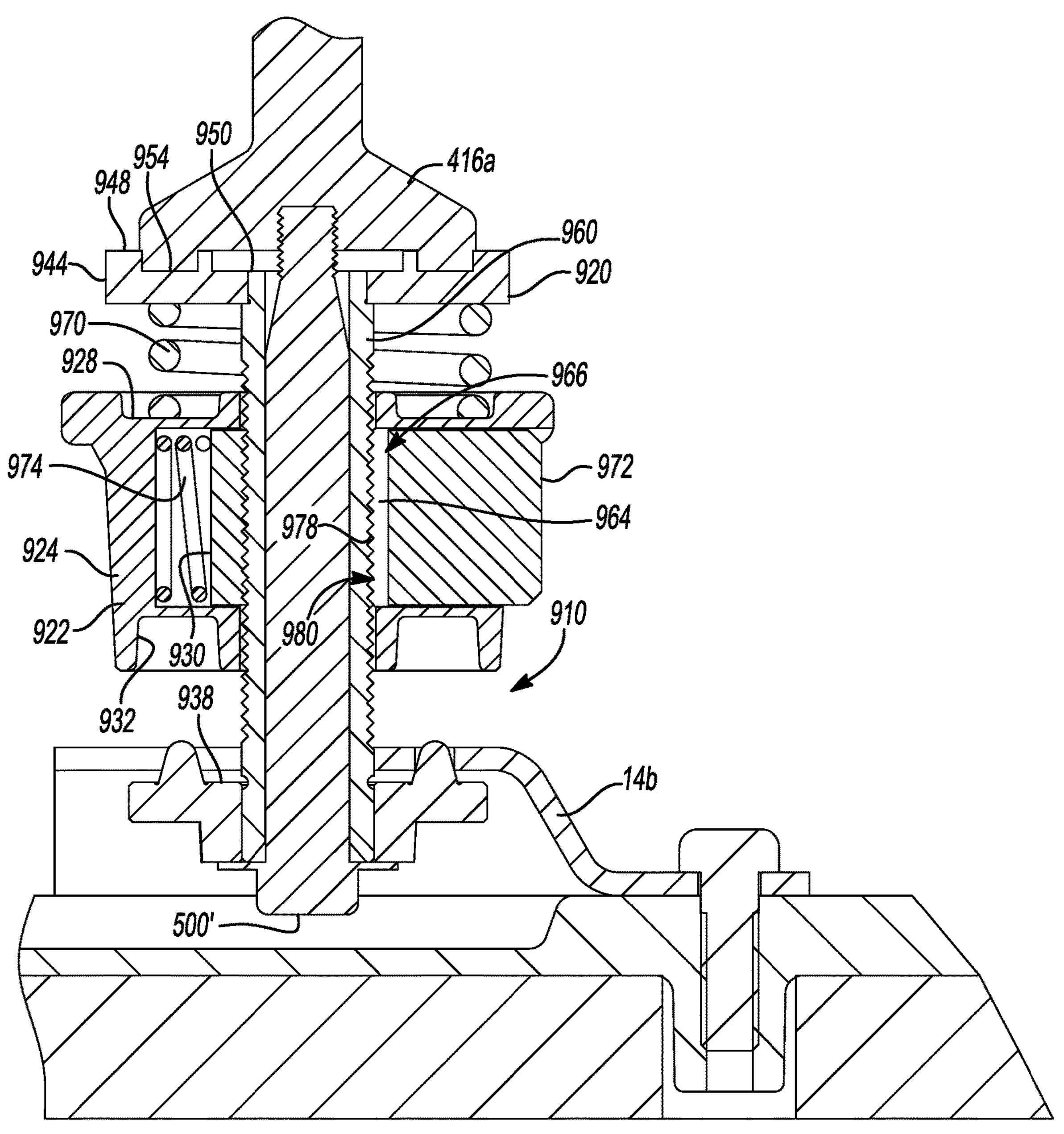
FIG. 55 is a cross-sectional view of clamp assembly constructed in accordance to other examples of the present teachings and shown in an open position for receipt of an accessory in the form of a sanding platen.
Figure 56:
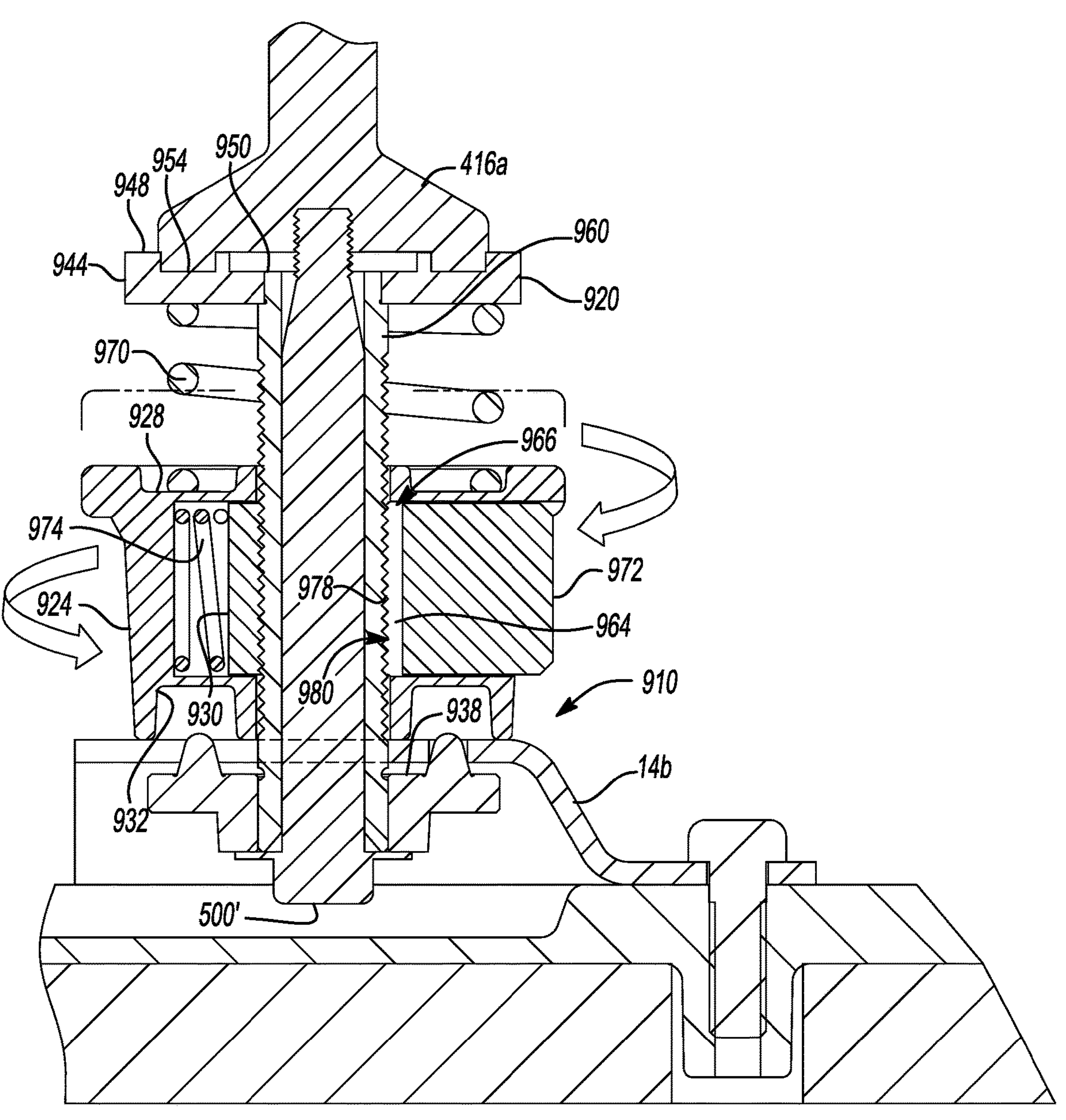
FIG. 56 is a cross-sectional view of the clamp assembly of FIG. 55 and shown with the clamp assembly in the closed position and clamping the accessory between the first and second clamp member.

With reference now to FIGS. 55 and 56, the clamp arrangement 910 is shown operatively clamping an accessory 14*b* in the form of a sanding platen. The accessory 14*b* can be suitably clamped between the first and second clamp members 922 and 938. Again, the first clamp member body 924 can be rotated around the stem 960 to provide a tighter clamping force onto the accessory 14*b*.

With reference now to FIGS. 57-59 and 61-70, a clamp arrangement constructed in accordance to another example of the present disclosure is shown and generally identified at reference numeral 1010. The clamp arrangement 1010 can be selectively and alternatively coupled to various power tools such as the first or second power tools 412*a* and 412*b* described above (FIG. 35). The clamp arrangement 1010 generally includes a clamp assembly 1014 that may be configured to selectively and alternatively retain various accessories such as the seventh accessory 14*g* (FIG. 43).

Figures 57, 58:
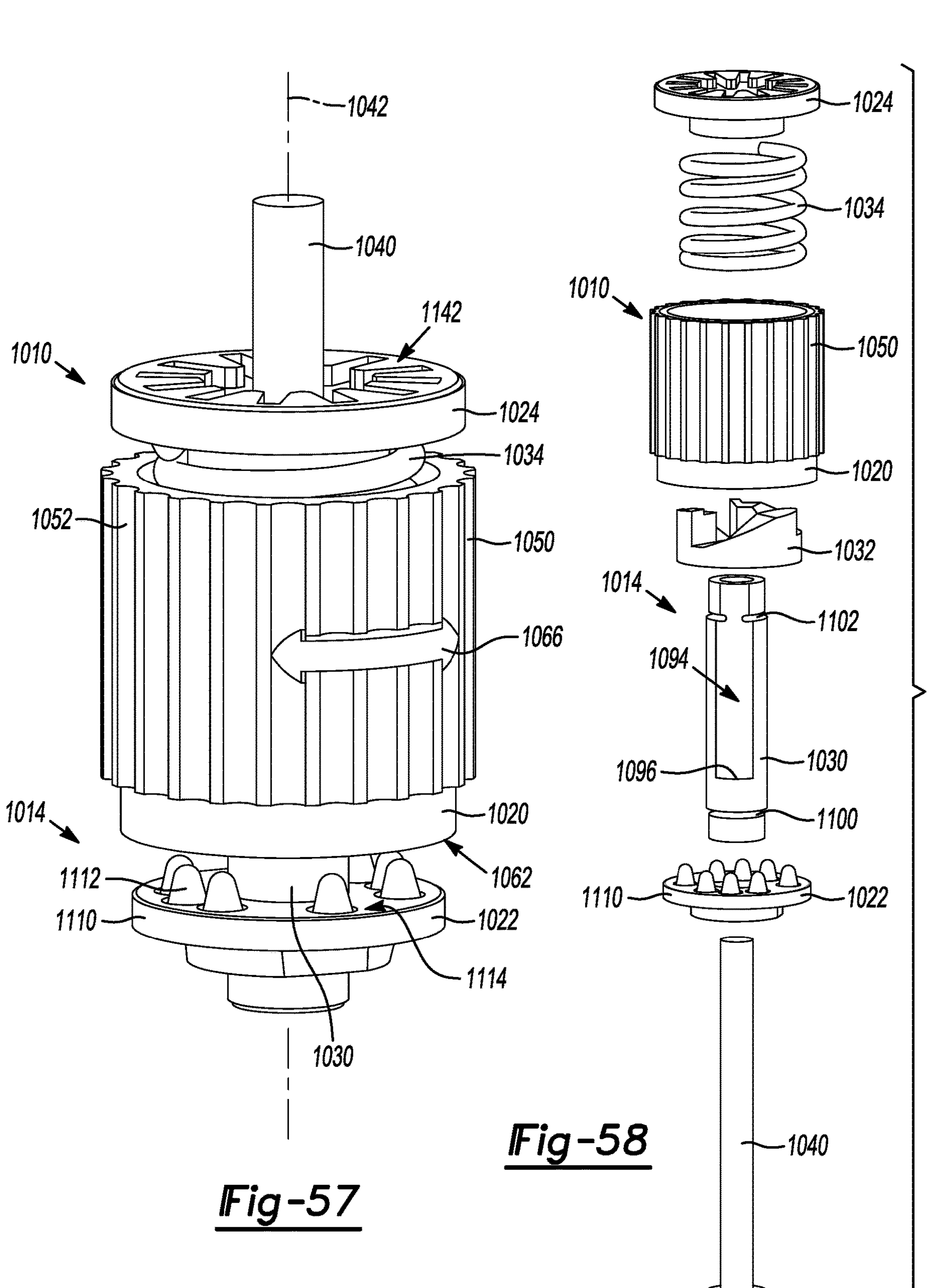
FIG. 57 is a front perspective view of a clamp assembly constructed in accordance to another example of the present teachings and with the clamp assembly shown in an open position.
FIG. 58 is an exploded perspective view of the clamp assembly of FIG. 57.
Figures 59, 60:
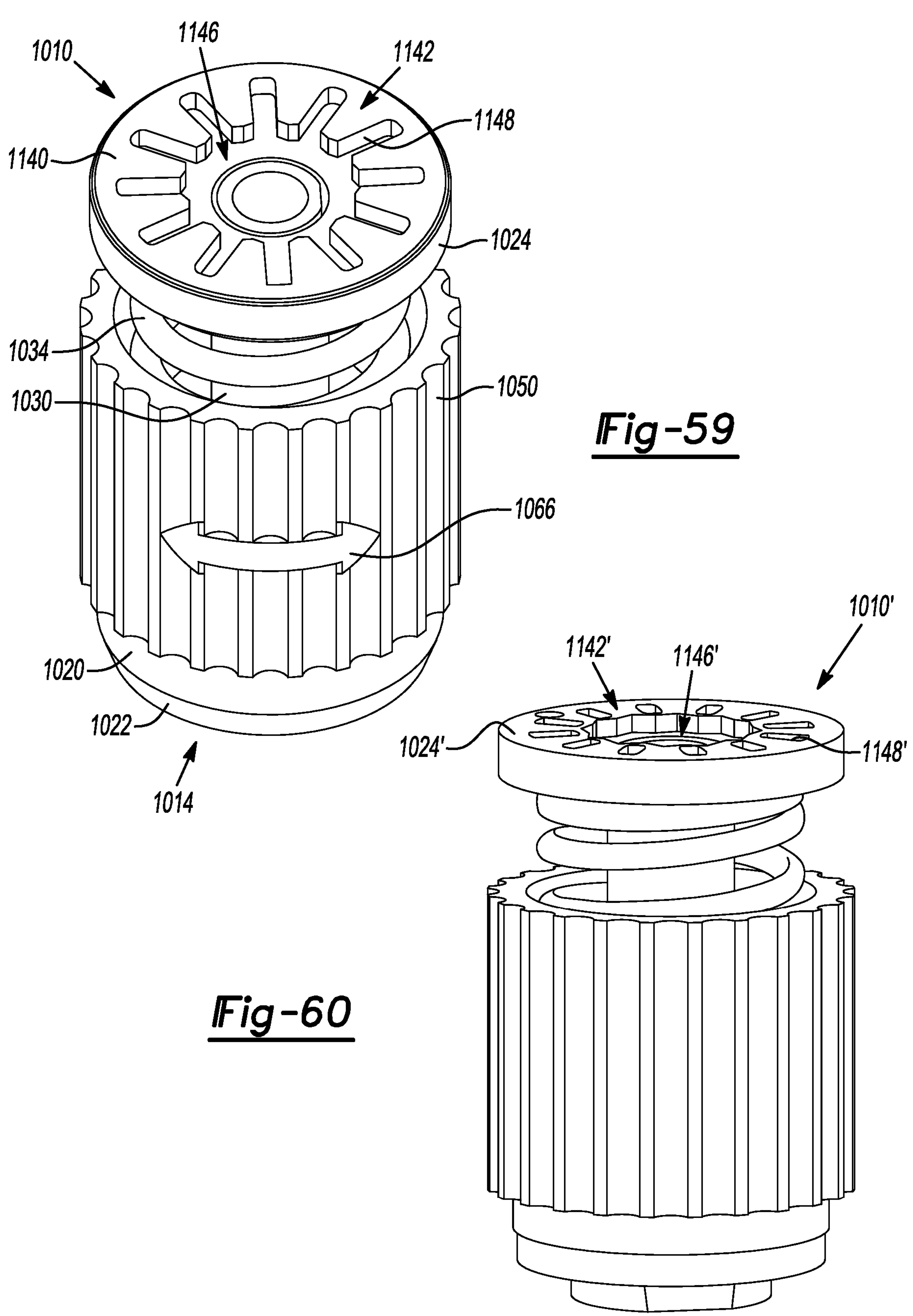
FIG. 59 is a front perspective view of the clamp assembly of FIG. 57 and shown in a closed position.
FIG. 60 is a front perspective view of a clamp assembly having an alternate attachment plate and shown in the closed position.
Figures 68, 69, 70:
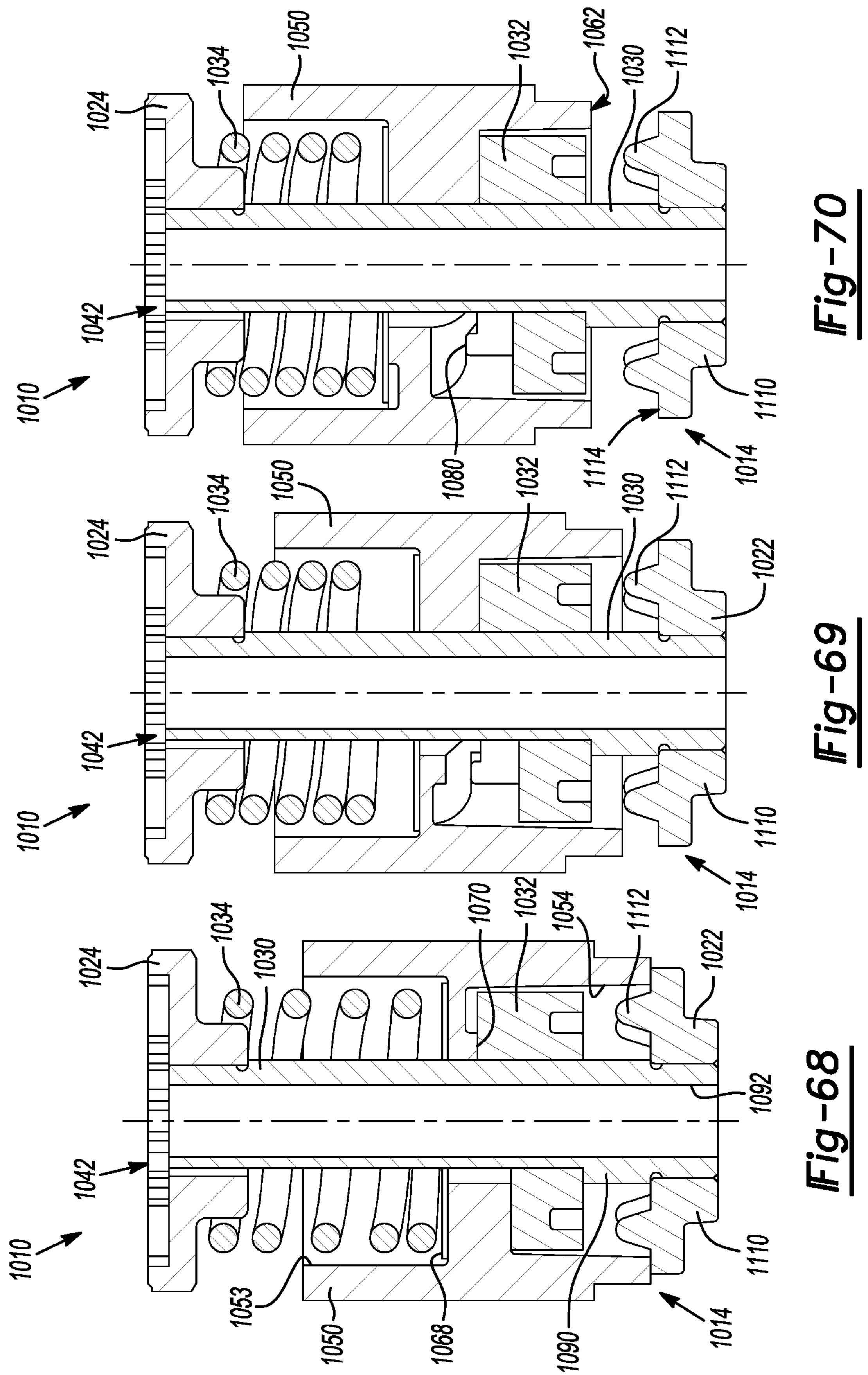
FIG. 68 is a sectional view of the clamp assembly of FIG. 57 and shown in a closed position.
FIG. 69 is a sectional view of the clamp assembly of FIG. 57 and shown in an intermediate position.
FIG. 70 is a sectional view of the clamp assembly of FIG. 57 and shown in an open position.

Referring to FIG. 58, the clamp assembly 1014 generally includes a first clamp member 1020, a second clamp member 1022, an attachment plate 1024, a stem 1030, a cam body 1032, a biasing member 1034, and a fastener 1040. As will be appreciated from the following discussion, the first clamp member 1020 is configured to translate along an axis 1042 of the fastener 1040 relative to the second clamp member 1022 upon rotation of the first clamp member 1020. In this regard, rotation of the first clamp member 1020 in a first direction can cause the first clamp member 1020 to translate toward the second clamp member 1022 into a closed or clamped position (FIGS. 59 and 68). Similarly, rotation of the first clamp member 1020 in a second, opposite direction can cause the first clamp member 1020 to translate away from the second clamp member 1022 into a fully open or unclamped position (FIGS. 57 and 70).

Figures 61, 62, 63:
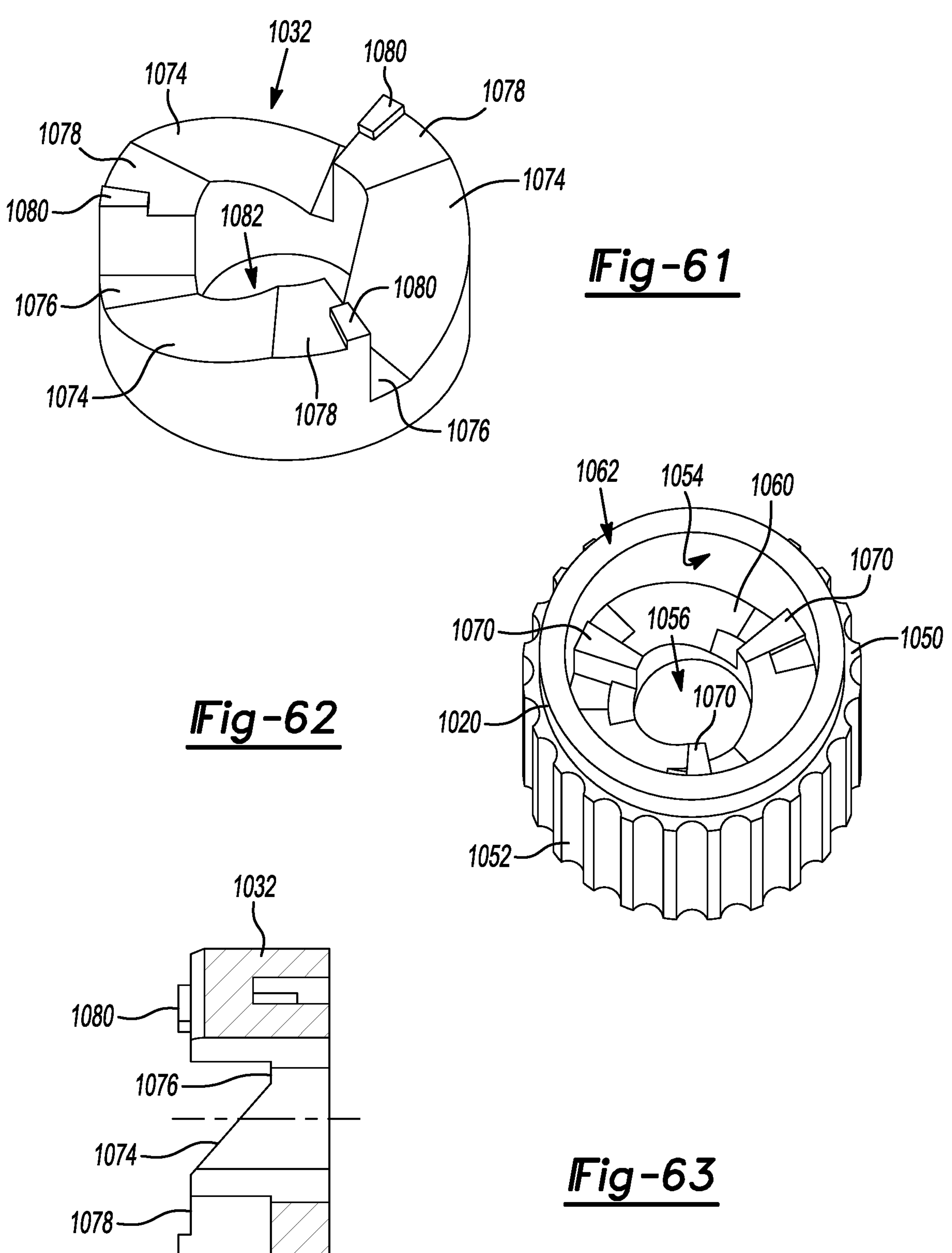
FIG. 61 is a front perspective view of a cam body of the clamp assembly of FIG. 57.
FIG. 62 is a perspective view of a first clamp member body of the clamp assembly of FIG. 57.
FIG. 63 is a sectional view of the cam body of FIG. 61.
Figure 64:
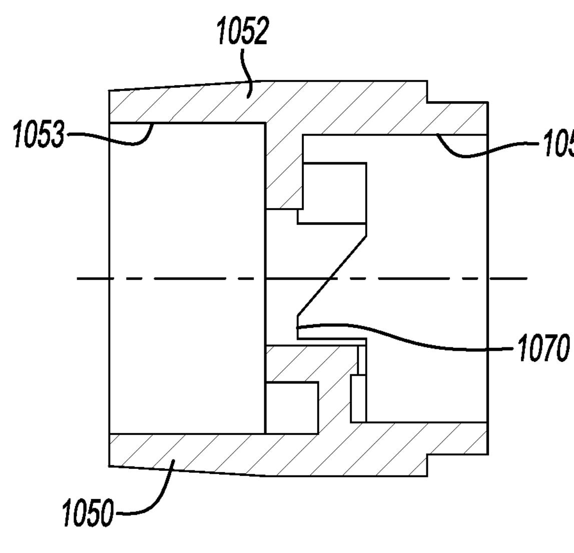
FIG. 64 is a sectional view of the first clamp member body of FIG. 62.
Figure 65:
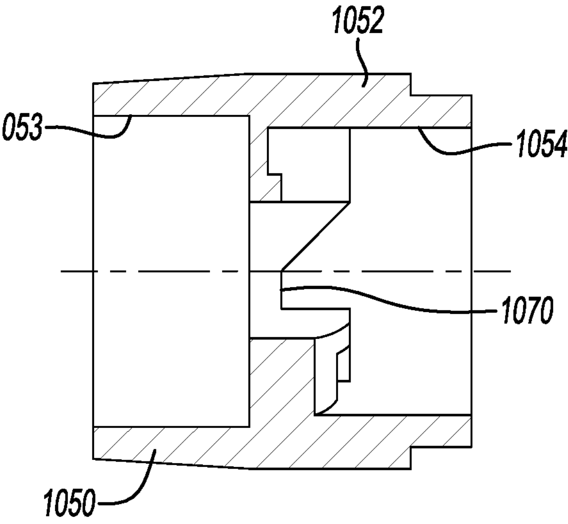
FIG. 65 is another sectional view of the clamp member body of FIG. 62.
Figure 66:
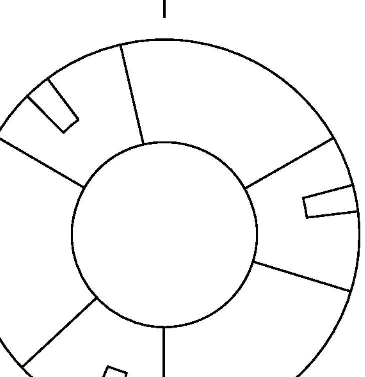
FIG. 66 is a plan view of the cam body of FIG. 61.
Figure 67:
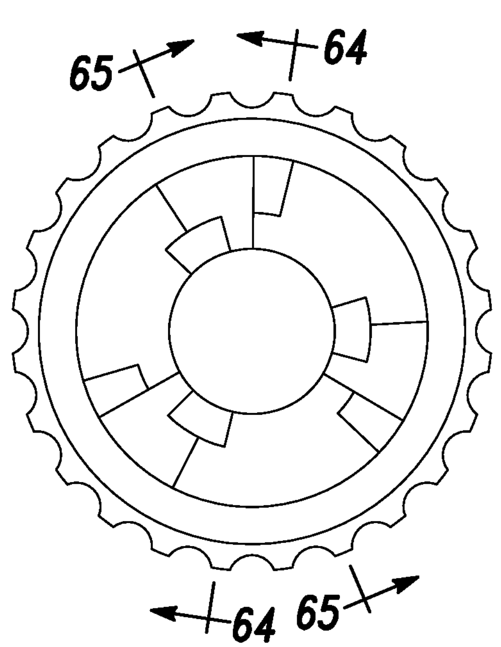
FIG. 67 is a plan view of the first clamp member body of FIG. 62.
Figure 67:
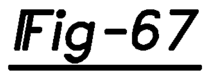

With particular reference to FIGS. 58 and 62, the first clamp member 1020 can include a first clamp member body 1050 that generally includes an outer ribbed gripping surface 1052, an upper recess 1053 (FIG. 68), a lower recess 1054 (FIG. 62), a central opening 1056, a cam follower body 1060, and a clamping surface 1062. The gripping surface 1052 can further include a double-ended arrow identifier 1066 that points in directions generally transverse to the axis 1042 to indicate to the user that the first clamp member body 1050 is configured to be rotated around the axis 1042. The lower recess 1054 can be sized to receive the cam body 1032 (see also FIGS. 68-70). The lower recess 1054 can also be sized to at least partially receive portions of the second clamp member 1022 in the closed or clamped position (FIG. 68). The upper recess 1053 can receive a portion of the biasing member 1034. In one configuration, the biasing member can be mounted for compression between the attachment plate 1024 and a terminal end 1068 of the upper recess 1053.

The cam follower body 1060 can generally include a plurality of cam pawls 1070. As will be described below, the cam pawls 1070 of the cam follower body 1060 are configured to slidably negotiate along features of the cam body 1032 to influence the first clamp member body 1050, and therefore the first clamp member 1020, to translate along the axis 1042 (FIG. 57) relative to the second clamp member 1022.

With particular reference now to FIGS. 58, 61, and 63, the cam body 1032 will be described in greater detail. The cam body 1032 generally includes a plurality of cam ramps 1074 that are positioned between respective cam valleys and cam plateaus 1076 and 1078. Each of the cam plateaus 1078 can further include a cam stop 1080 formed thereon. The cam body 1032 can further include an opening 1082 therein. The cam body 1032 can further include a planar mounting surface 1084 (FIG. 66) that, together with the opening 1082, is configured to provide a keyway for non-rotatably receiving the stem 1030. As can be appreciated, the cam pawls 1070 of the cam follower body 1060 are configured to slidably negotiate around the respective cam ramps 1074 between the cam plateaus 1078 (corresponding to the clamp assembly 1014 being in an open position FIG. 70) and a position on or near the cam valleys 1076 (corresponding to the clamp assembly 1014 being in a closed or clamped position, FIG. 68). It will be appreciated that while three cam pawls 1070 and cam ramps 1074 have been incorporated on the clamp assembly 1014, other configurations are contemplated.

Referring now to FIGS. 58 and 68-70, the stem 130 will be further described. The stem 130 generally includes a cylindrical body 1090 that defines a throughbore 1092. The stem 1030 further includes a flat 1094 (FIG. 58) formed on the body 1090. The flat 1094 incorporates a ledge 1096 at a terminal end thereof. The stem 1030 further includes a distal seat 1100 and a proximal seat 1102. The second clamp member 1022 can be fixedly and non-rotatably secured to the stem 1030 at the distal seat 1100. Similarly, the attachment plate 1024 can be fixedly and non-rotatably secured to the stem 1030 at the proximal seat 1102. The planar mounting surface 1084 (FIG. 66) of the cam body 1032 can locate against the flat 1094 such that the cam body 1032 is non-rotatably fixed to the stem 1030 at the ledge 1096. It is appreciated that once assembled, the cam body 1032 is further precluded from translating along the stem 1030.

The second clamp member 1022 can include a second clamp member body 1110 having a plurality of mounting features 1112 extending therefrom. The mounting features 1112 can be generally in the form of male conical protrusions such as the male conical protrusions 258 described in detail above with respect to FIG. 31. According to one example, the male conical protrusions of the mounting features 1112 can be configured to engage apertures of an accessory. By way of example, the mounting features 1112 can be configured to engage apertures of the sixth accessory **14*f* at a position intermediate the terminal end of the tips and a second clamp surface 1114 on the second clamp member 1022 such as described above with respect to FIG. 30**.

With particular reference now to FIG. 59, the attachment plate 1024 can generally include an attachment plate body 1140 that provides an attachment plate mating detail 1142. The attachment plate mating detail 1142 can generally comprise an annular rim 1144 having a central recess 1146 and a plurality of receiving portions 1148 formed thereon. In the example provided, the rim 1144 incorporates twelve receiving portions 1148 in the form of oblong recesses that extend into and connect with the central recess 1146. As can be appreciated, the oblong recesses can be configured to selectively receive protrusions provided on a first power tool (such as the first power tool **412*a*, FIG. 35). Alternatively, the central recess 1146 can be configured to receive the corresponding mating geometry of a second power tool (such as the second power tool 412*b*, FIG. 35**).

In one example of coupling the clamp arrangement 1010 to a first power tool (such as the first power tool **412*a*, FIG. 35), a user may initially align the attachment plate mating detail 1142 defined in the attachment plate body 1140 for receipt of the complementary circular protrusions (such as protrusions 422*a*, FIG. 35). Once the protrusions of the power tool are selectively received by the receiving portions 1148 in the attachment plate 1140, the clamp assembly 1014 is rotationally fixed with the output member of the tool. Next, a user may advance the fastener 1040 through the throughbore 1092 defined through the stem 1030. The fastener 1040 can be fixedly coupled to the output member of the tool such as by threads formed on a distal end of the fastener 1040 (not specifically shown). FIG. 60 illustrates a clamping arrangement 1010'. The clamping arrangement 1010' is constructed similar to the clamping arrangement 1010 described above except an attachment plate 1024' provides a mating detail 1142' that includes a plurality of receiving portions 1148' that do not intersect with a central recess 1146'. The mating detail 1142' may be constructed similar to the mating detail 686 described above and shown in FIG. 40**.

With specific reference now to FIGS. 68, 70, operation of the clamp assembly 1014 according to one example of the present disclosure will now be described. As can be appreciated, the biasing member 1034 normally biases the first clamp member 1020 toward and into engagement with the second clamp member 1022. To move the first clamp member 1020 from the closed position (FIG. 68) toward an open position (FIG. 70), a user can rotate the first clamp member 1020 in a first direction (counter-clockwise as viewed in FIG. 58). Rotation of the first clamp member 1020 in the first direction will cause the respective cam pawls 1070 to slidably negotiate from a position generally on or adjacent to the cam valleys 1076 on the cam body 1032 along the cam ramps 1074 (FIG. 61). As the cam body 1032 is fixed relative to the stem 1030, the cam pawls 1070 ride up the respective cam ramps 1074 thereby causing the first clamp member 1020 to move away from the second clamp member 1022 (or in a direction up as viewed from FIG. 68 to FIG. 78). The first clamp member 1020 can continue to rotate until the cam pawls 1070 locate onto the respective cam plateaus 1078 (FIG. 61) on the cam body 1032. Engagement of the respective cam pawls 1070 with the cam stops 1080 will preclude further rotation of the first clamp member 1020 conveying to a user that the first clamp member body 1050 has reached a fully open position (FIG. 70). With the clamp assembly 1014 in the open position, a user may insert or replace an accessory. In this regard, once the desired accessory has been located between the first and second clamp members 1020 and 1022, respectively, a user can rotate the first clamp member body 1050 in a second opposite direction (clockwise as viewed in FIG. 58). Rotation of the first clamp member body 1050 in the second direction will cause the cam pawls 1070 to ride down the respective cam ramps 1074 to a position that allows an accessory to be clamped between the mounting features 1112 and the clamping surface 1062 of the first clamp member 1020. Again, the biasing member 1034 will tend to facilitate and encourage movement of the cam pawls 1070 down the cam ramps 1074 and into a clamping position.

Figures 71, 72:
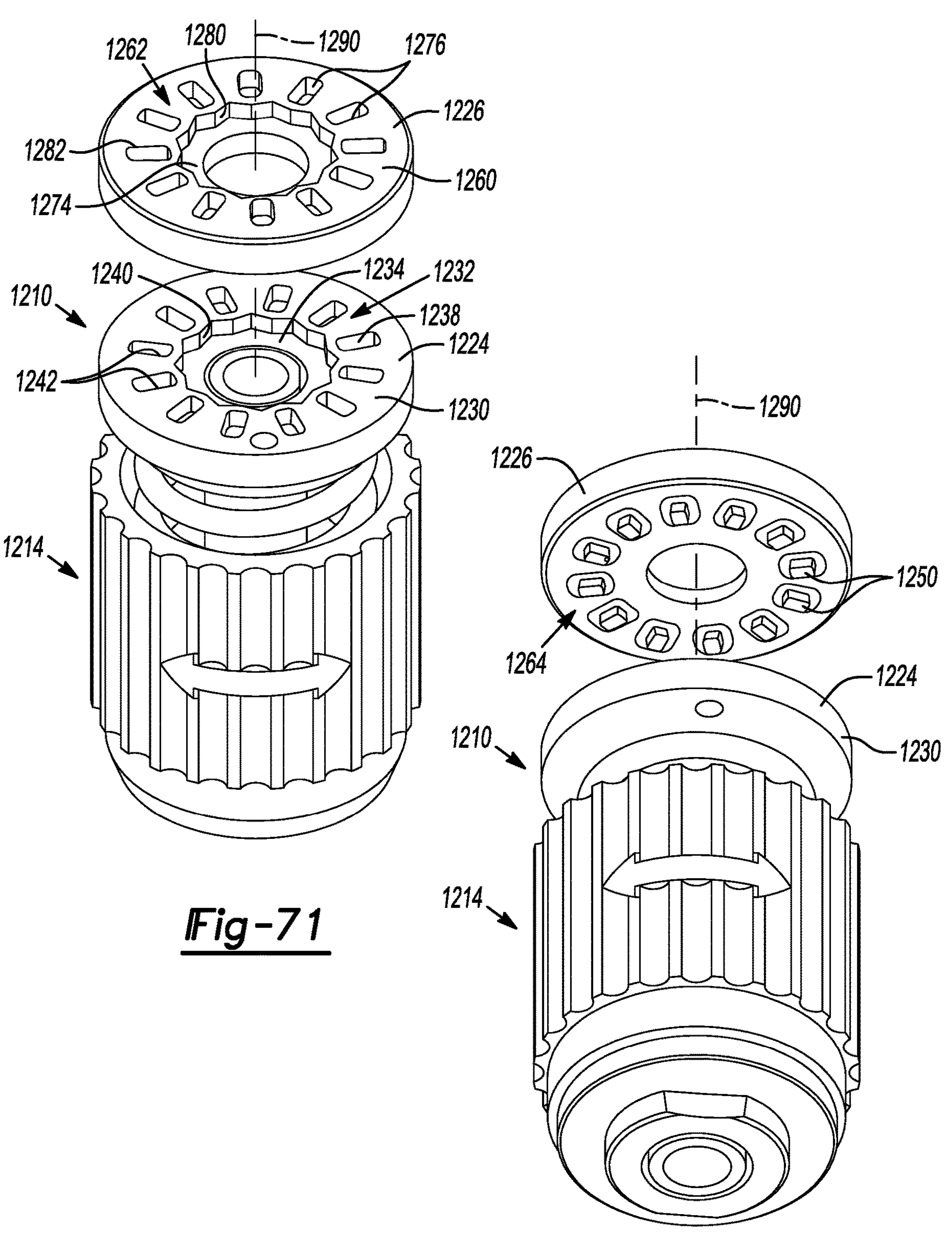
FIG. 71 is a top perspective view of a clamp arrangement constructed in accordance to additional features of the present disclosure.
FIG. 72 is a bottom perspective view of the clamp arrangement of FIG. 71.

With reference now to FIGS. 71 and 72, a clamp arrangement constructed in accordance to another example of the present disclosure is shown and generally identified at reference numeral 1210. The clamp arrangement 1210 can be selectively and alternatively coupled to various power tools such as the first or second power tools 412*a* and 412*b* described above (FIG. 35). The clamp arrangement 1210 generally includes a clamp assembly 1214 that may be configured to selectively and alternatively retain various accessories such as described herein. Unless otherwise described, the clamp assembly 1214 may be constructed similar to the clamp assembly 1014 described above. Therefore, the description and operation of the clamp assembly 1214 will not be repeated here.

The clamp arrangement 1210 generally includes an attachment plate 1224 and a floating adapter plate 1226. As will be described herein, the floating adapter plate 1226 can be optionally incorporated between the attachment plate 1224 and an identified tool when it is desired to rotate the orientation of the clamp assembly 1214 relative to the tool. The attachment plate 1224 can generally include an attachment plate body 1230 that provides an attachment plate mating detail 1232. The attachment plate mating detail 1232 can generally comprise a central recess 1234 and a plurality of receiving portions 1238 arranged therearound. The central recess 1234 can be further defined by a keyed sidewall 1240 defined into the body 1230. The keyed sidewall 1240 can generally be in the form of a twelve point star. The plurality of receiving portions 1238 can be generally defined into the body 1230 as oval recesses 1242. The oval recesses 1242 can be configured to selectively receive the protrusions 422*a* (FIG. 35) provided on the first mating geometry 420*a* of the first power tool 412*a*. Alternatively, and as will be described below, the oval recesses 1242 can be configured to receive protrusions 1250 (FIG. 72) extending from the floating adapter plate 1226.

The floating adapter plate 1226 can generally include a floating adapter plate body 1260 that provides an upper mating detail 1262 (FIG. 71) and a lower mating detail 1264 (FIG. 72). The upper mating detail 1262 can generally comprise a central recess 1274 and a plurality of receiving portions 1276. In the example provided, the central recess 1274 can be generally defined by a keyed sidewall 1280 defined into the body 1260. The keyed sidewall 1280 can be generally in the form of a twelve point star. The plurality of receiving portions 1276 can be generally defined into the body 1260 as oval recesses 1282. The lower mating surface 1264 includes the protrusions 1250. Of note, when the floating adapter plate 1226 is assembled between the adapter plate 1224 and the identified power tool, the protrusions 1250 on the floating adapter plate 1226 are received into the receiving portions 1238. The orientation of the receiving portions 1276 on the floating attachment plate 1226 are rotated relative to the receiving portions 1238 on the attachment plate 1224. As a result, the orientation of the clamp member 1214 (and the resulting accessory) can be rotated around a central axis 1290 relative to the power tool a predetermined amount. In the example provided, the receiving portions 1238 of the attachment plate 1230 are rotatably offset about fifteen degrees relative to the receiving portions 1276 in the floating adapter plate 1226. Other configurations are contemplated.

Figures 73, 74:
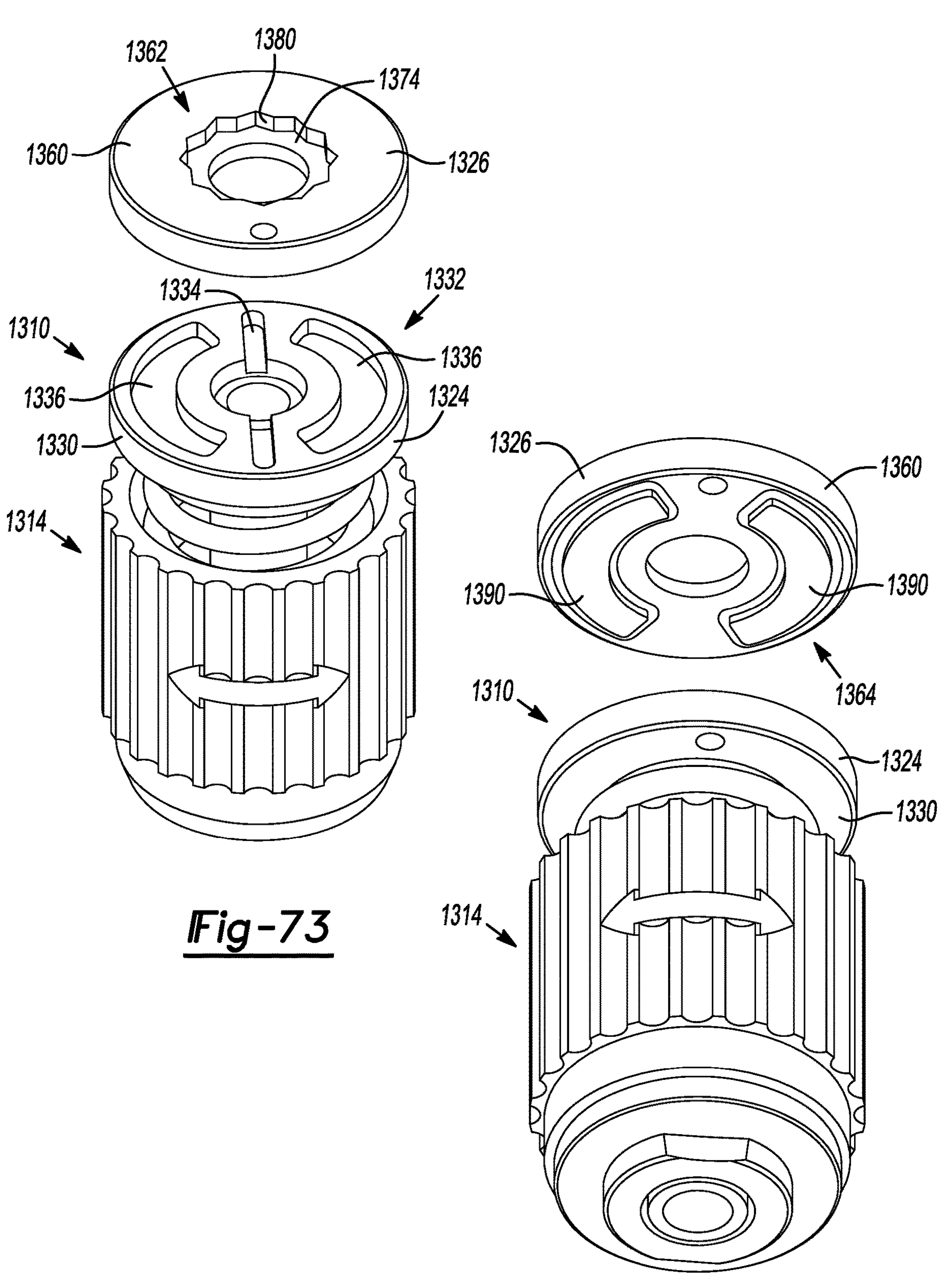
FIG. 73 is a top perspective view of a clamp arrangement constructed in accordance to other features of the present disclosure.
FIG. 74 is a bottom perspective view of the clamp arrangement of FIG. 73.

With reference now to FIGS. 73 and 74, a clamp arrangement constructed in accordance to another example of the present disclosure is shown and generally identified at reference numeral 1310. The clamp arrangement 1310 can be selectively and alternatively coupled to various power tools such as the first or second power tools 412*a* and 412*b* described above (FIG. 35). The clamp arrangement 1310 generally includes a clamp assembly 1314 that may be configured to selectively and alternatively retain various accessories such as described herein. Unless otherwise described, the clamp assembly 1314 may be constructed to the clamp assembly 1014 described above. Therefore, the description and operation of the clamp assembly 1314 will not be repeated here.

The clamp arrangement 1310 generally includes an attachment plate 1324 and a floating adapter plate 1326. As will be described herein, the floating adapter plate 1326 can be optionally incorporated between the attachment plate 1324 and an identified tool when it is desirable to provide a different mating detail. The attachment plate 1324 can generally include an attachment plate body 1330 that provides an attachment plate mating detail 1332. The attachment plate mating detail 1332 can generally comprise an elongated slot 1334 and a pair of female arcuate slots 1336 formed into the body 1330. In one example, the configuration of the mating detail 1332 can cooperatively mate with the first mating detail 420*a* (FIG. 35) of the first power tool 412*a*. Other configurations are contemplated. When it may be desirable to mate with the second mating geometry 420*b* (FIG. 35) of the second power tool 412*b*, the floating adapter plate 1326 may be positioned between the attachment plate 1324 and the second power tool 412*b*.

The floating adapter plate 1326 can generally include a floating adapter plate body 1360 that provides an upper mating detail 1362 (FIG. 73) and a lower mating detail 1364 (FIG. 74). The upper mating detail 1362 can generally comprise a central recess 1374 that defines a keyed sidewall 1380 defined into the body 1360. The keyed sidewall 1380 can generally be in the form of a twelve point star. The upper mating detail 1362 can be configured to selectively mate with the second mating geometry 420*b* of the second power tool 412*b* (FIG. 35). The lower mating surface 1364 includes male arcuate protrusions 1390 that are configured to be selectively received by the female arcuate slots 1336 (FIG. 73) provided in the adapter plate 1324. The interaction of the male arcuate protrusions 1390 on the floating adapter plate 1326 with the female arcuate slots 1336 on the adapter 1324 non-rotatably fixes the attachment plate 1324 to the floating adapter plate 1326.

Figure 75:
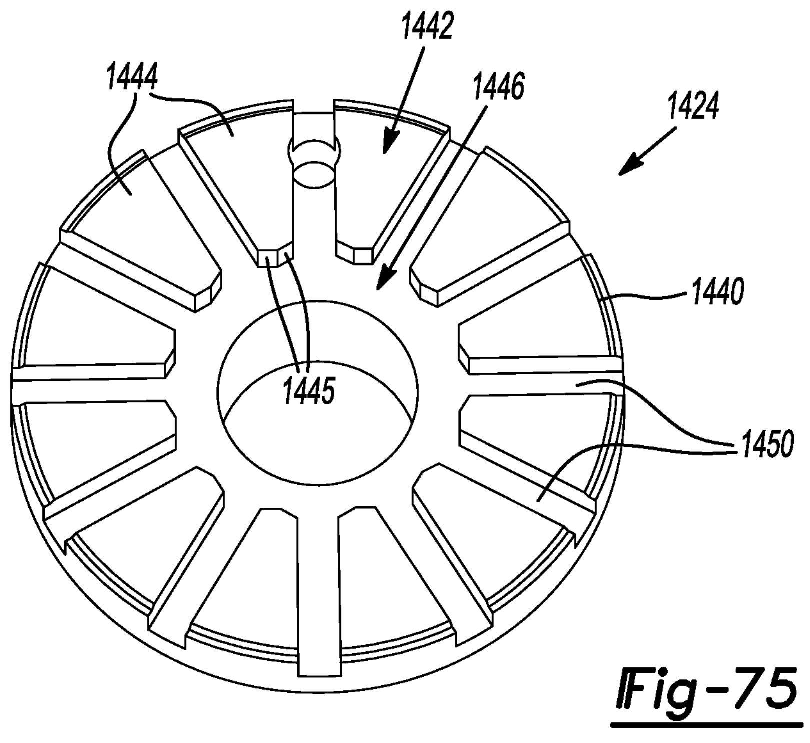
FIG. 75 is a perspective view of an alternate attachment plate according to the present disclosure.

Referring now to FIG. 75, an attachment plate constructed in accordance to additional features of the present disclosure is shown and generally identified at reference numeral 1424. The attachment plate 1424 can be used in place of any of the attachment plates described above. The attachment plate 1424 can generally include an attachment plate body 1440 that provides an attachment plate mating detail 1442. The attachment plate mating detail 1442 can generally comprise a plurality of generally pie-shaped protrusions 1444 that cooperate to form a central recess 1446. Each of the pie-shaped protrusions 1444 includes a pair of converging flats 1445. The flats 1445 can be used to engage and rotatably fix to a corresponding structure extending from a given power tool. A plurality of grooves 1450 are defined on the attachment plate body 1440 between adjacent pie-shaped protrusions 1444. The protrusions 1444, the flats 1445, the central recess 1446 and the grooves 1450 can individually or in combination interface with various attachment details provided on various power tools such as those disclosed herein.

Figure 76:
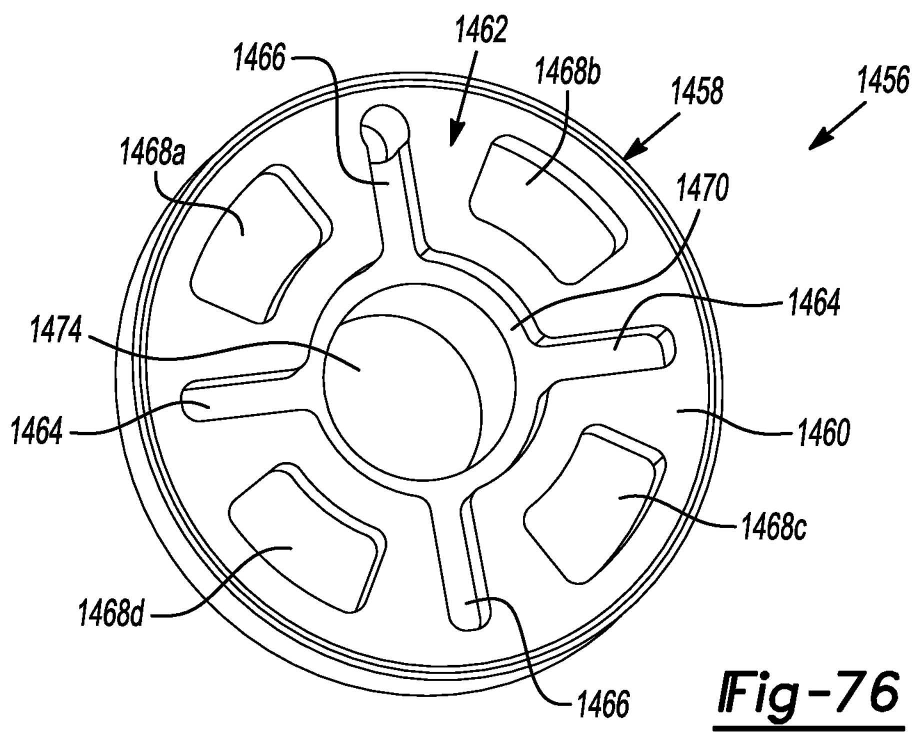
FIG. 76 is a perspective view of an alternate attachment plate according to the present disclosure.

Referring now to FIG. 76, an attachment plate constructed in accordance with additional features of the present disclosure is shown and generally identified at reference numeral 1456. The attachment plate 1456 can be substituted for any of the attachment plates described above. The attachment plate 1456 can generally include an attachment plate body 1458 that provides an attachment plate mating detail 1462 and a central aperture 1474. The attachment plate mating detail 1462 can generally comprise a raised annular rim portion 1460 having a plurality of radially spaced arcuate recesses 1468*a-d* formed therein which are separated by a pair of elongated radially extending grooves 1464 and 1466. In the example provided, the grooves 1464 and 1466 extend perpendicular to each other and join a central recess area 1470 immediately surrounding the aperture 1474. In this embodiment of the attachment plate 1456 the outer radial ends of the grooves 1464 and 1466 are closed and therefore do not extend entirely to the outer periphery of the attachment plate body 1458. The raised rim 1460, the arcuate recesses 1468, and the grooves 1464, 1466 can individually or in combination provide a torque transferring interface with various attachment details provided on various power tools such as those disclosed herein.

Figure 77:
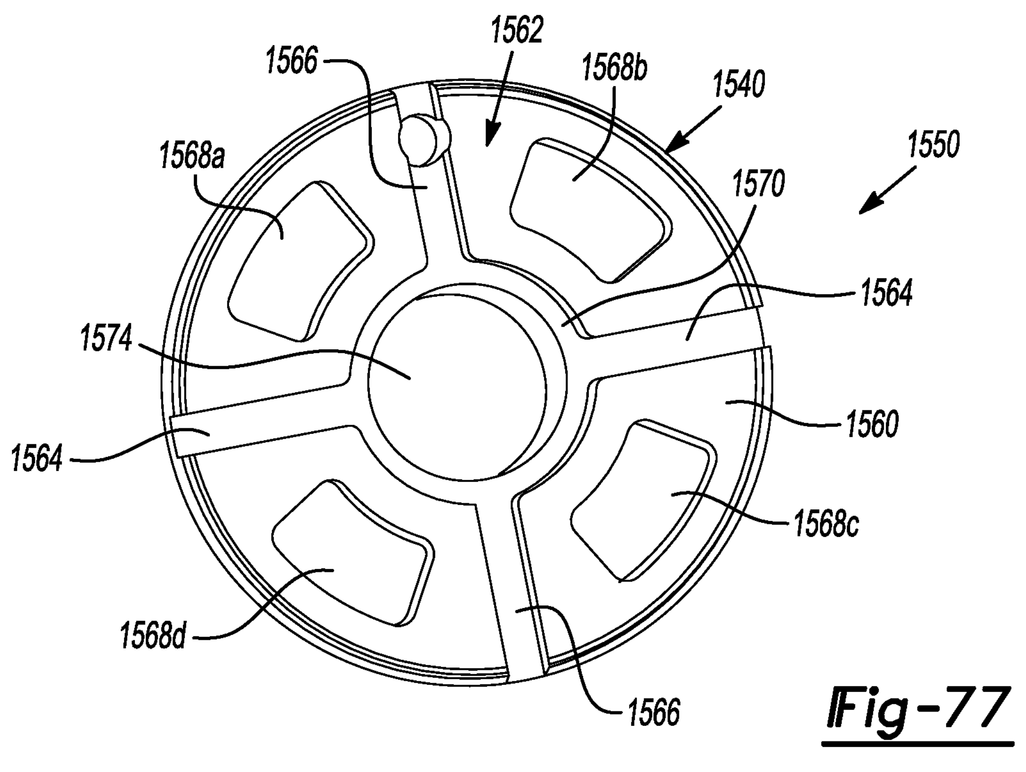
FIG. 77 is a perspective view of an alternate attachment plate according to the present disclosure.

Referring now to FIG. 77, an attachment plate constructed in accordance with additional features of the present disclosure is shown and generally identified at reference numeral 1550. The attachment plate 1550 can be substituted for any of the attachment plates described above. The attachment plate 1550 can generally include an attachment plate body 1540 that provides an attachment plate mating detail 1562 similar to the mating detail 1462 of the attachment plate 1456 shown in FIG. 76. In particular, the attachment plate mating detail 1562 can generally comprise a raised annular rim portion 1560 having a plurality of radially spaced arcuate recesses 1568*a-d* formed therein which are separated by a pair of elongated radially extending grooves 1564 and 1566. The grooves 1564 and 15666 are arranged perpendicular to each other and extend from a central recess area 1570 surrounding the central aperture 1574. In this embodiment of the attachment plate 1550, the radial grooves 1564 and 1566 extend to the outer periphery of the attachment plate body 1540. The raised rim portion 1560, the receiving portions 1568*a-d*, and the radial grooves 1564, 1566 can individually or in combination interface with various attachment details provided on various power tools such as those disclosed herein.

In this regard, the attachment plate mating detail 1562 (as well as the mating detail of the various other attachment plates disclosed herein) is suitable for engaging not only the tool mating details 418*a* and 418*b* (FIG. 35) described above, but other tool mating details provided by other manufacturers including but not limited to Fein, Sears (Craftsman), Rockwell, Dremel, Bosch, Milwaukee, Master Mechanic, and Ridgid.

Figure 78:
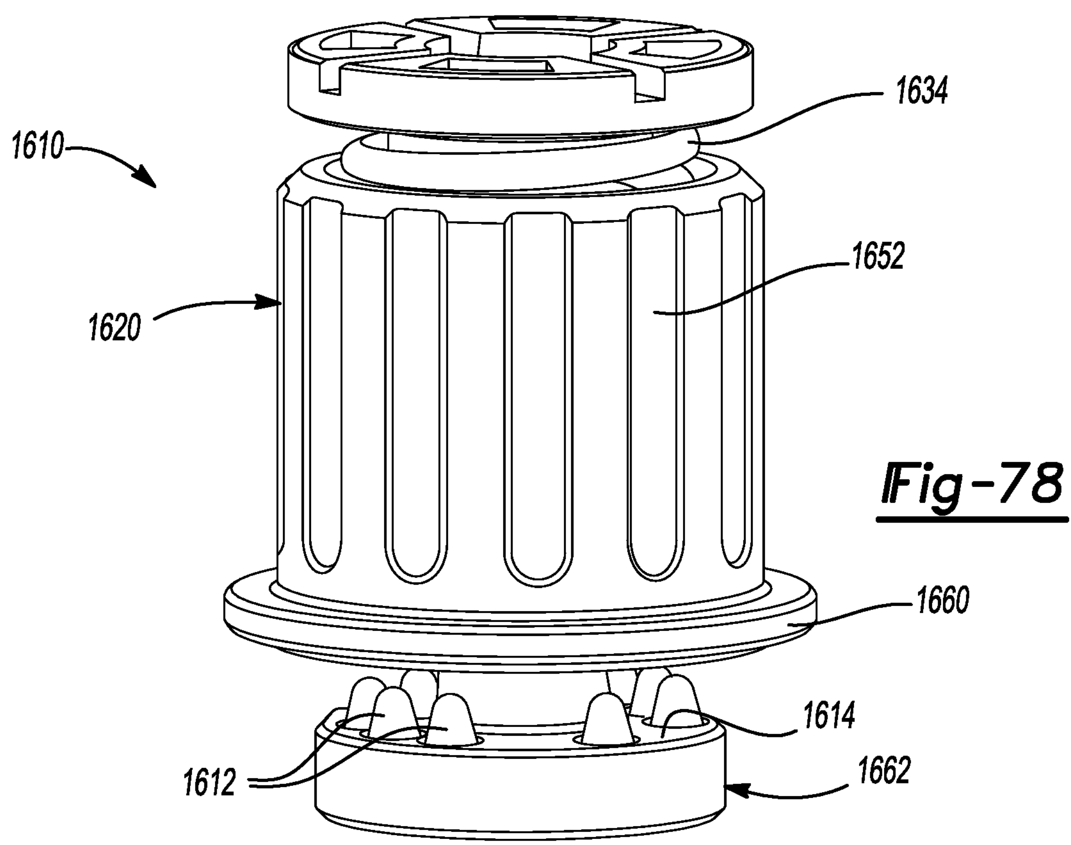
FIG. 78 is a front perspective view of an alternative clamp assembly.

With reference now to FIG. 78, a clamp arrangement constructed in accordance to another example of the present disclosure is shown and generally identified at reference numeral 1610. The clamp arrangement 1610 is similar to the clamp arrangement 1010 shown in FIG. 58 and generally includes a first clamp member 1620, and a second clamp member 1622. The first clamp member 1620 generally includes an outer ribbed gripping surface 1652 for enabling a user to rotate the first clamp member 1620 against the bias of spring 1634 to raise the first clamping member 1620 relative to the second clamping member 1622 into the open position shown in FIG. 78. A flange 1660 is provided adjacent the lower end of the first clamping member 1620 to prevent the user from potentially pinching his fingers when the clamping arrangement 1610 is closed.

The second clamp member 1622 can include a plurality of mounting features 1612 extending therefrom. The mounting features 1612 can preferably be in the form of male tapered conical protrusions configured and arranged as described above in connection with FIG. 31. By way of example, the mounting features 1612 can be configured to engage apertures of the sixth accessory 14*f* at a position intermediate the terminal end of the tips and a second clamp surface 1614 on the second clamp member 1622 such as described above with respect to FIG. 30.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A power tool, comprising:

a housing;

a motor housed in the housing;

a spindle mounted in the housing and drivable in an oscillating motion by the motor about an output axis;

a clamp assembly arranged at an end of the spindle, the clamp assembly comprising a first clamping member and a second clamping member, wherein the first clamping member and the second clamping member are configured to hold an accessory therebetween;

a biasing member providing a clamping force for the clamp assembly; and a user-operable actuator for operating the clamp assembly, wherein:

the clamp assembly is configured to permit removal of the accessory from the clamp assembly while the first clamping member and the second clamping member remain coupled to the power tool;

the clamp assembly is configured such that the accessory can be retained by the clamp assembly in a clamped condition in a plurality of rotational positions including at least a first rotational position, a second rotational position, a third rotational position, and a fourth rotational position;

the user-operable actuator is a lever;

the lever pivots about a pivot axis;

the pivot axis is transverse to the output axis;

the first rotational position is spaced ninety degrees from the second rotational position;

the first rotational position is spaced ninety degrees from the fourth rotational position;

the first rotational position is spaced one-hundred and eighty degrees from the third rotational position;

the fourth rotational position is spaced ninety degrees from the third rotational position; and the fourth rotational position is spaced one-hundred and eighty degrees from the second rotational position.

2. The power tool of claim 1, wherein the spindle comprises a first section with a first diameter and a second section with a second diameter different than the first diameter, the power tool further comprising a first bearing disposed on the first section of the spindle and a second bearing disposed on the second section of the spindle.

3. The power tool of claim 2, wherein the motor drives the spindle through a drive fork, and wherein the drive fork engages the spindle between the first bearing and the second bearing.

4. The power tool of claim 1, wherein the first clamping member comprises a through hole.

5. The power tool of claim 1, wherein the clamp assembly is configured to operate in a tool-free manner.

6. The power tool of claim 5, wherein the first clamping member is outside of the housing, and wherein the second clamping member is outside of the housing.

7. The power tool of claim 5, wherein one of the first clamping member and the second clamping member include a plurality of protrusions configured to rotationally locate the accessory in the clamp assembly, and wherein the plurality of protrusions are unevenly spaced around the one of the first clamping member and the second clamping member.

* * * * *